US009072698B2

(12) United States Patent
Park et al.

(10) Patent No.: US 9,072,698 B2
(45) Date of Patent: Jul. 7, 2015

(54) METHOD FOR SCREENING ANTI-CANCER COMPOUNDS INHIBITING FUNCTION OF TM4SF5 AND ANTI-CANCER COMPOSITION CONTAINING CHALCONE COMPOUNDS

(75) Inventors: Ki Hun Park, Gyeongsangnam-do (KR); Jung Weon Lee, Seoul (KR); Young Bae Ryu, Gyeongsangnam-do (KR); Hyung Won Ryu, Gyeongsangnam-do (KR); Sin-Ae Lee, Seoul (KR)

(73) Assignees: Seoul National University Industry Foundation, Seoul (KR); Industry-Academic Cooperation Foundation Gyeongsang National University, Gyeongsangnam-do (KR)

( * ) Notice: Subject to any disclaimer, the term of this patent is extended or adjusted under 35 U.S.C. 154(b) by 283 days.

(21) Appl. No.: 13/482,568

(22) Filed: May 29, 2012

(65) Prior Publication Data

US 2012/0282619 A1 Nov. 8, 2012

Related U.S. Application Data

(62) Division of application No. 12/162,940, filed as application No. PCT/KR2007/006337 on Dec. 7, 2007, now Pat. No. 8,445,722.

(30) Foreign Application Priority Data

Dec. 7, 2006 (KR) .......................... 10-2006-0124146

(51) Int. Cl.
| C12Q 1/00 | (2006.01) |
|---|---|
| A61K 31/135 | (2006.01) |
| C07C 49/835 | (2006.01) |
| C07C 49/84 | (2006.01) |
| C07C 309/66 | (2006.01) |
| C07C 309/73 | (2006.01) |
| C07C 309/75 | (2006.01) |
| C07C 309/76 | (2006.01) |
| C07C 311/21 | (2006.01) |
| C07C 311/29 | (2006.01) |
| C07C 311/44 | (2006.01) |
| G01N 33/50 | (2006.01) |

(52) U.S. Cl.
CPC ............. A61K 31/135 (2013.01); C07C 49/835 (2013.01); C07C 49/84 (2013.01); C07C 309/66 (2013.01); C07C 309/73 (2013.01); C07C 309/75 (2013.01); C07C 309/76 (2013.01); C07C 311/21 (2013.01); C07C 311/29 (2013.01); C07C 311/44 (2013.01); G01N 33/5011 (2013.01); G01N 2333/9121 (2013.01)

(58) Field of Classification Search
None
See application file for complete search history.

(56) References Cited

U.S. PATENT DOCUMENTS

| 5,922,566 A | 7/1999 | Bandman et al. |
|---|---|---|
| 6,632,617 B1 | 10/2003 | Bandman et al. |
| 7,851,654 B2 | 12/2010 | Park et al. |

FOREIGN PATENT DOCUMENTS

| FR | 2874215 | 2/2006 |
|---|---|---|
| KR | 10-2003-0036993 | 5/2003 |
| KR | 10-2005-0030653 | 5/2005 |

OTHER PUBLICATIONS

Lin et al (Exp Cell Res, 2004, 293(1): 1-13).*
Khare et al (Am J Physiol Gastrointest Liver Physiol, 2006, 291(1): G1100-1112).*
Nam et al (Cancer Res, 2005, 65: 9185-9189).*
Choi et al., "Regulation of TM4SF5-Mediated Tumorigenesis Through Induction of Cell Detachment and Death by Tiarellic Acid," *Biochimica et Biophysica Acta*, vol. 1783, pp. 1632-1641, 2008.
European Search Report for corresponding EP Application No. 07851308.2, dated Mar. 12, 2010.
Lee et al., "Focal Adhesion and Actin Organization by a Cross-Talk of TM4SF5 with Intergrin Alpha2 are Regulated by Serum Treatment," *Exp. Cell Res.*, vol. 312, No. 16, pp. 2985-2993, 2006.
Lee et al., "Tetraspanin TM4SF5 Mediates Loss of Contact Inhibition Through Epithelial-Mesenchymal Transition in Human Hepatocarcinoma," *J. Clin. Invest.*, vol. 118, No. 4, pp. 1354, 1366, 2008.
Muller-Pillacsch et al., "Identification of a New Tumour-Associated Antigen TM4SF5 and its Expression in Human Cancer," *Gene*, vol. 208, pp. 25-30, 1998.
Seo et al.,"Sulfonamide Chalcone as a New Class of α-Glucosidase Inhibitors," *Bioorganic and Medicinal Chemistry Letters*, vol. 15, No. 24, pp. 5514-5516, 2005.

* cited by examiner

*Primary Examiner* — Sean Aeder
(74) *Attorney, Agent, or Firm* — Klarquist Sparkman, LLP

(57) ABSTRACT

The present invention relates to a method for screening an anticancer compound and an anticancer compound screened using the method, and more particularly, to a method for screening an anticancer compound, the method comprising: culturing cancer cells expressing the oncogenic protein transmembrane 4 L6 family member 5 (TM4SF5), expressed as the polypeptide of SEQ ID NO: 2, treating the cancer cells with an anticancer candidate, and determining that the anticancer candidate is an anticancer substance when the candidate exhibits antagonistic activity against tumor formation and metastasis based on several events through the molecular mechanism of TM4SF5. The present invention also relates to chalcone compounds screened to have anticancer activity using the method, and an anticancer composition comprising the compound as an effective ingredient.

11 Claims, 39 Drawing Sheets

| Compounds / cells | SNU449Cp | SNU449Tp |
|---|---|---|
| DMSO | | |
|  TSAHC | | |
|  (4,4'-Dihydroxychalcone) | | |
|  (4'-Methoxy-4-hydroxychalcone) | | |
|  (4'-Amino-4-hydroxychalcone) | | |

METHOD FOR SCREENING ANTI-CANCER COMPOUNDS INHIBITING FUNCTION OF TM4SF5 AND ANTI-CANCER COMPOSITION CONTAINING CHALCONE COMPOUNDS

This is a divisional of U.S. patent application Ser. No. 12/162,940, filed May 14, 2009 now U.S. Pat. No. 8,445,722, now pending, which is the §371 U.S. national stage of International Application No. PCT/KR2007/006337, filed Dec. 7, 2007, which in turn claims the priority benefit of Korean Application No. 10-2006-0124146, filed Dec. 7, 2006, all of which are incorporated herein by reference in their entirety.

TECHNICAL FIELD

The present invention relates to a method for screening an anticancer compound, and more particularly, to a method for screening a compound inhibiting TM4SF5-mediated tumor formation, development and metastasis. Also, the present invention is concerned with a chalcone compound screened as an anticancer substance using the method and an anticancer composition comprising the chalcone compound as an effective ingredient.

BACKGROUND ART

Transmembrane 4 L6 family member 5 (TM4SF5 or L6H) is a protein that is homologous to a tumor-associated antigen L6 (TM4SF1), which is a member of the transmembrane 4 L6 superfamily. The transmembrane 4 L6 superfamily further includes IL-TMP and L6D. The L6 antigen (TM4SF1) is highly expressed on colon, lung, breast, and ovarian carcinomas. The TM4SF5 protein (L6H), homologous to the L6 antigen (TM4SF1), is also highly expressed in several types of cancer including pancreatic, gastric, colon and liver carcinomas (Muller-Pillasch, F. et al., *Gene*, 208:25, 1998; Pascual-Le Tallec, L. et al., *J. Clin. Endocrinol. Metab.*, 87:501, 2002). TM4SF5 mRNA is expressed at lower levels in gastric cancer tissues compared to the L6 antigen (TM4SF1), but is overexpressed in liver and gastric carcinoma cell lines (Kaneko, R. et al., *Am. J. Gastroenterol.*, 96(12):3457, 2001).

Based on the research results, TM4SF5 has been recently registered as a novel oncogene, as disclosed in U.S. Pat. No. 6,350,581 B1, in which TM4SF5 is named a human tumor-associated antigen (TUAN). The present inventors recently found, through the expression of TM4SF5 in COST cells, that TM4SF5-mediated actin reorganization, focal adhesion formation and focal adhesion kinase (FAK) phosphorylation at Tyr925 are induced via integrin α2 subunit, and are regulated (inhibited) by treatment with serum containing cell growth factors (Lee, S. Y. et al., *Exp. Cell Res.*, 312:2983, 2006).

However, the molecular mechanism of TM4SF5-mediated tumorigenesis is poorly understood. The functions of TM4SF5 at the molecular level are unknown, and the evidence for the carcinogenic role of TM4SF5 has not been presented at the biochemical and cell biological levels.

On the other hand, chalcones are widely distributed in edible plants and are known as precursors of flavonoids or isoflavonoids. Derivatives of such chalcones are constituents of yellow pigments of plants, which affect plant color and protect plants from harmful ultraviolet rays (Methodology of Natural Product Chemistry, W. S. Woo, Seoul National University Press). Chalcone derivatives are abundant in *Coreopsis* plants, which is the genus of the family Asteraceae. Representative chalcones include 2',6'-dihydroxy-4'-methoxychalcone and carthamine, and are contained in plants including cinnamon, safflower and pepper. Dihydrochalcone is contained mainly in certain plant species of the families Rosaceae and Ericaceae. Phloridzin is a dihydrochalcone that is found primarily in apple peels, and is responsible for the resistance of apple trees to diseases.

Such chalcone derivatives have been known to have various pharmaceutical activities, such as antiprotozoal activity (Liu, M. et al., *J. Med. Chem.*, 44:4443, 2001), anti-inflammatory activity (Babu, M. A. et al., *Bioorg. Med. Chem.*, 10:4035, 2003), immunomodulation (Barfod, L. et al., *Int. Immunopharmacol.*, 2:545, 2002), inhibition of nitric oxide production (Rojas, J. et al., *Bioorg. Med. Chem. Lett.*, 12:1951, 2002), anticancer activity (Kumar, S. K. et al., *J. Med. Chem.*, 46:2813, 2003), and anti-HIV activity (Artico, M. et al., *J. Med. Chem.*, 41:3984, 1998).

In addition, Korean Patent Publication 10-2003-0036993 discloses that chalcone compounds have inhibitory activity against matrix metalloproteinase (MMP), which degrades components of basement membrane (Park, K. H. et al., *Bioorg. Med. Chem. Lett.*, 15:5514, 2004).

Among chalcone compounds, sulfonamide- or sulfonate-substituted chalcone derivatives have been reported to have specific biological properties, not shown in naturally occurring chalcones. In particular, the present inventors found that sulfonamide chalcone derivatives have strong inhibitory activity against α-glucosidase (Park, K. H. et al., *Bioorg. Med. Chem. Lett.*, 15:5514, 2004; Korean Patent Publication 10-0751899). The present inventors also recently reported sulfonate chalcone derivatives as selective K(+) channel blockers (Park, K. H. et al., *Bioorg. Med. Chem. Lett.*, 2007).

However, there is no report stating that sulfonamide or sulfonate chalcone derivatives have anticancer activity through a mechanism of inhibiting the oncogenic TM4SF5 protein.

In this regard, the present inventors have conducted intensive and thorough research, thus resulting in the finding that the oncogenic potential of TM4SF5, shown in human carcinoma cells, is due to its ability to promote epithelial-mesenchymal transition (EMT), leading to the loss of contact inhibition. Also, the present inventors found that the oncogenic function of TM4SF5 is mediated via a new pathway, which is composed of a series of steps that include focal adhesion kinase (FAK) phosphorylation and cytosolic p27$^{kip1}$ accumulation, leading to inhibition of RhoA activity and changes in cell morphology. Based on this finding, the present inventors have made many efforts to screen anticancer substances inhibiting TM4SF5-mediated tumor formation, development and metastasis, thereby leading to the present invention.

SUMMARY OF THE INVENTION

It is therefore an object of the present invention to provide a method for screening an anticancer compound inhibiting TM4SF5-mediated tumor formation, development and metastasis.

It is another object of the present invention to provide an anticancer compound screened using the method, preferably a sulfonamide or sulfonate chalcone compound, and an anticancer composition comprising the anticancer compound as an effective ingredient.

In order to achieve the above objects, the present invention provides a method for screening an anticancer compound, the method comprising:
(a) culturing cancer cells expressing the polypeptide of SEQ ID NO: 2, and treating the cancer cells with an anticancer candidate;
(b) detecting at least one of the following in the cancer cells treated with the anticancer candidate: (i) phosphorylation of a tyrosine residue at position 577 (Tyr577) of an amino acid sequence encoding focal adhesion kinase (FAK), (ii) binding FAK to Rho-GTPase activating protein (RhoGAP) or FAK to GTPase regulator associated with FAK (GRAF), (iii) the expression level and stability of cytosolic p27$^{Kip1}$, (iv) RhoA activity, and (v) Rac1 activity; and (c) determining whether the anticancer candidate can be an anticancer substance when the following events are exhibited, compared to when treatment with the anticancer candidate is not conducted: (i) decreased phosphorylation of FAK on Tyr577, (ii) inhibition of binding of FAK to RhoGAP or FAK to GRAF, (iii) reduced cytosolic p27$^{Kip1}$ expression and stability, (iv) increased RhoA activity, or (v) decreased Rac1 activity.

In the method of the present invention, step (b) further includes detecting at least one selected from the group consisting of cell morphology, expression of a protein involved in cell adhesion formation, cell-cell contact pattern or contact growth, expression of α-smooth muscle actin (α-SMA) or vimentin, expression of E-cadherin, and epithelial-mesenchymal transition (EMT); and the step (c) further includes the following events: a change in cell morphology from a rod shape into a polygonal shape, reduced expression of proteins involved in cell adhesion formation, maintenance of cell-cell contacts, contact inhibition of cell growth, reduced expression of α-SMA or vimentin, increased expression of E-cadherin, or reduced epithelial-mesenchymal transition (EMT).

In addition, step (b) further includes detecting at least one selected from the group consisting of cell migration or motility in the presence of an extracellular matrix or serum, the invasion into collagen gels which comprise the extracellular matrix, the invasion into Matrigel which is an extracellular matrix complex, and matrix metalloproteinase (MMP) activity; and the step (c) further includes the following events: decreased cell migration or motility in the presence of an extracellular matrix or serum, decreased invasion into collagen gels, decreased invasion into Matrigel, or reduction of MMP activity.

The present invention also provides an anticancer chalcone compound that is screened using the method and is represented by Chemical Formula 1 or 2, below, and an anticancer composition comprising the chalcone compound as an effective ingredient.

[Chemical Formula 1]

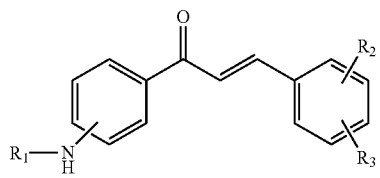

wherein, $R_1$ represents $R_4SO_2$—; $R_2$ and $R_3$ are independently hydrogen or hydroxy; and $R_4$ is ($C_1$-$C_5$) alkyl or ($C_6$-$C_{10}$) aryl having one or more substituents selected from the group consisting of hydrogen, halogen, nitro and ($C_1$-$C_5$) alkyl.

[Chemical Formula 2]

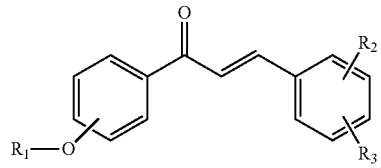

wherein, $R_1$ represents $R_4SO_2$—; $R_2$ and $R_3$ are independently hydrogen or hydroxy; and $R_4$ is ($C_1$-$C_5$) alkyl or is ($C_6$-$C_{10}$) aryl having one or more substituents selected from the group consisting of hydrogen, halogen, nitro and ($C_1$-$C_5$) alkyl.

Other features and aspects of the present invention will be apparent from the following detailed description and the appended claims.

DETAILED DESCRIPTION OF THE INVENTION, AND PREFERRED EMBODIMENTS

Figure 1:
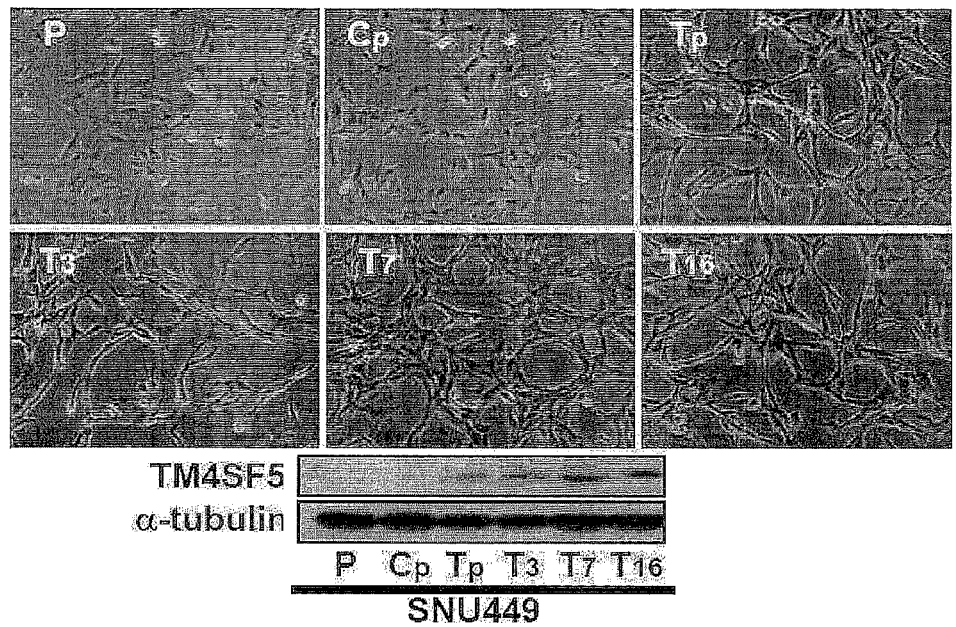
FIG. 1 shows photographs of SNU449p, SNU449 Cp, Tp, T3, T7 and T16 cells and the results of Western blotting.

In one aspect, the present invention relates to a method for screening an anticancer compound based on various cell biological and biochemical events induced by the expression of transmembrane 4 L6 family member 5 (TM4SF5), which functions as a tumor inducer.

The tumor-associated protein TM4SF5 formed by a polypeptide represented by SEQ ID NO: 2, which is expressed from a polynucleotide represented by SEQ ID NO: 1, is a protein that is homologous to the tumor-associated antigen L6. TM4SF5 is a hydrophobic protein that contains four transmembrane spanning regions, two extracellular loops and cytoplasmic N- and C-termini. TM4SF5 is highly expressed in several types of cancer, including pancreatic, gastric, colon and liver carcinomas.

Transmembrane 4 superfamily (TM4SF) proteins are known to form massive tetraspanin web structures with cell adhesion molecules, such as integrin, to perform their biological functions including cell adhesion, proliferation and migration. Epithelial tissue consisting of epithelial monolayers are formed through cell-cell contact between adjacent cells, which is mediated by strong interaction between cell adhesion-associated molecules, such as E-cadherin, or by the interaction of cell surface integrin receptors with extracellular matrix proteins, thus leading to strong attachment to basal epithelial cell surface. When disrupted, the strongly linked tissue monolayer loses its function as epithelial cells, which allows the release of tumor cells from primary tumors.

Integrin is a family of cell adhesion receptors. When cell adhesion is mediated by the interaction of integrins with extracellular matrix, diverse intracellular signaling molecules are activated to perform their functions and integrins can play a critical role in regulating actin filament reorganization. Signaling molecules involved in integrin-mediated cell adhesion include focal adhesion kinase (FAK) and Rho-GTPase activating protein (RhoA GTPase).

The present inventors found that TM4SF5 is closely associated with integrin-mediated signal transduction in epithelial hepatocarcinoma cells (SNU449, KCLB No. 00449), and this association was estimated through the following observations:

(1) TM4SF5 expression increases not $pY^{397}FAK$ but $pY^{577}FAK$;
(2) $Y^{577}F$ FAK mutation inhibits the binding between FAK and RhoGAP by TM4SF5;
(3) TM4SF5 expression inhibits RhoA activity by promoting binding of FAK to p190RhoGAP or FAK to GRAF through interaction between them; and
(4) independent of the above mechanism, TM4SF5 expression enhances the expression and stabilization of cytosolic $p27^{kip1}$, which leads to the down-regulation of RhoA activity.

That is, the present inventors have conducted intensive and thorough research based on the above results. This research resulted in the understanding of the functions of TM4SF5 at the molecular level and the biochemical and cell biological characterization of the carcinogenic mechanism of TM4SF5.
Properties of Rho Family Proteins The Rho family of GTP-binding proteins, including RhoA and Rac1, is involved in cell adhesion and detachment. The proteins exist in two interconvertible forms: a GTP-bound active form, in which they display their physiological activity, and a GDP-bound inactive form, in which their functions are blocked. Rho family proteins typically have low GTPase activity, and play critical roles in focal adhesion (FA) and integrin assembly and disassembly upon cell adhesion. RhoA GTPase is composed of RhoA, Rac1 and Cdc42, which plays important roles in actin reorganization through actin polymerization and myosin light chain phosphorylation through their downstream effectors, such as LIMK, PAK1, MLCK, mDia and ROCK.

The recruitment of signaling molecules to focal adhesion is dependent on the activity of focal adhesion kinase (FAK). This is because the phosphorylation of proteins by FAK exposes binding sites for other proteins. That is, focal adhesion formation increases in FAK-deficient cells. In other words, the tyrosine phosphorylation of FAK promotes FA formation. Also, FAK is involved in cell motility. FAK overexpression enhances cell motility and invasion.

Such FAK activities are closely related to RhoA. RhoA activity is elevated in FAK-deficient cells. This is because FAK phosphorylation causes Rho-GTPase activating protein (RhoGAP) and GTPase regulator associated with FAK (GRAF), bound to the C-terminal domain of FAK, to stimulate RhoGAP to suppress RhoA activity.

However, Rac1 of the Rho family proteins counteracts RhoA. Rac1 activation reduces focal adhesion formation and enhances cell motility. The disassembly of focal adhesions, which interrupts cell migration, promotes cell migration by growth factors inducing focal adhesion disruption.
Phosphorylation of FAK and Reduction of RhoA Activity by TM4SF5 Expression The present inventors found that the expression of TM4SF5 increases not $pY^{397}FAK$ but $pY^{577}FAK$ and promotes binding of FAK to p190RhoGAP or FAK to GRAF through interaction between the proteins.

Figure 8:
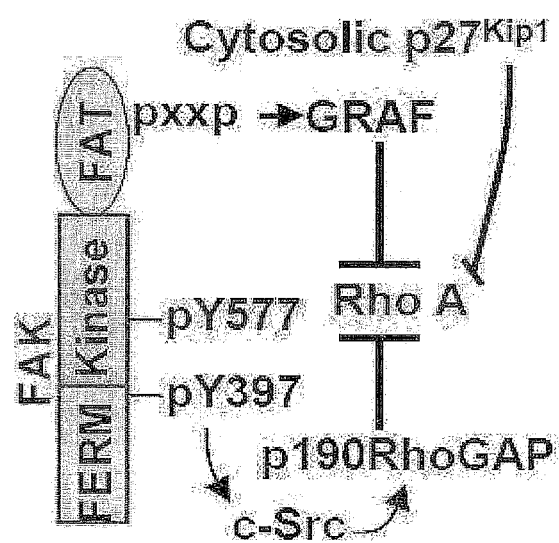
FIG. 8 is a schematic presentation of FAK-RhoA signaling.

$pY^{577}FAK$ means trrosine phosphorylation of FAK at position 577. Thus, the increase of $pY^{577}FAK$ according to TM4SF5 expression represents the increase of FAK phosphorylation, which stimulates RhoGAP to induce binding of RhoGAP to FAK or GRAF to FAK, resulting in the reduction of RhoA activity. In this case, Rac1 activity is increased. FIG. 8 is a schematic presentation of FAK-RhoA signaling associated with RhoGAP.

Figure 3:
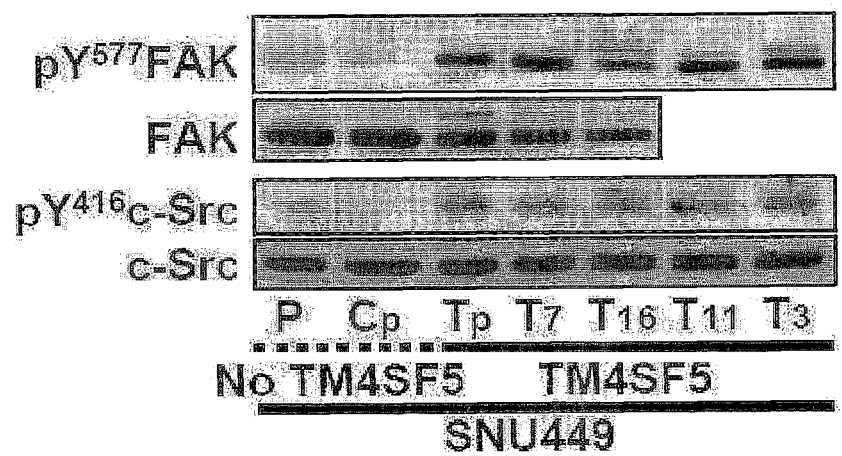
FIG. 3 shows the results of Western blotting for indicated proteins.
Figure 4:
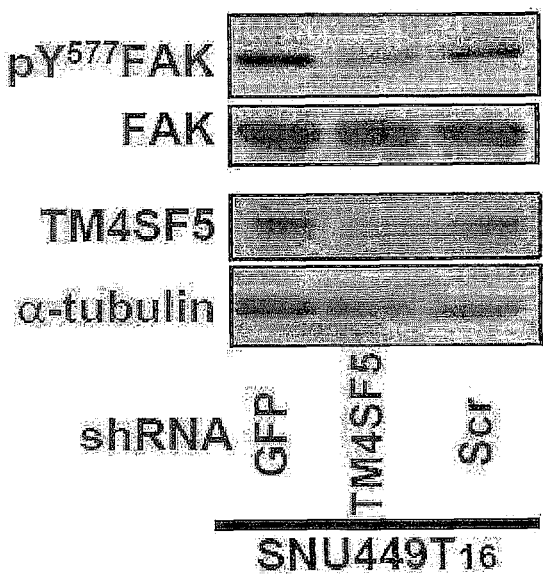
FIG. 4 shows the results of an in vitro pull-down assay for the activity of RhoA and Rac1.
Figure 5:
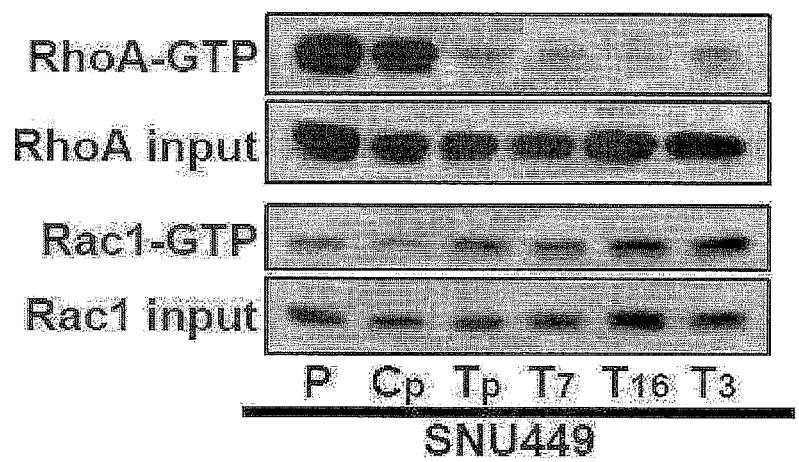
FIG. 5 shows the results of Western blotting for SNU449p, SNU449 Cp and SNU449Tp cells.
Figure 6:
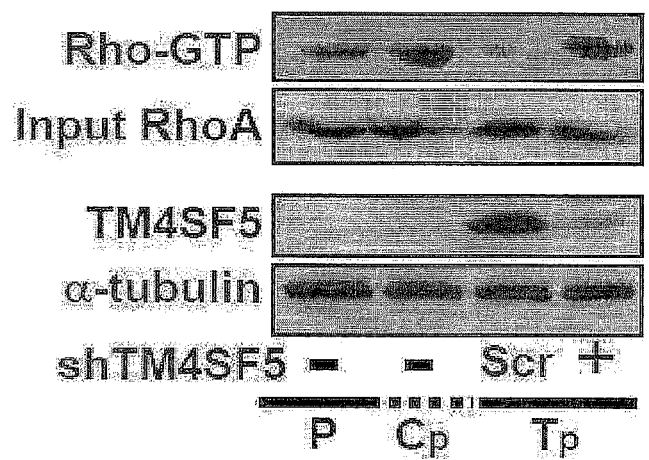
FIG. 6 shows analysis results of the RhoA activity of some cells of FIG. 5.

When FAK was phosphorylated on Tyr577 ($pY^{577}FAK$) and c-Src was phosphorylated on Tyr416 ($pY^{416}cSrc$) in TM4SF5-expressing cells, Rac1 activity was elevated in both cases, whereas RhoA activity was decreased in both cases (FIGS. 3 and 5). The increase of $pY^{577}FAK$ and the suppression of RhoA activity by TM4SF5 were reversed when TM4SF5 expression was inhibited using an siRNA against TM4SF5 (FIGS. 4 and 6).

Figure 9:
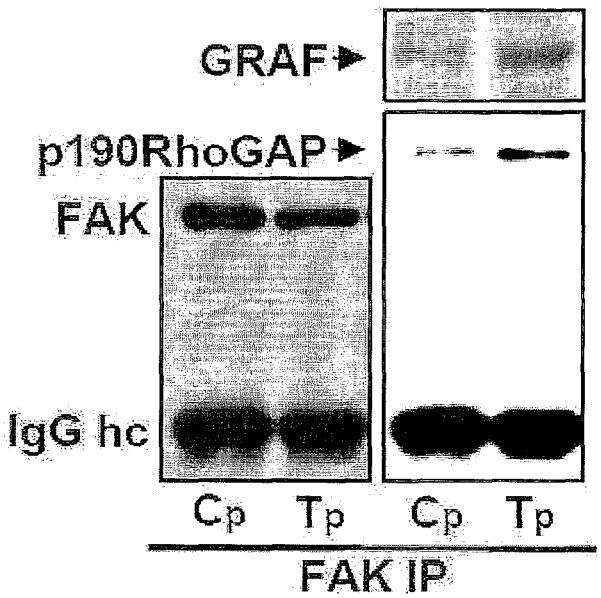
FIG. 9 shows the results of Western blotting with antibodies against p190RhoGAP, GRAF and FAK for SNU449Tp cells.
Figure 10:
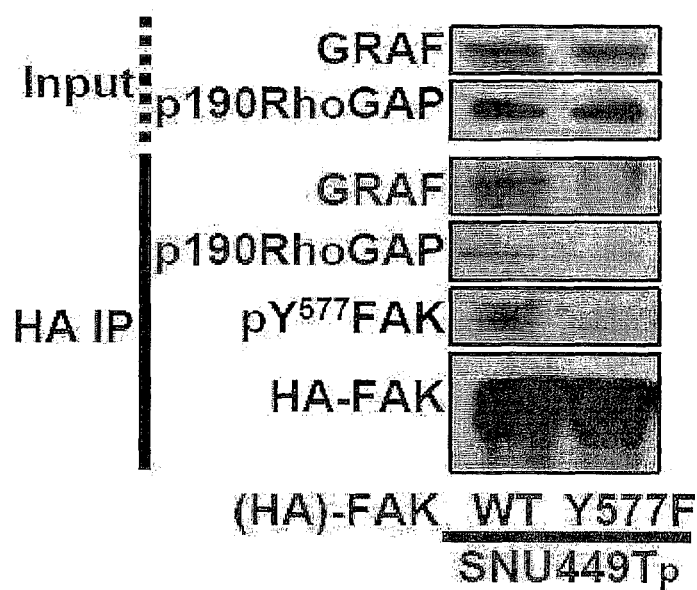
FIG. 10 shows the results of Western blotting of lysates from SNU449Tp cells, in which either an (HA)3-tagged FAK wild type or a Y577F FAK mutant were overexpressed.

Furthermore, a strong binding was observed between FAK and p190RhoGAP or FAK and GRAF in TM4SF5-expressing cells compared to parental cells not expressing TM4SF5 (FIG. 9). When the Tyr577 residue of FAK was replaced with phenylalanine to express a mutant protein, TM4SF5-mediated binding of FAK to p190RhoGAP or FAK to GRAF was reduced (FIG. 10).

These results indicate that $pY^{577}FAK$ plays an important role in the FAK-RhoA signaling pathway in TM4SF5-expressing cells, and that the reduction of $pY^{577}FAK$, inhibition of binding of FAK to RhoGAP or FAK to GRAF, reduction of Rac1 activity or an increase in RhoA activation suppresses the expression of the tumorigenic protein TM4SF5.

Figure 12:
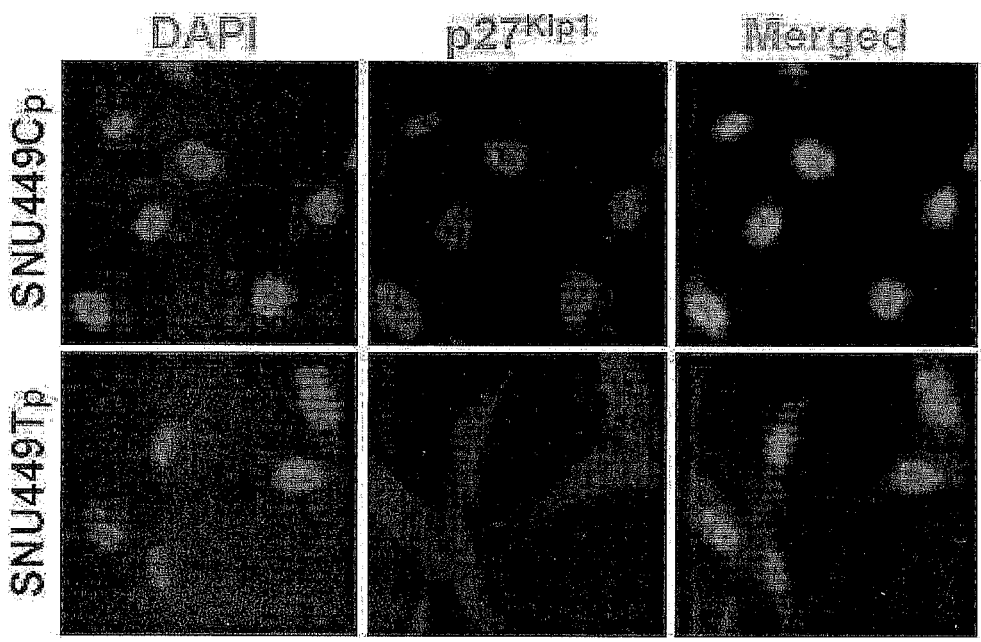
FIG. 12 shows the results of immunofluorescent staining of SNU449 Cp cells and SNU449Tp cells.
Figure 13:
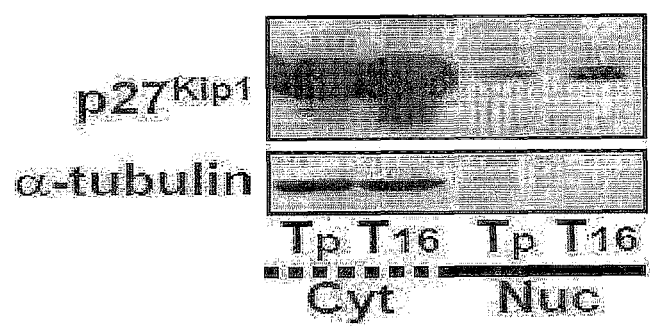
FIG. 13 shows the results of Western blotting of cytosolic and nuclear fractions with anti-p27$^{kip1}$ and α-tubulin antibodies.

Cytosolic p27$^{kip1}$ Accumulation and Reduction of RhoA Activity by TM4SF5 Expression The present inventors found that the p27$^{kip1}$ protein is present in a remarkably high concentration in TM4SF5-expressing cells, and that this is due to the high stability of p27$^{kip1}$ mRNA and p27$^{kip1}$ protein in the cytosol (FIG. 12). In contrast, in TM4SF5-null cells, a small amount of p27$^{kip1}$ was observed, and mostly in the nucleus (FIG. 13).

The p27$^{kip1}$ protein, which is a cyclin-dependent kinase (CDK) inhibitor, is known to have tumor-suppressive functions in the nucleus. The phosphorylation of the serine residue at position 10 during the G0-G1 transition stimulates the translocation of p27$^{kip1}$ into the cytosol. The phosphorylation of p27$^{kip1}$ on Ser10 is mediated by kinase interacting with stathmin (KIS) and PKB/Akt, or by Mirk/dyrk1B and Erk1/2 in quiescent cells in vitro, respectively.

Figure 19:
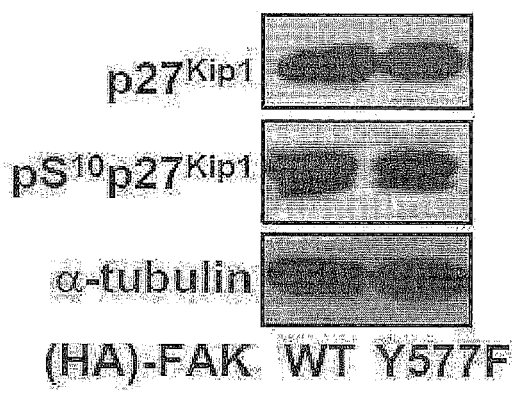
FIG. 19 shows the results of Western blotting of lysates from SNU449Tp cells, in which an (HA)3-tagged FAK wild type and a Y577F FAK mutant were overexpressed.
Figure 20:
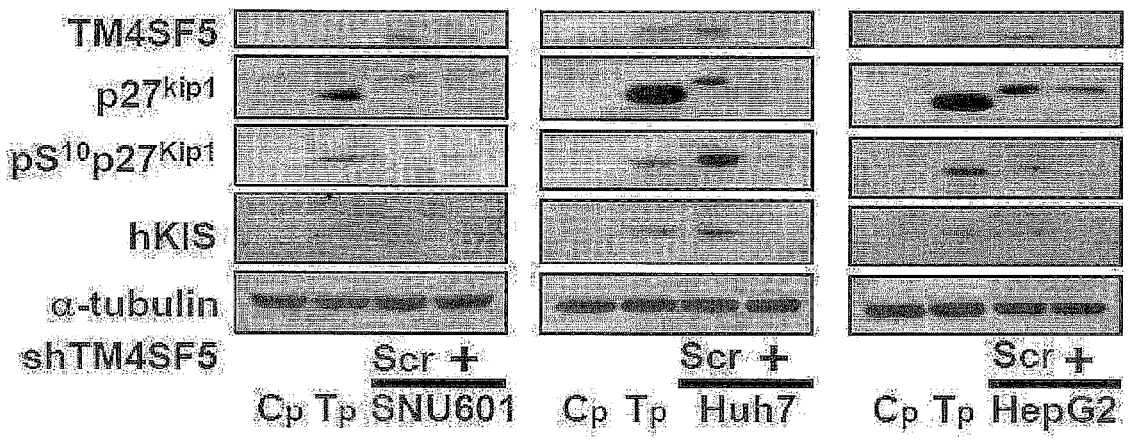
FIG. 20 shows the results of Western blotting of lysates from Huh7, hepatocarcinoma cells transfected with various shRNAs.

The phosphorylation on Ser10 rather than on Thr187 or Thr157 is significantly related to TM4SF5 expression, and contributes to the cytosolic translocation and stabilization of p27$^{kip1}$. pT$^{157}$p27$^{kip1}$ and pT$^{187}$p27$^{kip1}$ are not related to TM4SF5-mediated events. When TM4SF5 expression was suppressed using shRNAs and the like in hepatocarcinoma cells expressing TM4SF5, expression and Ser10 phosphorylation of p27$^{kip1}$ were reduced, and cytosolic p27$^{kip1}$ was also reduced (FIGS. 19 and 20). These results are consistent with the recently reported result that the cytosolic translocation of p27$^{kip1}$ was inhibited by the oncogenic Ras protein in transgenic mice expressing a p27$^{kip1}$S10A mutant.

Figure 27:
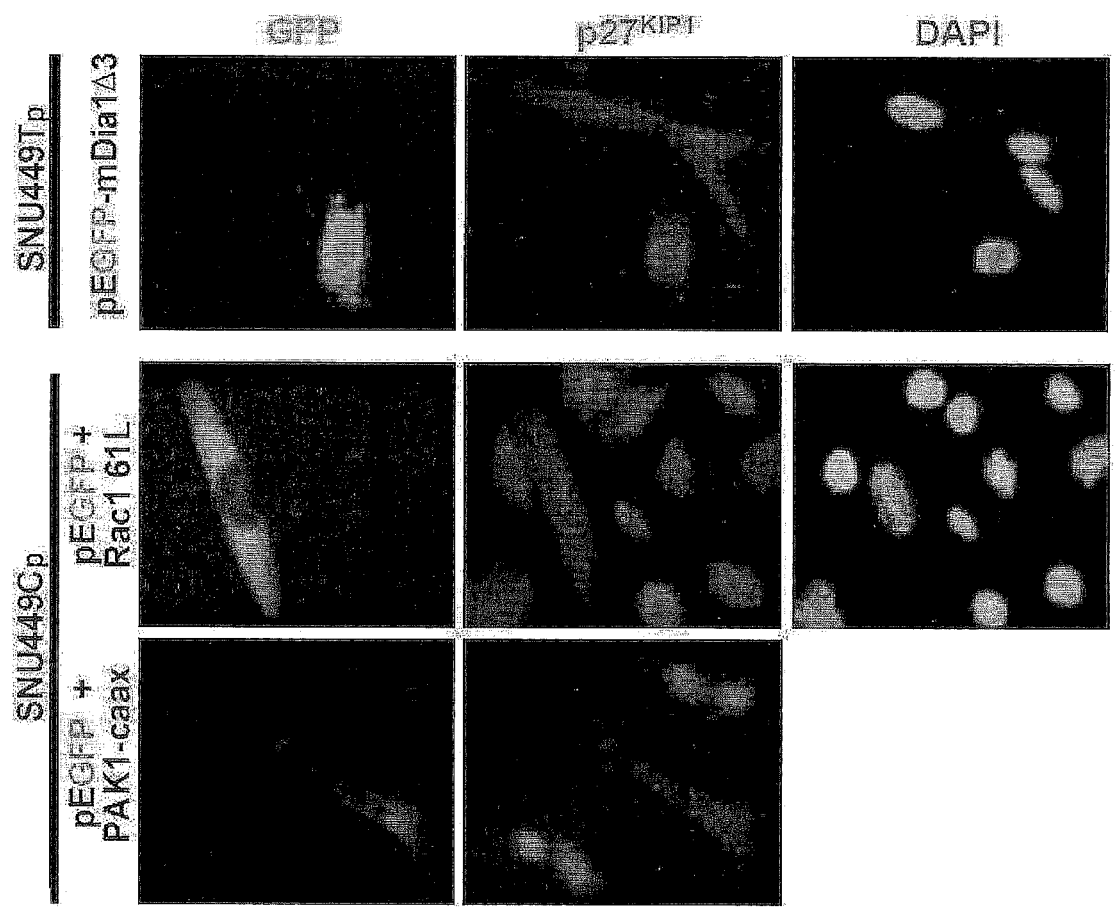
FIG. 27 shows the results of immunofluorescent staining of SNU449Tp cells, which were transfected with an active mDia mutant, active Rac1 (Rac1 61L) and PAK1 (PAK1-caax).

According to a recent report, cytosolic p27$^{kip1}$ has been shown to reduce RhoA signaling activity by inhibiting the binding of GTP exchange factor (GEF) to RhoA to activate RhoA through direct binding. In order to identify the relationship between cytosolic p27$^{kip1}$ accumulation and RhoA signaling, the change in intracellular location of p27$^{kip1}$ was examined when Rho GTPase was activated. When RhoA or its downstream mediator mDia was activated, or cells were treated with an RhoA activator LPA, cytosolic p27$^{kip1}$ expression levels decreased (FIG. 27). This is because when RhoA signaling is activated, the p27$^{kip1}$ protein is no longer stabilized, and is localized not in the cytosol but in the nucleus. That is, a regulatory connection is present between cytosolic p27$^{kip1}$ and Rho GTPase. Thus, the expression of TM4SF5 enhances p27$^{kip1}$ expression and stabilization in the cytosol, resulting in the down-regulation of RhoA activity.

Figure 18:
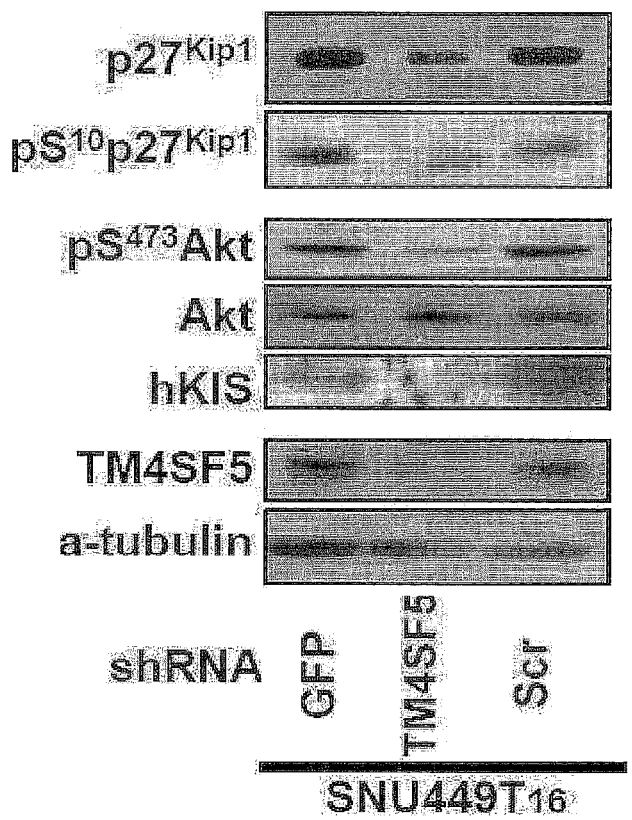
FIG. 18 shows the results of Western blotting with indicated antibodies.

However, the inhibition of RhoA activity by TM4SF5-mediated p27$^{kip1}$ accumulation and the inhibition of RhoA activity by TM4SF5-mediated binding between FAK and RhoGAPs are caused via different signaling pathways. This is supported by the finding that the overexpression of an Y577F FAK mutant (Tyr577 was replaced with phenylalanine) does not affect the expression and Ser10 phosphorylation of p27$^{kip1}$ (FIG. 18).

In contrast to RhoA activity inhibition, the cytosolic accumulation of p27$^{kip1}$ activates Rac1. In other words, the expression of the activated Rac1 and its downstream mediator PAK1 leads to the cytosolic accumulation of p27$^{kip1}$ (lower panel, FIG. 27).

Change in Cell Morphology by TM4SF5-Mediated Down-Regulation of RhoA Activity

Figure 2:
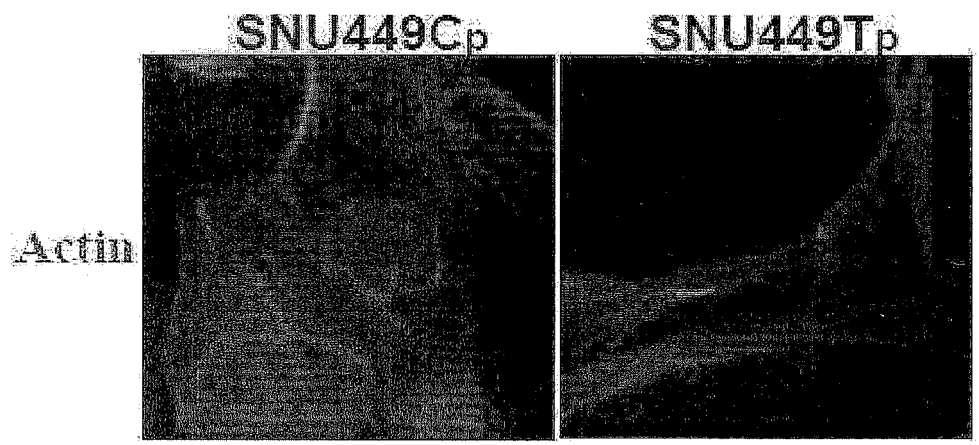
FIG. 2 shows the cytoskeletal actin network stained with rhodamine-conjugated phalloidin in SNU449 Cp cells and SNU449Tp cells.

In parental hepatocarcinoma cells (SNU449) not expressing TM4SF5, actin maintains polygonal cell morphology, flattened to form a fibrous structure. In TM4SF5-expressing SNU449Tp cells, abnormal actin clusters are formed along the elongated rod cell shape (FIG. 2).

Figure 7:
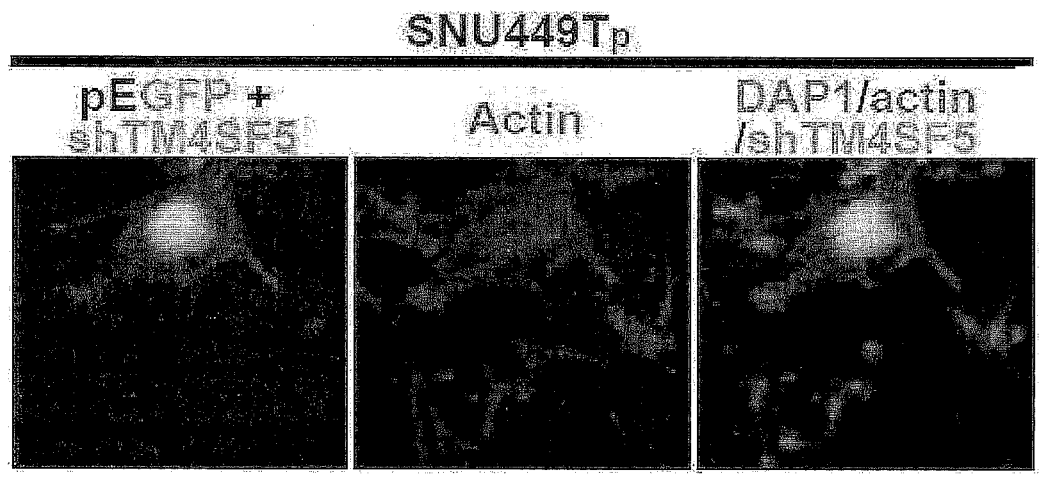
FIG. 7 shows the results of fluorescent staining with rhodamine-conjugated phalloidin and DAPI for SNU449Tp cells, which had been transfected with pEGFP and shTM4SF5 to culture for 24 hrs.

The signal transduction involved in morphological change is mediated by Rac1 and RhoA activities. In TM4SF5-expressing cells, Rac1 activity is elevated, whereas RhoA activity is reduced. This is reversed when TM4SF5 expression is inhibited using a siRNA against TM4SF5. That is, siRNA-introduced cells as that of parental cells, return to the same polygonal shape having a highly fibrous actin structure, whereas cells not treated with the siRNA maintain a shape containing abnormal actin clusters, which are formed by TM4SF5 expression (FIG. 7).

Figure 22:
FIG. 22 shows confocal scanning microscope images of immunofluorescent stained SNU449 Cp cells, in which FLAG-tagged p27$^{kip1}$ was overexpressed.
Figure 23:
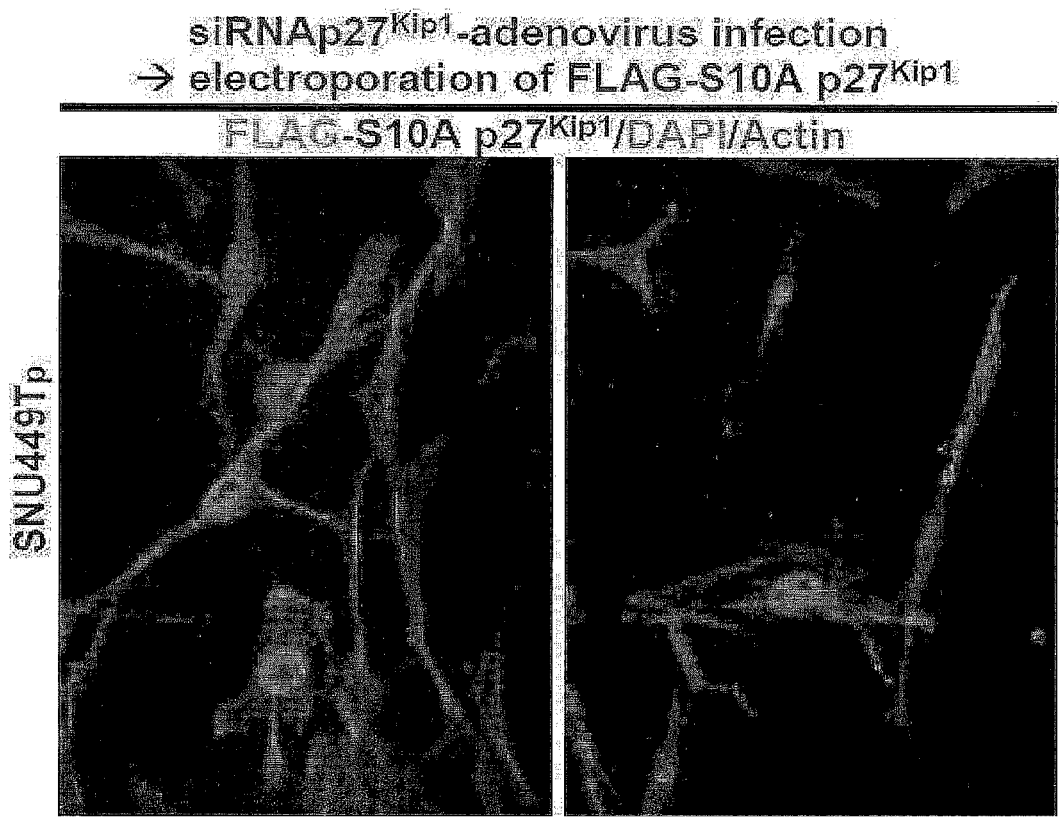
FIG. 23 shows the results of immunofluorescent staining of SNU449Tp cells in which p27$^{kip1}$ expression was inhibited.

In addition, since p27$^{kip1}$ is highly expressed in TM4SF5-expressing cells, the change in the p27$^{kip1}$ protein expression level also affects cell morphology. When p27$^{kip1}$ is overexpressed in parental cells not expressing TM4SF5, the cells are elongated (FIG. 22). In contrast, when TM4SF5-expressing cells are treated with a p27$^{kip1}$S10A mutant inhibiting the expression or serine phosphorylation of p27$^{kip1}$, they undergo morphological change into the same polygonal shape as that of parental cells (FIG. 23).

With respect to the relation between cytosolic p27$^{kip1}$-mediated morphological change and Rho signaling, when Rho GTPase is activated in TM4SF5-expressing cells (through RhoA activation, mDia activation or LPA treatment), the activation of RhoA signaling results in no more stabilization of p27$^{kip1}$, and in turn induces the localization of p27$^{kip1}$ in the nucleus, leading to the reduction of cytosolic p27$^{kip1}$ expression level, which results in morphological change into the same polygonal shape as that of parental cells. In contrast, the activation of Rac1 and the expression of its downstream mediator PAK1 change the morphology of parental cells not expressing TM4SF5 into an elongated rod shape, and cause the cytosolic accumulation of p27$^{kip1}$ (FIG. 27).

In conclusion, there is a regulatory connection between cytosolic p27$^{kip1}$ and Rho GTPase, and the regulation of Rho GTPase activity by cytosolic p27$^{kip1}$ induces the morphological change of TM4SF5-expressing cells. The morphological change is associated with events described below.

EMT and Cell-Cell Contact According to TM4SF5 Expression (1) Reduction in Cell-Cell Contact and Induction of Epithelial-Mesenchymal Transition (EMT)

The present inventors found that the cytosolic p27$^{kip1}$ accumulation by TM4SF5 expression induces the loss of cell-cell contact and promotes EMT.

The activity of RhoA protein upon intercellular adhesion varies depending on cell types and signaling events. The aforementioned inhibition of RhoA activity through TM4SF5-mediated p27$^{kip1}$ accumulation brings about a change in the intracellular actin cytoskeleton, which is associated with cell-cell contact mediated by cadherin/catenin complexes.

Figure 29:
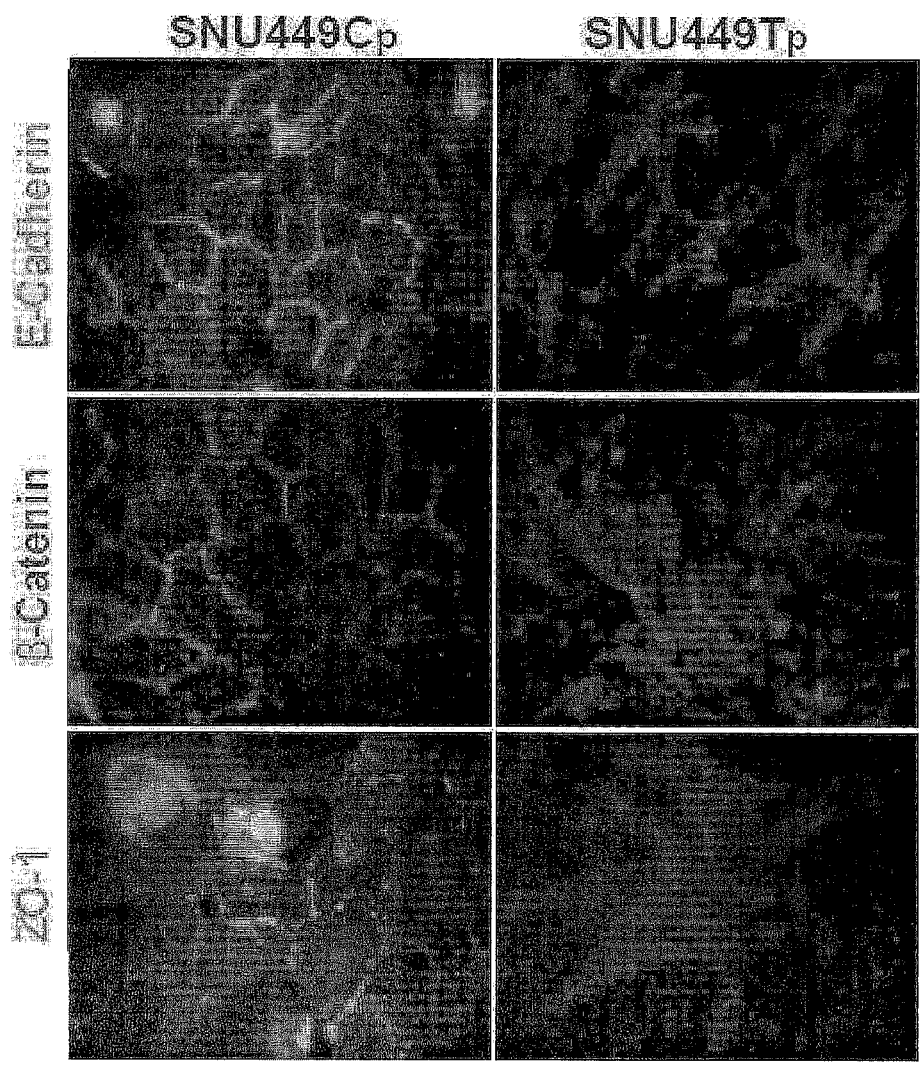
FIG. 29 shows the results of immunostaining for E-cadherin, β-catenin and ZO1 of SNU449 Cp and SNU449Tp cells.

Parental cells, not expressing TM4SF5, express high levels of cell adhesion molecules including E-cadherin, ZO-1 and desmoplakin, which are well arranged at cell adhesion sites. In contrast, TM4SF5-expressing cells express lower levels of cell adhesion molecules, and exhibit sporadic expression patterns because intracellular adhesion is not well established (FIG. 29). At the same time, the expression of snail, a transcriptional factor repressing E-cadherin expression, is reduced. Thus, the reduction of E-cadherin expression is not dependent on snail, but is dependent on TM4SF5 (FIG. 29).

In contrast, TM4SF5-expressing cells express high levels of α-SMA and vimentin, which are involved in epithelial-mesenchymal transition (EMT). The EMT plays an important role in physiological processes such as cell shape determination and wound healing, and is involved in chronic inflammation and tumor metastasis.

The inhibition of RhoA activity by TM4SF5-mediated $p27^{kip1}$ accumulation leads to a change in cell morphology into an elongated shape because RhoA inactivation induces the abnormal reorganization of actin filaments. This morphological change promotes EMT, which disrupts cell-cell adhesion. Taken together, TM4SF5-mediated α-SMA expression and EMT are induced through the inhibition of RhoA activity, and lead to a morphological change in cell length.

Thus, the inhibition of $p27^{kip1}$ expression in TM4SF5-expressing cells suppresses EMT and maintains cell-cell contact. This is because the inhibition of $p27^{kip1}$ expression leads to increased accumulation of $p27^{kip1}$ in the nucleus rather than in the cytosol, which drives the morphological change from an elongated shape into a polygonal shape, which is the same as that of parental cells. The control of the intracellular localization, that is, nuclear and cytosolic localization of the $p27^{kip1}$ protein, contributes to the determination of cell morphology and cell-cell adhesion formation.

In addition, when TM4SF5 expression is suppressed using a shRNA against TM4SF5 in Huh7 hepatocarcinoma cells expressing endogenous TM4SF5, HGF-induced cell-cell dissociation is inhibited. Thus, TM4SF5 is considered to induce EMT via a signal transduction pathway.

(2) Loss of Contact Inhibition

The present inventors found the loss of contact-mediated growth inhibition by the TM4SF5-induced EMT in TM4SF5-expressing cells, in which cells cannot recognize neighboring cells upon contact between cells at high density, and thus continue to divide and proliferate.

Contact inhibition of growth means that cells stop dividing when they contact adjacent cells, leading to growth arrest. E-cadherin-induced cell-cell contact has been known to suppress cell proliferation and tumorigenesis. A recent report revealed that during contact inhibition, cells exhibit decreased spreading and subsequently stop growing.

Hence, if cells do not contact each other through the EMT process, or the like, they cannot recognize other adjacent cells and thus continue to divide, thus resulting in the loss of contact inhibition.

Figure 33:
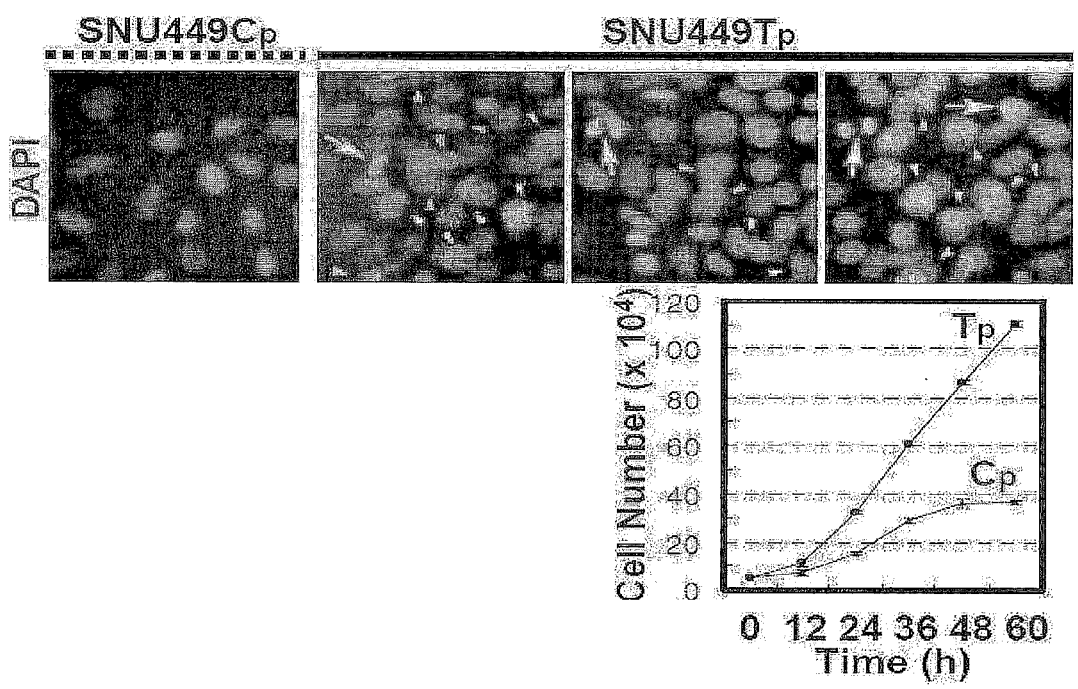
FIG. 33 shows the results of nuclear staining of SNU449 Cp and SNU449Tp cells with DAPI (arrows indicate the overlapping nuclei of cells undergoing cell division), and a graph for the cell number counted every 12 hrs.

Due to their polygonal shape, parental cells not expressing TM4SF5 do not grow any further upon contact inhibition during proliferation with a saturation curve. In contrast, TM4SF5-expressing elongated cells lose intercellular contact and continue to divide even at a density so high that nuclei overlap (FIG. 33).

Figure 35:
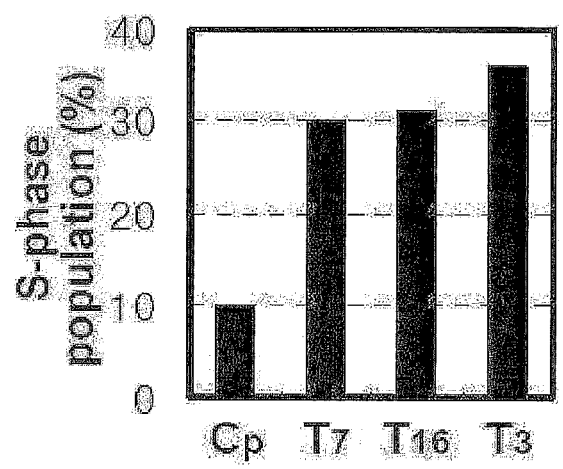
FIG. 35 is a graph showing the S-phase populations of SNU449 Cp cells and TM4SF5-expressing T7, T16 and T3 cells.
Figure 36:
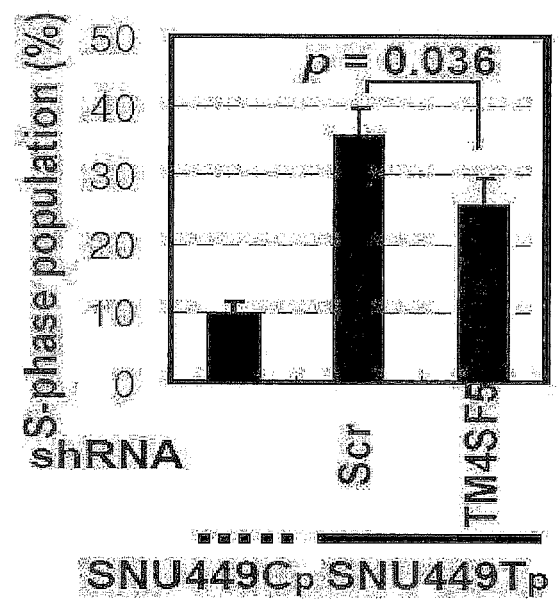
FIG. 36 is a graph showing the S-phase populations of SNU449 Cp cells and SNU449Tp cells, which were transfected with shRNA and shTM4SF5, wherein cell-cycle phase distribution was analyzed using flow cytometry.

Furthermore, TM4SF5-expressing cells exhibit a higher proportion of cell population in the S-phase than that of parental cells (FIG. 35). The suppression of TM4SF5 expression using shRNA reduces the S-phase cell population (FIG. 36).

Figure 57:
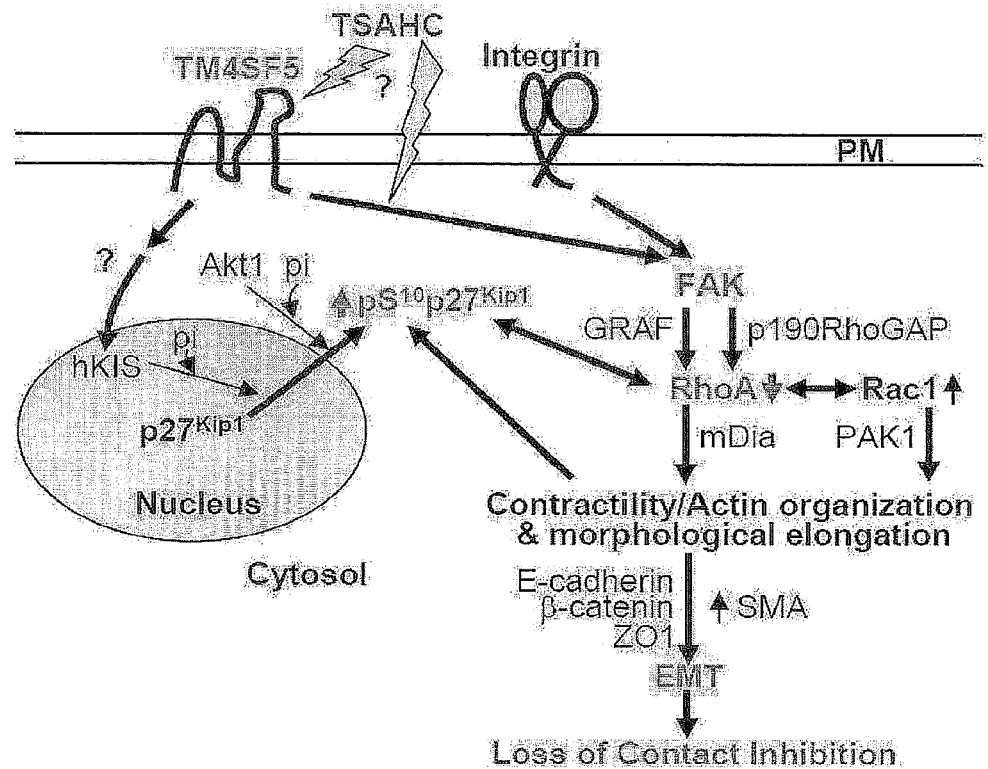
FIG. 57 is a schematic presentation showing the loss of contact inhibition of cell growth due to TM4SF5.

That is, the reduced intercellular contact and EMT induction, mediated by TM4SF5, result in the loss of contact inhibition of cell growth. FIG. 57 schematically represents this process. As shown in FIG. 57, the overexpression of TM4SF5, deemed an oncogene, enhances cytosolic $p27^{kip1}$ expression and stabilization, which are associated with phosphorylation on Ser10 by hKIS or PKB/Akt, and promotes the binding between pY577FAK and FAK/RhoGAPs, leading to reduced activity of RhoA. Rac1 activity is contrary to RhoA inactivation. mDia and PAK function downstream of RhoA and Rac1 to regulate actin dynamics and cell contractility, leading to morphological change. Such morphological change induces the loss of intercellular adhesion, which causes cells not to recognize adjacent cells and to continue to grow, thus resulting in the loss of contact inhibition.

TM4SF5-Mediated Cell Migration, Invasion and Metastasis

As mentioned above, the overexpression of FAK, associated with TM4SF5 expression, or Rac1 activation increases cell motility. Epithelial cell migration, controlled by Rho activity and EMT, plays an important role in physiological processes such as cell shape determination and wound healing, and is essential for chronic inflammation and tumor metastasis.

Figure 58:
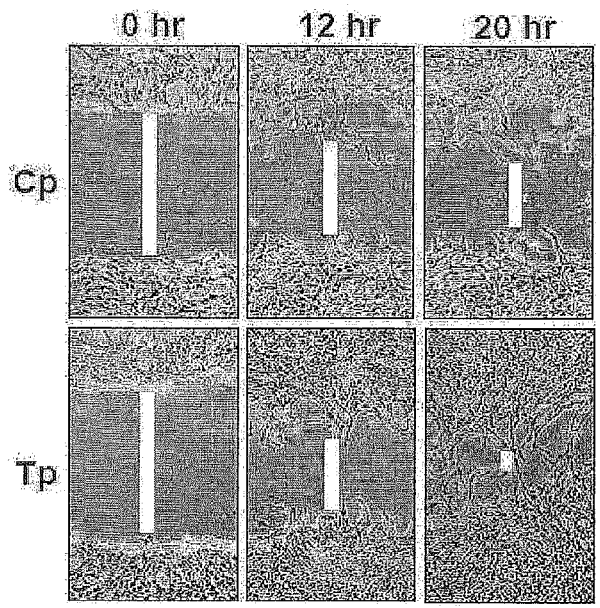
FIG. 58 shows the degree of closure of the wound created in SNU449 Cp and SNU449Tp cells grown to confluence, wherein cells were observed under an optical microscope.
Figure 59:
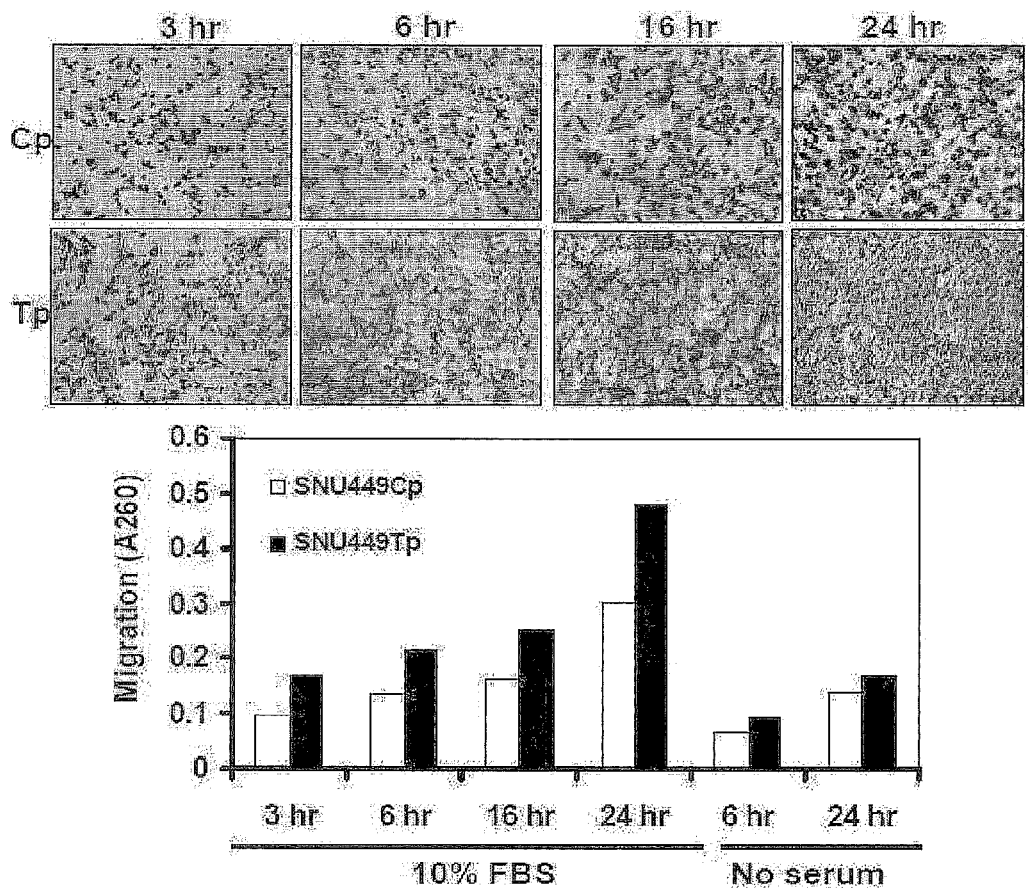
FIG. 59 shows the degree of migration of SNU449 Cp and Tp cells, which were stained with crystal violet and then observed under an optical microscope, and absorbance measured at 260 nm after the dye was dissolved.
Figure 60:
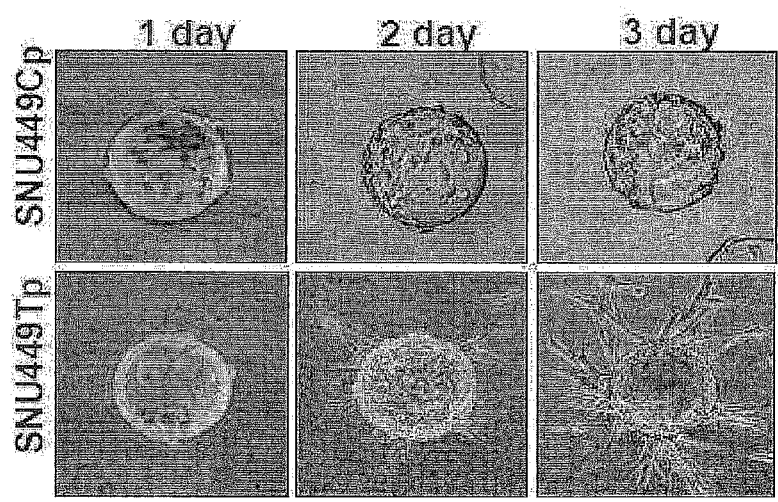
FIG. 60 shows the invasion of SNU449Tp cells into a collagen gel matrix, wherein cells were observed under an optical microscope.
Figure 61:
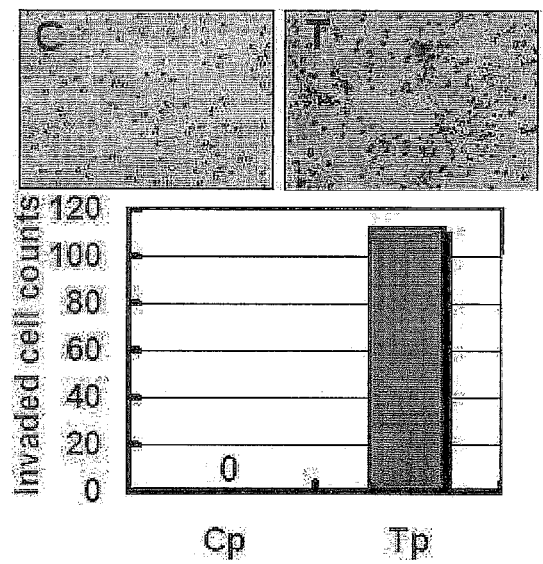
FIG. 61 shows the invasion of SNU449Tp cells into Matrigel, wherein cells were observed under an optical microscope, and the number of invading cells.

Thus, TM4SF5-expressing cells have higher motility than TM4SF5-null cells (FIGS. 58 and 59). Migratory cells are dissociated from adhesion sites and invade the surrounding extracellular matrix (ECM). TM4SF5-expressing cells more effectively invade collagen gels, which form a dense extracellular network, than do TM4SF5-null cells (FIG. 60), and effectively invade Matrigel, which is an extracellular matrix complex (FIG. 61).

Figure 62:
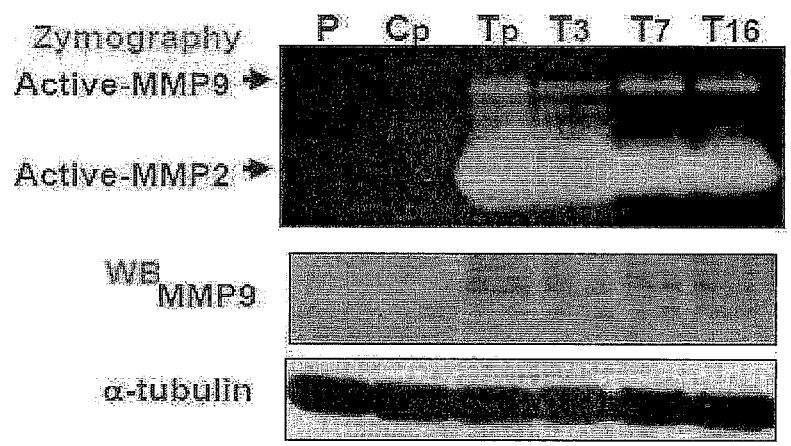
FIG. 62 shows the results of gelatin zymography for the activity of MMPs in SNU449Tp, T3, T7 and T16 cells, and the results of immunoblotting for expression levels of MMP-9 and α-tubulin.

Cell invasion into the ECM is in part driven through degradation of ECM components by matrix metalloproteinases (MMPs). MMPs are a family of $Zn^{2+}$-dependent endopeptidases capable of degrading cellular substrates. Among them, MMP-2 and MMP-9, which degrade gelatin and fibronectin substrates, have high activity in TM4SF5-expressing cells (SNU449Tp, T3, T7, T16, etc.) (FIG. 62). In particular, besides high enzymatic activity, MMP-9 shows high gene expression (middle panel, FIG. 62).

As described in Example 11, employing a nude mouse model for tumor metastasis, tumor cell metastasis, based on the cell motility and invasiveness shown in TM4SF5-expressing cancer cells, was observed in vivo.

Taken together, since TM4SF5 as a tumor inducer causes continuous cell division without suitable growth control in cells in vitro as well as in animal models in vivo, the expression of TM4SF5 in hepatocarcinoma cells or other types of cancer cells induces the increase of focal adhesion kinase (FAK) phosphorylation and cytosolic $p27^{kip1}$ accumulation, leading to the inhibition of RhoA activity, continuous cell growth, accelerated entrance into S-phase, morphological change, and adhesion-independent growth. When a TM4SF5-expressing cell line is injected into a nude mouse (in vivo), tumors are formed.

In this regard, the present inventors developed a method for screening an anticancer compound based on the diverse cell biological and biochemical events induced by the expression of TM4SF5, which functions as a tumor inducer.

As used herein, the term "anticancer" refers to the inhibition or prevention of tumor growth. The concept of inhibiting or preventing tumor growth includes reducing tumor growth and metastasis upon treatment with an anticancer substance in comparison with no treatment. The term "tumor metastasis" refers to a process by which tumor (cancer) cells spread to other parts of the body from the original site. The above terms also include cancers developed through the metastatic process.

The method of the present invention includes culturing cancer cells expressing the polypeptide represented by SEQ ID NO: 2. A representative polynucleotide encoding the polypeptide is the polynucleotide represented by SEQ ID NO: 1.

The cancer cells expressing the polypeptide of SEQ ID NO: 2 are a cell line expressing TM4SF5 protein. In one embodiment, the present method may be practiced by establishing an SNU449 hepatocarinoma cell line (KCLB No. 00449), which stably expresses TM4SF5 in epithelial cells, and culturing the cell line in a medium. Instead of said SNU449 cells, SNU398 cells (KCLB No. 00398) are also available.

Examples of the cancer cells expressing the polypeptide from the nucleotide represented by SEQ ID NO: 1 include pancreatic, gastric, liver, colon, brain or lung cancer cells, or artificially established cancer cells, but any cells expressing the tumorigenic TM4SF5 protein are available. The artificially established cancer cells are exemplified by cells expressing the tumorigenic TM4SF5 protein, established using cloning techniques including gene manipulation.

The present method subsequently includes treating the cultured cancer cells with an anticancer candidate. Preferably, cells are treated with compounds predicted to control events specifically induced by TM4SF5.

Finally, the method includes determining the anticancer candidate to be an anticancer substance when it exhibits at least one of the anticancer functions described below, compared to when treatment with the anticancer candidate is not conducted.

The anticancer functions of the anticancer substance are defined based on the aforementioned diverse cell biological and biochemical events associated with TM4SF5 expression, as follows:

(i) decreased phosphorylation of FAK on Tyr577;
(ii) inhibition of binding of FAK to RhoGAP or PAK to GRAF;
(iii) reduced cytosolic $p27^{Kip1}$ expression and stability
(iv) increased RhoA activity; and
(v) decreased Rac1 activity.

In the method, based on the aforementioned features associated with cell morphology and cell contact patterns according to TM4SF5 expression, the anticancer candidate is determined to be an anticancer substance when it exhibits at least one of the following additional anticancer functions:

(vi) change in cell morphology from a rod shape into a polygonal shape;
(vii) reduced expression of proteins involved in cell adhesion formation;
(viii) maintenance of cell-cell contact;
(ix) contact inhibition of cell growth;
(x) reduced expression of α-smooth muscle actin (α-SMA) or vimentin, or increased expression of E-cadherin; and
(xi) reduced epithelial-mesenchymal transition (EMT).

The proteins involved in cell adhesion formation at (vii) are selected from the group consisting of E-cadherin, zonula occludens-1 (ZO1), catenin and desmoplakin. The contact inhibition of cell growth at (ix) indicates the reduction of cell number, reduction of cell population in S-phase, or inhibition of multilayer growth. That is, contact inhibition means that cells grow in a monolayer and stop proliferating when multilayer proliferation is inhibited and cell contact occurs. Also, the reduction of cell number or reduction of S-phase cell population is mediated through the inactivation of N-linked glycosylation of TM4SF5 and membrane proteins interacting therewith.

Furthermore, based on the aforementioned features associated with increased cell motility and invasiveness, mediated by TM4SF5, the anticancer candidate is determined to be an anticancer substance when it exhibits at least one of the following additional anticancer functions:

(xii) decreased cell migration or motility in the presence of an extracellular matrix or serum;
(xiii) inhibition of invasion into collagen gels which comprise the extracellular matrix;
(xiv) inhibition of invasion into Matrigel which is an extracellular matrix complex; and
(xv) reduction of matrix metalloproteinase (MMP) activity.

Wherein preferable MMPs are MMP-2 or MMP-9.

In other words, the suppression of expression of TM4SF5 as a tumor inducer or an EMT inducer is determined through general events, including the inhibition of FAK phosphorylation or activity change; the inhibition of Rho activity reduction according to cytosolic $p27^{Kip1}$ expression and accumulation; the inhibition of changes in cell morphology according to changes in the activity of Rho GTPase including Rac1 and RhoA; the inhibition of differentiation, epithelial-mesenchymal transition (EMT) or transdifferentiation induction; the inhibition of S-phase progression; the inhibition of multilayer growth or proliferation induced by the loss of contact inhibition; the inhibition of adhesion-independent proliferation or proliferation in soft agar; the inhibition of cell migration and invasion; and the inhibition of tumor formation and metastasis upon injection of oncogene-expressing cells into nude mice.

In another aspect, the present invention relates to anticancer compounds screened for anticancer functions against TM4SF5 using the method. The anticancer functions against TM4SF5 are the same as those described above. Preferably, the anticancer substances are chalcone compounds represented by Chemical Formula 1 or 2.

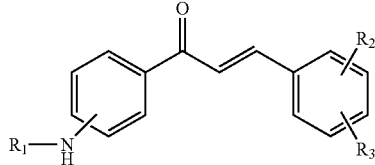

[Chemical Formula 1]

wherein, $R_1$ represents $R_4SO_2$—; $R_2$ and $R_3$ are independently hydrogen or hydroxy; and $R_4$ is $(C_1-C_5)$ alkyl or $(C_6-C_{10})$ aryl having one or more substituents selected from the group consisting of hydrogen, halogen, nitro and $(C_1-C_5)$ alkyl, preferably methyl, benzyl, ρ-toluoyl, ρ-nitrophenyl or ρ-fluorophenyl.

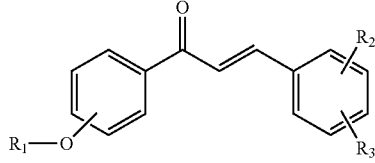

[Chemical Formula 2]

wherein, $R_1$ represents $R_4SO_2$—; $R_2$ and $R_3$ are independently hydrogen or hydroxy; and $R_4$ is $(C_1-C_5)$ alkyl or is $(C_6-C_{10})$ aryl having one or more substituents selected from the group consisting of hydrogen, halogen, nitro and $(C_1-C_5)$ alkyl, preferably methyl, benzyl, ρ-toluoyl, ρ-nitrophenyl or ρ-fluorophenyl.

More preferably, the anticancer substances of the present invention are chalcone compounds listed in Table 1, below. A representative anticancer compound is TSAHC [4'-(ρ-toluenesulfonylamino)-4-hydroxy chalcone], described in Table 1.

TABLE 1

| Compounds | Structure |
|---|---|
| 1 | 4-methyl-N-(4-((E)-3-(4-hydroxyphenyl)acryloyl)phenyl)benzenesulfonamide |
| 2 | 4-methyl-N-(4-((E)-3-(3-hydroxyphenyl)acryloyl)phenyl)benzenesulfonamide |
| 3 | 4-methyl-N-(4-((E)-3-(2-hydroxyphenyl)acryloyl)phenyl)benzenesulfonamide |
| 4 | 4-methyl-N-(3-((E)-3-(4-hydroxyphenyl)acryloyl)phenyl)benzenesulfonamide |
| 5 | 4-methyl-N-(2-((E)-3-(4-hydroxyphenyl)acryloyl)phenyl)benzenesulfonamide |
| 6 | 4-hydroxy-N-(4-((E)-3-(4-hydroxyphenyl)acryloyl)phenyl)benzenesulfonamide |
| 7 | 4-hydroxy-N-(4-((E)-3-(3-hydroxyphenyl)acryloyl)phenyl)benzenesulfonamide |
| 8 | 4-hydroxy-N-(4-((E)-3-(2-hydroxyphenyl)acryloyl)phenyl)benzenesulfonamide |

TABLE 1-continued

| Compounds | Structure |
|---|---|
| 9 | 4-hydroxyphenylsulfonamide linked to 3-aminophenyl chalcone with 4-hydroxyphenyl group |
| 10 | 4-hydroxyphenylsulfonamide linked to 3-aminophenyl chalcone with 3-hydroxyphenyl group |
| 11 | 4-hydroxyphenylsulfonamide linked to 3-aminophenyl chalcone with 2-hydroxyphenyl group |
| 12 | 4-hydroxyphenylsulfonamide linked to 2-aminophenyl chalcone with 4-hydroxyphenyl group |
| 13 | 4-hydroxyphenylsulfonamide linked to 2-aminophenyl chalcone with 3-hydroxyphenyl group |
| 14 | 4-hydroxyphenylsulfonamide linked to 2-aminophenyl chalcone with 2-hydroxyphenyl group |
| 15 | 3-hydroxyphenylsulfonamide linked to 4-aminophenyl chalcone with 4-hydroxyphenyl group |
| 16 | 3-hydroxyphenylsulfonamide linked to 4-aminophenyl chalcone with 3-hydroxyphenyl group |

TABLE 1-continued
| Compounds | Structure |
|---|---|
| 17 | 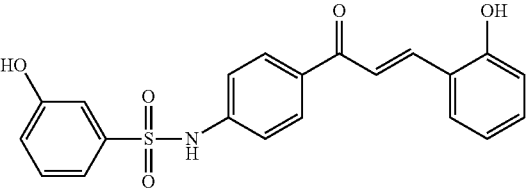 [SMILES: O=C(/C=C/c1ccccc1O)c1ccc(NS(=O)(=O)c2cccc(O)c2)cc1] |
| 18 | 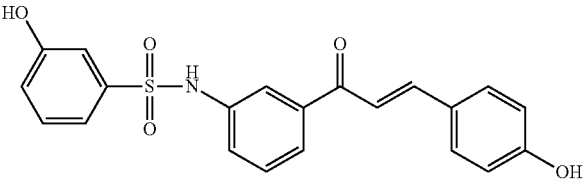 [SMILES: O=C(/C=C/c1ccc(O)cc1)c1cccc(NS(=O)(=O)c2cccc(O)c2)c1] |
| 19 | 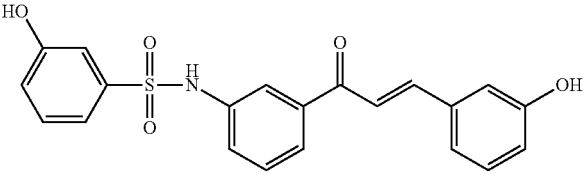 [SMILES: O=C(/C=C/c1cccc(O)c1)c1cccc(NS(=O)(=O)c2cccc(O)c2)c1] |
| 20 | 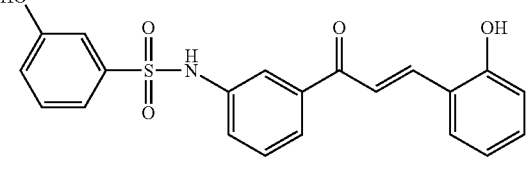 |
| 21 | 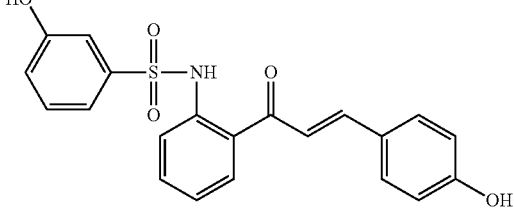 |
| 22 | 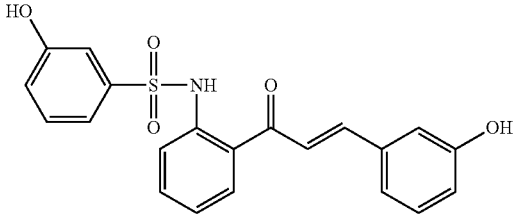 [SMILES: O=C(/C=C/c1cccc(O)c1)c1ccccc1NS(=O)(=O)c1cccc(O)c1] |
| 23 | 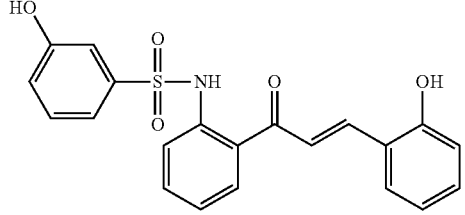 [SMILES: O=C(/C=C/c1ccccc1O)c1ccccc1NS(=O)(=O)c1cccc(O)c1] |

TABLE 1-continued

| Compounds | Structure |
|---|---|
| 24 | 4-F-C6H4-SO2-NH-C6H4-C(O)-CH=CH-C6H4-OH |
| 25 | 3-F-C6H4-SO2-NH-C6H4-C(O)-CH=CH-C6H4-OH |
| 26 | 2-F-C6H4-SO2-NH-C6H4-C(O)-CH=CH-C6H4-OH |
| 27 | 4-O2N-C6H4-SO2-NH-C6H4-C(O)-CH=CH-C6H4-OH |
| 28 | 3-O2N-C6H4-SO2-NH-C6H4-C(O)-CH=CH-C6H4-OH |
| 29 | 2-O2N-C6H4-SO2-NH-C6H4-C(O)-CH=CH-C6H4-OH |
| 30 | 4-H2N-C6H4-SO2-NH-C6H4-C(O)-CH=CH-C6H4-OH |

TABLE 1-continued
| Compounds | Structure |
|---|---|
| 31 | 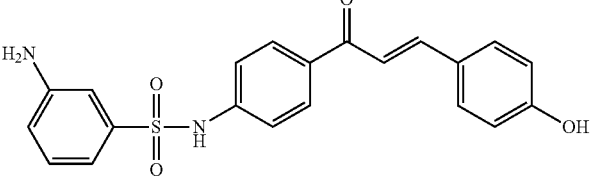 |
| 32 | 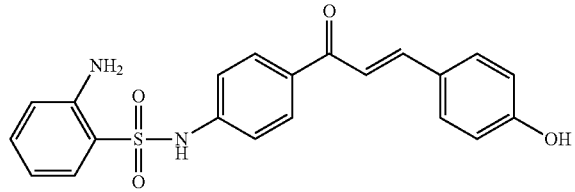 [SMILES: Nc1ccccc1S(=O)(=O)Nc1ccc(C(=O)/C=C/c2ccc(O)cc2)cc1] |
| 33 | 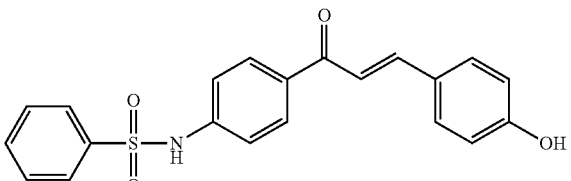 |
| 34 | 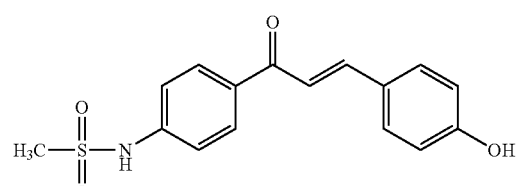 |
| 35 | 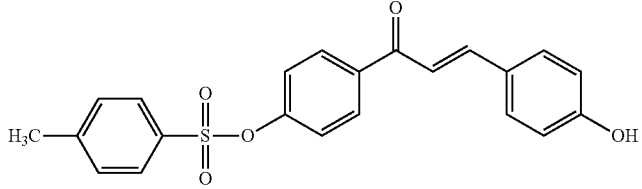 |
| 36 | 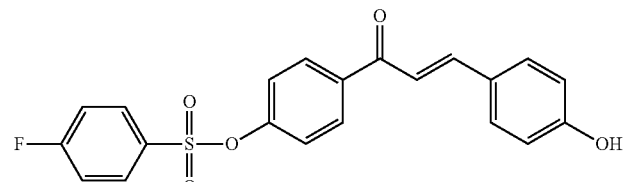 |
| 37 | 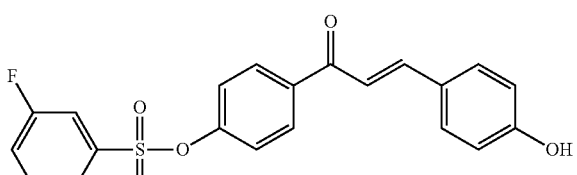 |

TABLE 1-continued
| Compounds | Structure |
|---|---|
| 38 | 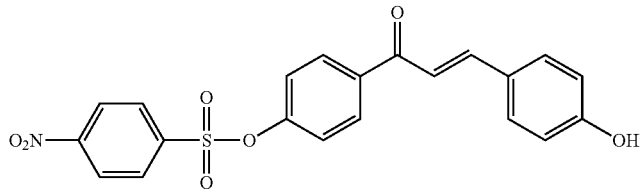 [SMILES: Cc1ccc(S(=O)(=O)Oc2ccc(C(=O)/C=C/c3ccc(O)cc3)cc2)cc1] |
| 39 | 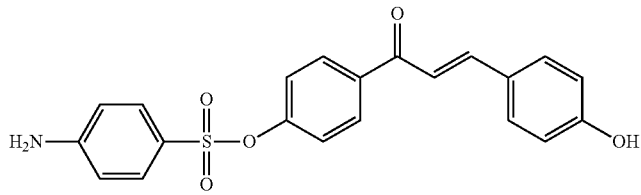 |
| 40 | 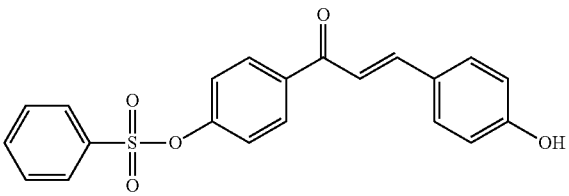 [SMILES: O=C(/C=C/c1ccc(O)cc1)c1ccc(OS(=O)(=O)c2ccccc2)cc1] |
| 41 | 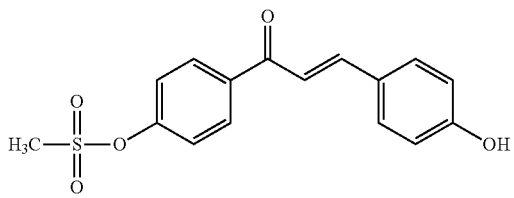 [SMILES: CS(=O)(=O)Oc1ccc(C(=O)/C=C/c2ccc(O)cc2)cc1] |
| 42 | 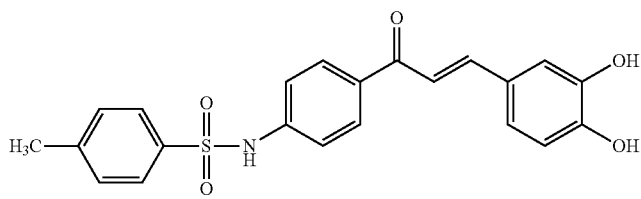 |
| 43 | 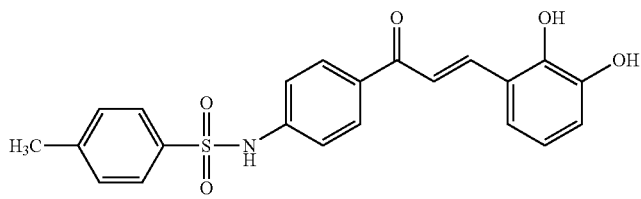 [SMILES: Cc1ccc(S(=O)(=O)Nc2ccc(C(=O)/C=C/c3cccc(O)c3O)cc2)cc1] |
| 44 | 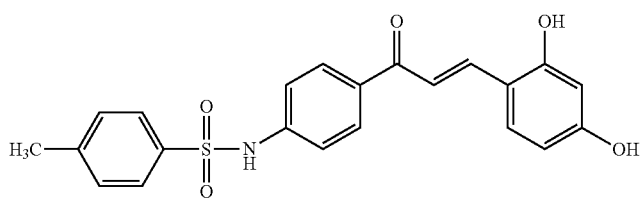 [SMILES: Cc1ccc(S(=O)(=O)Nc2ccc(C(=O)/C=C/c3ccc(O)cc3O)cc2)cc1] |

TABLE 1-continued

| Compounds | Structure |
|---|---|
| 45 | 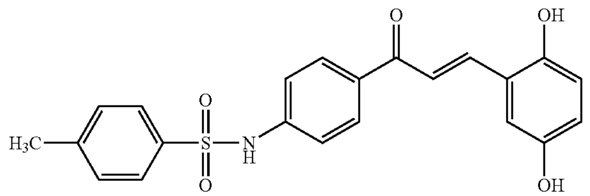 [SMILES: Cc1ccc(S(=O)(=O)Nc2ccc(C(=O)/C=C/c3cc(O)ccc3O)cc2)cc1] |
| 46 | 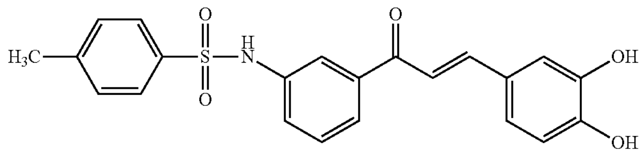 [SMILES: Cc1ccc(S(=O)(=O)Nc2cccc(C(=O)/C=C/c3ccc(O)c(O)c3)c2)cc1] |
| 47 | 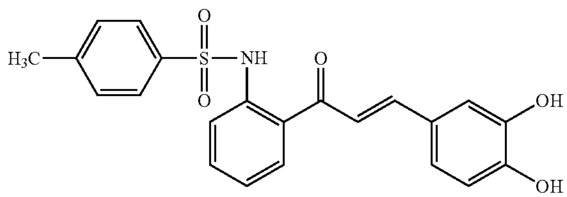 [SMILES: Cc1ccc(S(=O)(=O)Nc2ccccc2C(=O)/C=C/c2ccc(O)c(O)c2)cc1] |
| 48 | 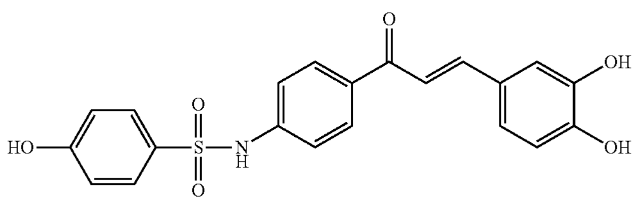 |
| 49 | 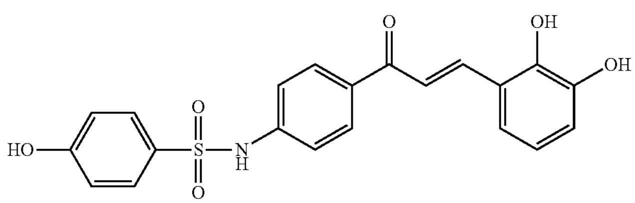 [SMILES: O=C(/C=C/c1cccc(O)c1O)c1ccc(NS(=O)(=O)c2ccc(O)cc2)cc1] |
| 50 | 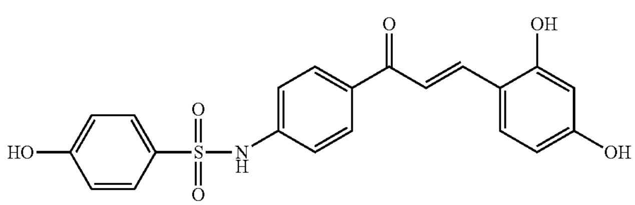 [SMILES: O=C(/C=C/c1ccc(O)cc1O)c1ccc(NS(=O)(=O)c2ccc(O)cc2)cc1] |
| 51 | 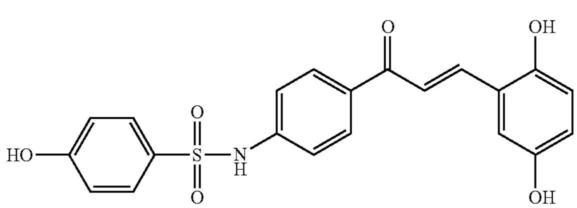 [SMILES: O=C(/C=C/c1cc(O)ccc1O)c1ccc(NS(=O)(=O)c2ccc(O)cc2)cc1] |
| 52 | 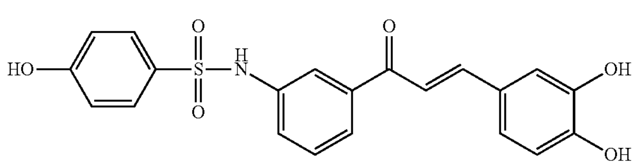 [SMILES: O=C(/C=C/c1ccc(O)c(O)c1)c1cccc(NS(=O)(=O)c2ccc(O)cc2)c1] |

TABLE 1-continued

| Compounds | Structure |
| --- | --- |
| 53 | 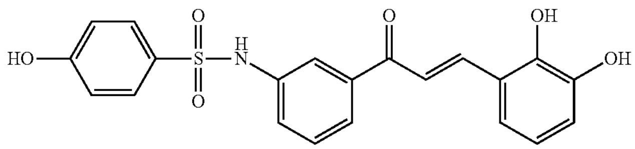 [SMILES: O=C(/C=C/c1cccc(O)c1O)c1cccc(NS(=O)(=O)c2ccc(O)cc2)c1] |
| 54 | 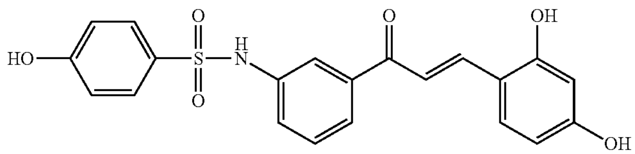 [SMILES: O=C(/C=C/c1ccc(O)cc1O)c1cccc(NS(=O)(=O)c2ccc(O)cc2)c1] |
| 55 | 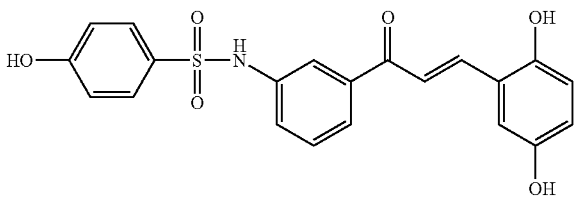 [SMILES: O=C(/C=C/c1cc(O)ccc1O)c1cccc(NS(=O)(=O)c2ccc(O)cc2)c1] |
| 56 | 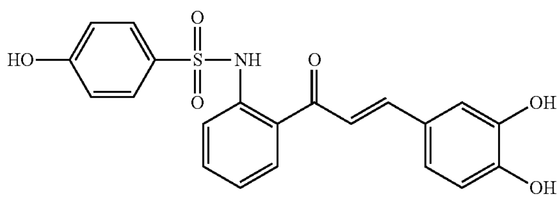 [SMILES: O=C(/C=C/c1ccc(O)c(O)c1)c1ccccc1NS(=O)(=O)c1ccc(O)cc1] |
| 57 | 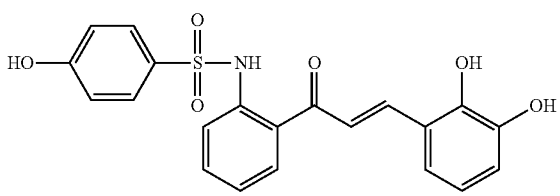 [SMILES: O=C(/C=C/c1cccc(O)c1O)c1ccccc1NS(=O)(=O)c1ccc(O)cc1] |
| 58 | 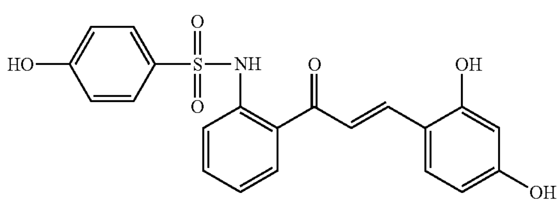 [SMILES: O=C(/C=C/c1ccc(O)cc1O)c1ccccc1NS(=O)(=O)c1ccc(O)cc1] |
| 59 | 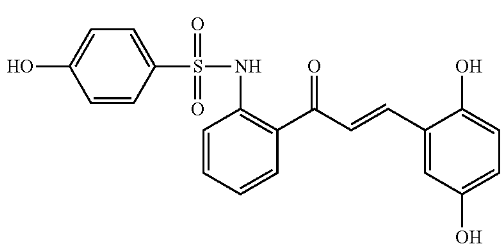 [SMILES: O=C(/C=C/c1cc(O)ccc1O)c1ccccc1NS(=O)(=O)c1ccc(O)cc1] |
| 60 | 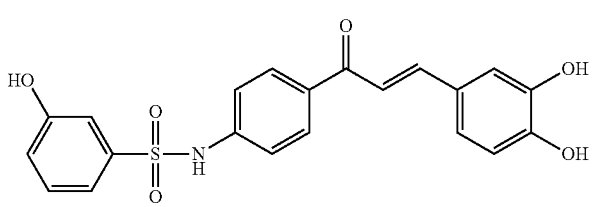 [SMILES: O=C(/C=C/c1ccc(O)c(O)c1)c1ccc(NS(=O)(=O)c2cccc(O)c2)cc1] |

TABLE 1-continued

| Compounds | Structure |
|---|---|
| 61 | 3-hydroxy-N-(4-(3-(2,3-dihydroxyphenyl)acryloyl)phenyl)benzenesulfonamide |
| 62 | 3-hydroxy-N-(4-(3-(2,4-dihydroxyphenyl)acryloyl)phenyl)benzenesulfonamide |
| 63 | 3-hydroxy-N-(4-(3-(2,5-dihydroxyphenyl)acryloyl)phenyl)benzenesulfonamide |
| 64 | 3-hydroxy-N-(3-(3-(3,4-dihydroxyphenyl)acryloyl)phenyl)benzenesulfonamide |
| 65 | 3-hydroxy-N-(3-(3-(2,3-dihydroxyphenyl)acryloyl)phenyl)benzenesulfonamide |
| 66 | 3-hydroxy-N-(3-(3-(2,4-dihydroxyphenyl)acryloyl)phenyl)benzenesulfonamide |
| 67 | 3-hydroxy-N-(3-(3-(2,5-dihydroxyphenyl)acryloyl)phenyl)benzenesulfonamide |

TABLE 1-continued
| Compounds | Structure |
|---|---|
| 68 | 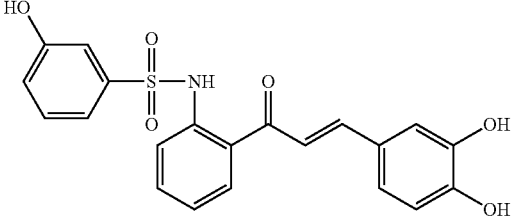 [SMILES: O=C(/C=C/c1ccc(O)c(O)c1)c1ccccc1NS(=O)(=O)c1cccc(O)c1] |
| 69 | 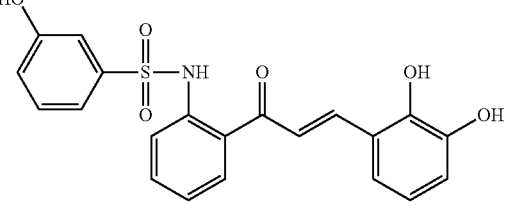 |
| 70 | 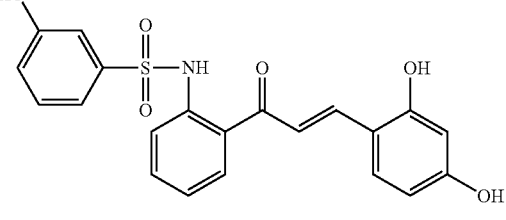 |
| 71 | 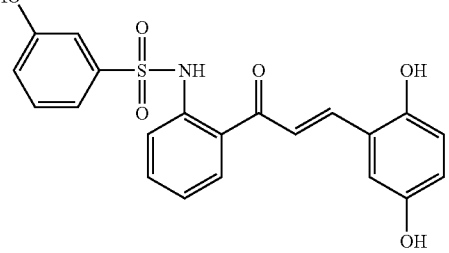 |
| 72 | 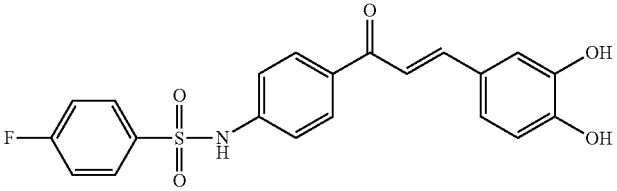 [SMILES: O=C(/C=C/c1ccc(O)c(O)c1)c1ccc(NS(=O)(=O)c2ccc(F)cc2)cc1] |
| 73 | 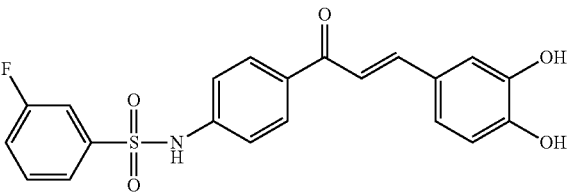 [SMILES: O=C(/C=C/c1ccc(O)c(O)c1)c1ccc(NS(=O)(=O)c2cccc(F)c2)cc1] |
| 74 | 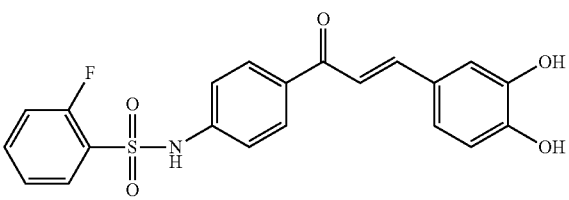 [SMILES: O=C(/C=C/c1ccc(O)c(O)c1)c1ccc(NS(=O)(=O)c2ccccc2F)cc1] |

TABLE 1-continued
| Compounds | Structure |
|---|---|
| 75 | 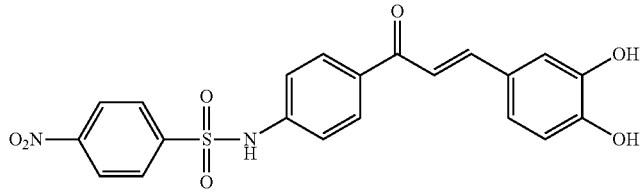 [SMILES: O=C(/C=C/c1ccc(O)c(O)c1)c1ccc(NS(=O)(=O)c2ccc([N+](=O)[O-])cc2)cc1] |
| 76 | 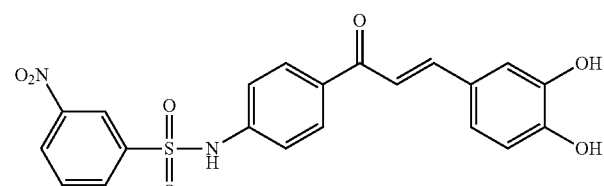 |
| 77 | 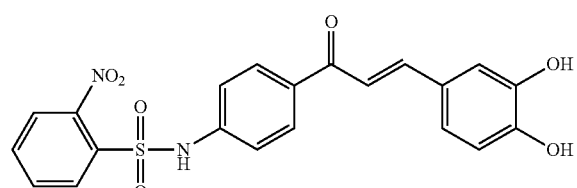 |
| 78 | 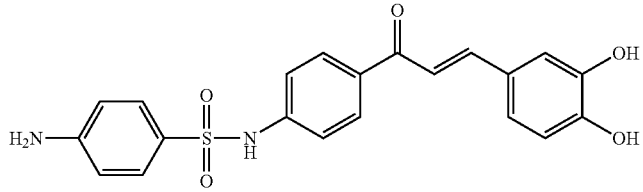 |
| 79 | 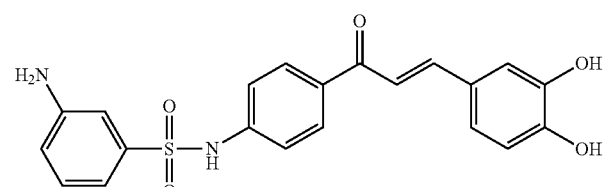 |
| 80 | 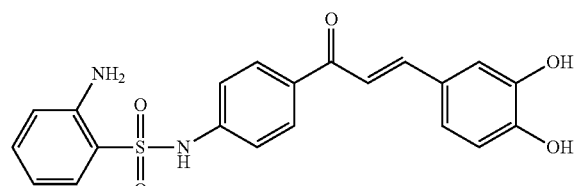 |
| 81 | 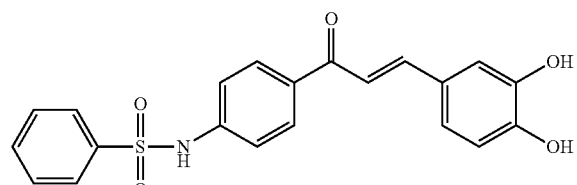 |

TABLE 1-continued

| Compounds | Structure |
|---|---|
| 82 | 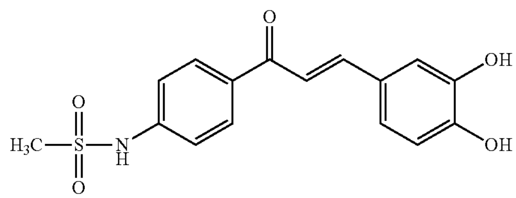 [SMILES: CS(=O)(=O)Nc1ccc(C(=O)/C=C/c2ccc(O)c(O)c2)cc1] |
| 83 | 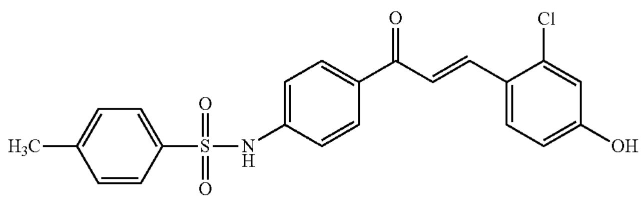 [SMILES: Cc1ccc(S(=O)(=O)Nc2ccc(C(=O)/C=C/c3ccc(O)cc3Cl)cc2)cc1] |
| 84 | 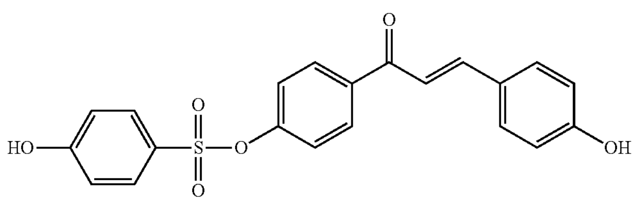 [SMILES: O=C(/C=C/c1ccc(O)cc1)c1ccc(OS(=O)(=O)c2ccc(O)cc2)cc1] |
| 85 | 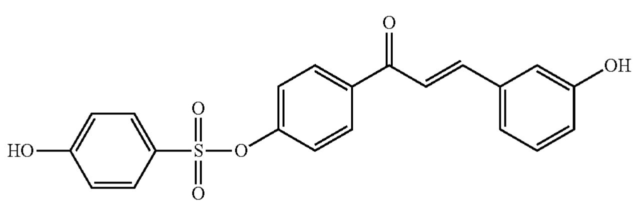 [SMILES: O=C(/C=C/c1cccc(O)c1)c1ccc(OS(=O)(=O)c2ccc(O)cc2)cc1] |
| 86 | 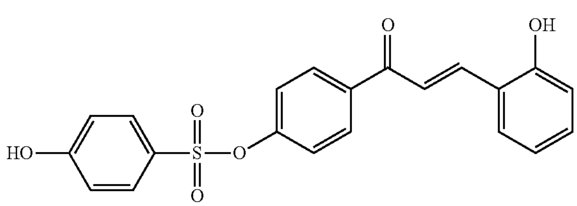 [SMILES: O=C(/C=C/c1ccccc1O)c1ccc(OS(=O)(=O)c2ccc(O)cc2)cc1] |
| 87 | 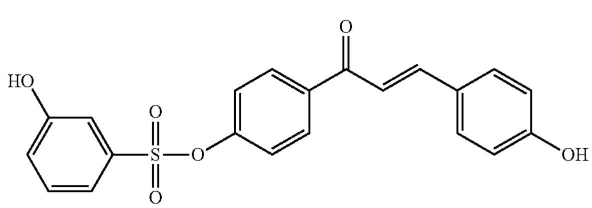 |
| 88 | 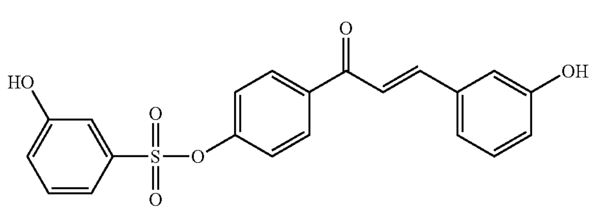 |

TABLE 1-continued

| Compounds | Structure |
|---|---|
| 89 | 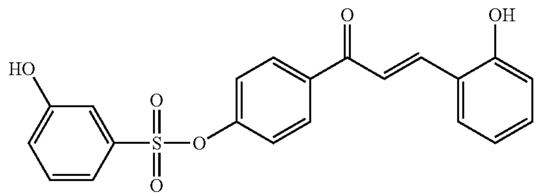 [SMILES: O=C(/C=C/c1ccccc1O)c1ccc(OS(=O)(=O)c2cccc(O)c2)cc1] |
| 90 | 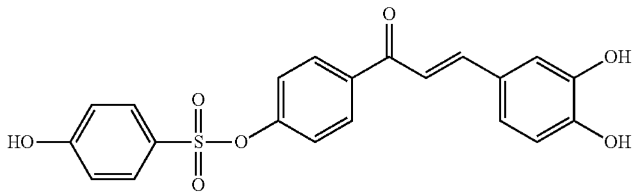 [SMILES: O=C(/C=C/c1ccc(O)c(O)c1)c1ccc(OS(=O)(=O)c2ccc(O)cc2)cc1] |
| 91 | 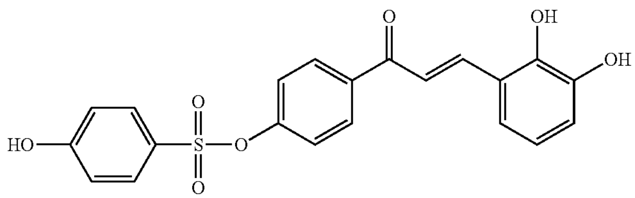 [SMILES: O=C(/C=C/c1cccc(O)c1O)c1ccc(OS(=O)(=O)c2ccc(O)cc2)cc1] |
| 92 | 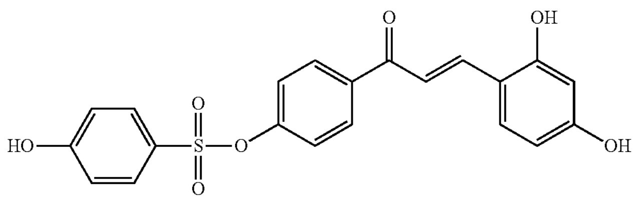 [SMILES: O=C(/C=C/c1ccc(O)cc1O)c1ccc(OS(=O)(=O)c2ccc(O)cc2)cc1] |
| 93 | 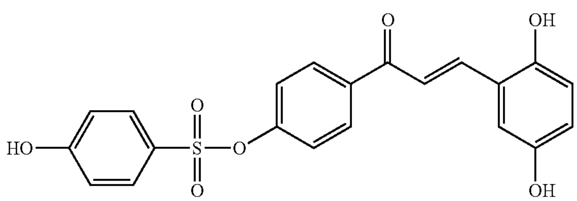 [SMILES: O=C(/C=C/c1cc(O)ccc1O)c1ccc(OS(=O)(=O)c2ccc(O)cc2)cc1] |
| 94 | 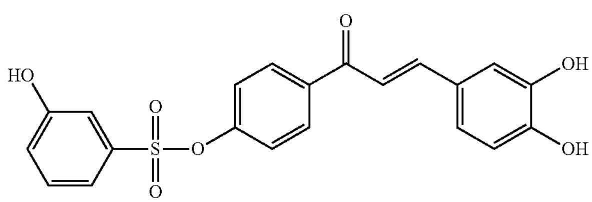 [SMILES: O=C(/C=C/c1ccc(O)c(O)c1)c1ccc(OS(=O)(=O)c2cccc(O)c2)cc1] |
| 95 | 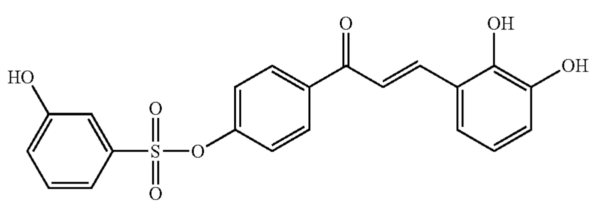 [SMILES: O=C(/C=C/c1cccc(O)c1O)c1ccc(OS(=O)(=O)c2cccc(O)c2)cc1] |
| 96 | 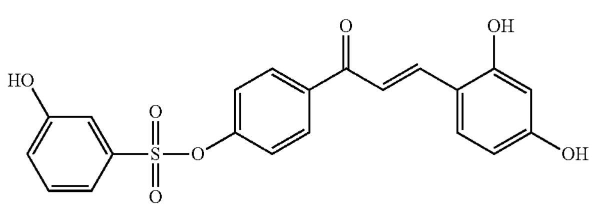 [SMILES: O=C(/C=C/c1ccc(O)cc1O)c1ccc(OS(=O)(=O)c2cccc(O)c2)cc1] |

TABLE 1-continued

| Compounds | Structure |
|---|---|
| 97 | (structure shown) |

The chalcone compounds 1 to 97, described in Table 1, have the properties described below:

4'-(p-toluenesulfonylamino)-4-hydroxychalcone;
4'-(p-toluenesulfonylamino)-3-hydroxychalcone;
4'-(p-toluenesulfonylamino)-2-hydroxychalcone;
3'-(p-toluenesulfonylamino)-4-hydroxychalcone,
2'-(p-toluenesulfonylamino)-4-hydroxychalcone;
4'-(p-hydroxybenzenesulfonylamino)-4-hydroxychalcone;
4'-(p-hydroxybenzenesulfonylamino)-3-hydroxychalcone;
4'-(p-hydroxybenzenesulfonylamino)-2-hydroxychalcone;
3'-(p-hydroxybenzenesulfonylamino)-4-hydroxychalcone;
3'-(p-hydroxybenzenesulfonylamino)-3-hydroxychalcone;
3'-(p-hydroxybenzenesulfonylamino)-2-hydroxychalcone;
2'-(p-hydroxybenzenesulfonylamino)-4-hydroxychalcone;
2'-(p-hydroxybenzenesulfonylamino)-3-hydroxychalcone;
2'-(p-hydroxybenzenesulfonylamino)-2-hydroxychalcone;
4'-(m-hydroxybenzenesulfonylamino)-4-hydroxychalcone;
4'-(m-hydroxybenzenesulfonylamino)-3-hydroxychalcone;
4'-(m-hydroxybenzenesulfonylamino)-2-hydroxychalcone;
3'-(m-hydroxybenzenesulfonylamino)-4-hydroxychalcone;
3'-(m-hydroxybenzenesulfonylamino)-3-hydroxychalcone;
3'-(m-hydroxybenzenesulfonylamino)-2-hydroxychalcone;
2'-(m-hydroxybenzenesulfonylamino)-4-hydroxychalcone;
2'-(m-hydroxybenzenesulfonylamino)-3-hydroxychalcone;
2'-(m-hydroxybenzenesulfonylamino)-2-hydroxychalcone;
4'-(p-fluorobenzensulfonylamino)-4-hydroxychalcone;
4'-(m-fluorobenzensulfonylamino)-4-hydroxychalcone;
4'-(o-fluorobenzensulfonylamino)-4-hydroxychalcone;
4'-(p-nitrobenzensulfonylamino)-4-hydroxychalcone;
4'-(m-nitrobenzensulfonylamino)-4-hydroxychalcone;
4'-(o-nitrobenzensulfonylamino)-4-hydroxychalcone;
4'-(p-aminobenzensulfonylamino)-4-hydroxychalcone;
4'-(m-aminobenzensulfonylamino)-4-hydroxychalcone;
4'-(o-aminobenzensulfonylamino)-4-hydroxychalcone;
4'-(benzensulfonylamino)-4-hydroxychalcone;
4'-(methanesulfonylamino)-4-hydroxychalcone;
4'-(p-toluenesulfonate)-4-hydroxychalcone;
4'-(p-fluorobenzenesulfonate)-4-hydroxychalcone;
4'-(m-fluorobenzenesulfonate)-4-hydroxychalcone;
4'-(p-nitrobenzenesulfonate)-4-hydroxychalcone, 4'-(p-aminobenzenesulfonate)-4-hydroxychalcone;
4'-(benzenesulfonate)-4-hydroxychalcone;
4'-(methanesulfonate)-4-hydroxychalcone;
4'-(p-toluenesulfonylamino)-3,4-dihydroxychalcone;
4'-(p-toluenesulfonylamino)-2,3-dihydroxychalcone;
4'-(p-toluenesulfonylamino)-2,4-dihydroxychalcone;
4'-(p-toluenesulfonylamino)-2,5-dihydroxychalcone;
3'-(p-toluenesulfonylamino)-3,4-dihydroxychalcone;
2'-(p-toluenesulfonylamino)-3,4-dihydroxychalcone;
4'-(p-hydroxybenzenesulfonylamino)-3,4-dihydroxychalcone;
4'-(p-hydroxybenzenesulfonylamino)-2,3-dihydroxychalcone;
4'-(p-hydroxybenzenesulfonylamino)-2,4-dihydroxychalcone;
4'-(p-hydroxybenzenesulfonylamino)-2,5-dihydroxychalcone;
3'-(p-hydroxybenzenesulfonylamino)-3,4-dihydroxychalcone;
3'-(p-hydroxybenzenesulfonylamino)-2,3-dihydroxychalcone;
3'-(p-hydroxybenzenesulfonylamino)-2,4-dihydroxychalcone;
3'-(p-hydroxybenzenesulfonylamino)-2,5-dihydroxychalcone;
2'-(p-hydroxybenzenesulfonylamino)-3,4-dihydroxychalcone;
2'-(p-hydroxybenzenesulfonylamino)-2,3-dihydroxychalcone;
2'-(p-hydroxybenzenesulfonylamino)-2,4-dihydroxychalcone;
2'-(p-hydroxybenzenesulfonylamino)-2,5-dihydroxychalcone;
4'-(m-hydroxybenzenesulfonylamino)-3,4-dihydroxychalcone;
4'-(m-hydroxybenzenesulfonylamino)-2,3-dihydroxychalcone;
4'-(m-hydroxybenzenesulfonylamino)-2,4-dihydroxychalcone;
4'-(m-hydroxybenzenesulfonylamino)-2,5-dihydroxychalcone;
3'-(m-hydroxybenzenesulfonylamino)-3,4-dihydroxychalcone;
3'-(m-hydroxybenzenesulfonylamino)-2,3-dihydroxychalcone;
3'-(m-hydroxybenzenesulfonylamino)-2,4-dihydroxychalcone;
3'-(m-hydroxybenzenesulfonylamino)-2,5-dihydroxychalcone;
2'-(m-hydroxybenzenesulfonylamino)-3,4-dihydroxychalcone;
2'-(m-hydroxybenzenesulfonylamino)-2,3-dihydroxychalcone;
2'-(m-hydroxybenzenesulfonylamino)-2,4-dihydroxychalcone;
2'-(m-hydroxybenzenesulfonylamino)-2,5-dihydroxychalcone;
4'-(p-fluorobenzensulfonylamino)-3,4-dihydroxychalcone;
4'-(m-fluorobenzensulfonylamino)-3,4-dihydroxychalcone;
4'-(o-fluorobenzensulfonylamino)-3,4-dihydroxychalcone;
4'-(p-nitrobenzensulfonylamino)-3,4-dihydroxychalcone;
4'-(m-nitrobenzensulfonylamino)-3,4-dihydroxychalcone;
4'-(o-nitrobenzensulfonylamino)-3,4-dihydroxychalcone;
4'-(p-aminobenzensulfonylamino)-3,4-dihydroxychalcone;
4'-(m-aminobenzensulfonylamino)-3,4-dihydroxychalcone;
4'-(o-aminobenzensulfonylamino)-3,4-dihydroxychalcone;

4'-(benzensulfonylamino)-3,4-dihydroxychalcone;
4'-(methanesulfonylamino)-3,4-dihydroxychalcone;
4'-(p-toluenebenzensulfonylamino)-2-chloro-4-hydroxychalcone;
4'-(p-hydroxybenzenesulfonate)-4-hydroxychalcone;
4'-(p-hydroxybenzenesulfonate)-3-hydroxychalcone;
4'-(p-hydroxybenzenesulfonate)-2-hydroxychalcone;
4'-(m-hydroxybenzenesulfonate)-4-hydroxychalcone;
4'-(m-hydroxybenzenesulfonate)-3-hydroxychalcone;
4'-(m-hydroxybenzenesulfonate)-2-hydroxychalcone;
4'-(p-hydroxybenzenesulfonate)-3,4-dihydroxychalcone;
4'-(p-hydroxybenzenesulfonate)-2,3-dihydroxychalcone;
4'-(p-hydroxybenzenesulfonate)-2,4-dihydroxychalcone;
4'-(p-hydroxybenzenesulfonate)-2,5-dihydroxychalcone;
4'-(m-hydroxybenzenesulfonate)-3,4-dihydroxychalcone;
4'-(m-hydroxybenzenesulfonate)-2,3-dihydroxychalcone;
4'-(m-hydroxybenzenesulfonate)-2,4-dihydroxychalcone; and
4'-(m-hydroxybenzenesulfonate)-2,5-dihydroxychalcone.

Korean Patent Publication 10-2003-0036993 discloses that chalcone compounds have inhibitory activity against matrix metalloproteinase (MMP), which degrades components of the basement membrane. However, the patent publication does not suggest the anticancer functions of chalcone compounds. In addition, the present invention is characterized in that the chalcone compounds represented by Chemical Formula 1 or 2 contain a sulfonyl ($SO_3$—) or sulfonamide ($SO_2NH$—) group. That is, the anticancer activity (function) against TM4SF5 of the chalcone compounds of the present invention is based on the sulfonyl group ($SO_3$—).

In particular, in Example 12, when a chalcone compound had OH, $NH_2$ or $OCH_3$ as a substituent on the A-ring (left ring), the compound did not display anticancer activity to inhibit the TM4SF5-mediated multilayer growth. In contrast, when a sulfonyl group was introduced into a chalcone compound according to the present invention, a sulfonamide or sulfonate chalcone compound exhibited anticancer activity, thus inhibiting the TM4SF5 function. That is, the introduction of a sulfonyl group into a chalcone compound confers unique anticancer activity, which is distinct from that of known chalcone derivatives.

The representative compound TSAHC [4'-(p-toluenesulfonylamino)-4-hydroxy chalcone] (Compound 1, Table 1) was evaluated for its anticancer functions in the present examples.

Figure 44:
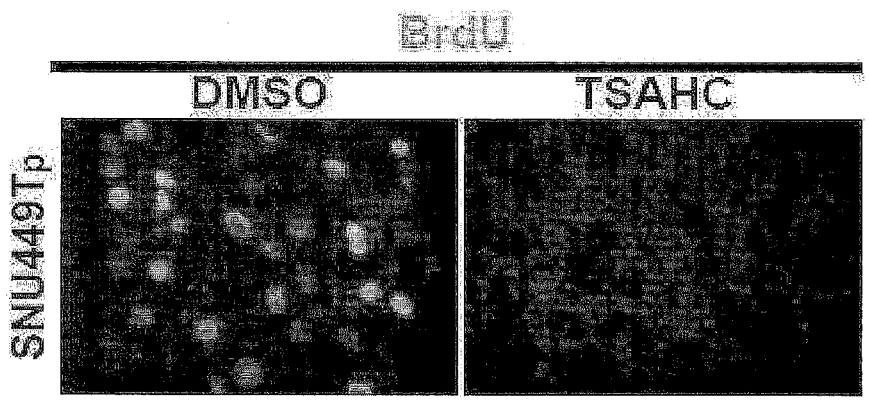
FIG. 44 shows the results of immunofluorescent staining of SNU449Tp cells, which were treated with DMSO or 20 μM of TSAHC and then with BrdU for 24 hrs.
Figure 45:
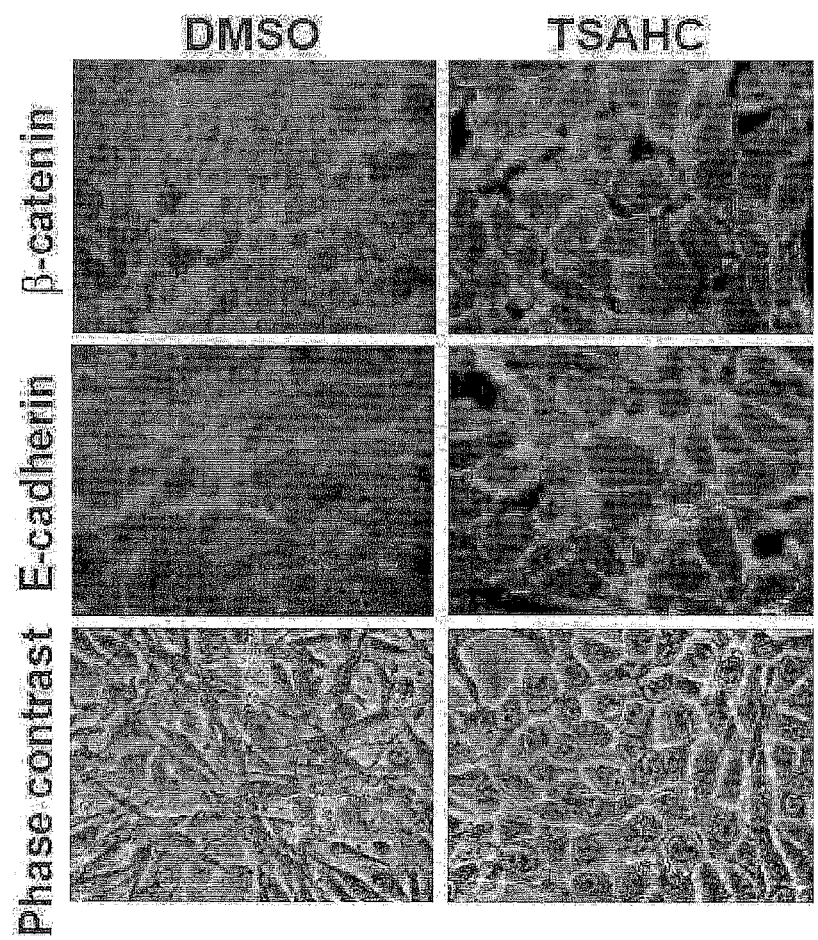
FIG. 45 shows the results of immunofluorescent staining for E-cadherin and β-catenin of SNU449Tp cells, which were treated with DMSO or 20 μM of TSAHC.

The chalcone compounds according to the present invention function as antagonists specifically inhibiting TM4SF5-mediated events. The treatment of TM4SF5-expressing cells with one or more selected from among the chalcone compounds including TSAHC decreases continuous growth over time in a manner dependent on the concentration of chalcone compounds (right graph, FIG. 43), inhibits entrance into S phase (FIG. 44), and restores cell-cell contact (FIG. 45). In contrast, the anticancer effects of the chalcone compounds according to the present invention were not shown in TM4SF5-null cells (left graph, FIG. 43).

Figure 47:
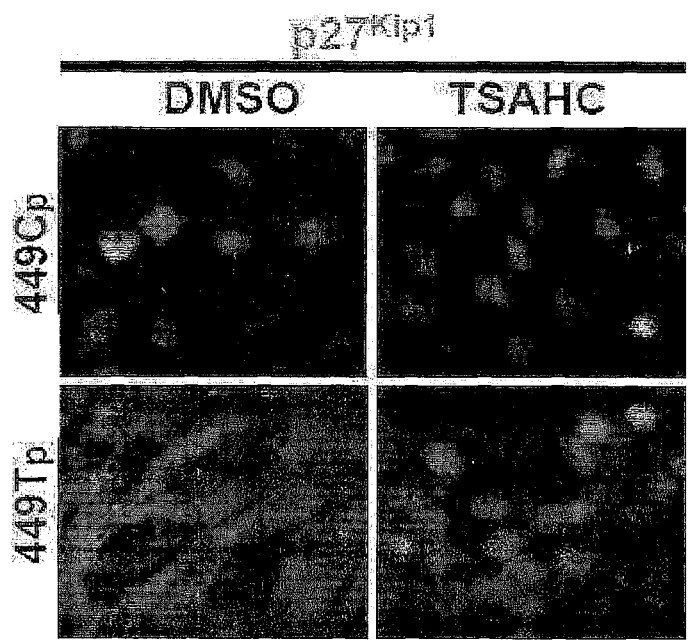
FIG. 47 shows the results of immunofluorescent staining for p27$^{kip1}$.

Furthermore, the chalcone compound according to the present invention effectively reduces TM4SF5-induced $p27^{kip1}$, $pS^{10}p27^{kip1}$ and $pY^{577}FAK$ expression and α-SMA or vimentin expression (FIG. 45). When TM4SF5-expressing SNU449 cell line, SNU 449Tp is treated with the chalcone compound according to the present invention, cytosolic $p27^{kip1}$ is not stabilized anymore, leading to a decrease in its cytosolic level (FIG. 47).

A chalcone compound according to the present invention, in particular TSAHC, affects N-linked glycosylation activity of TM4SF5 and a membrane protein interacting therewith, and thus impedes or inhibits the binding of TM4SF5 with other proteins including integrins in the membrane or the tetraspanin-web to perform its tumorigenic function.

Figure 50:
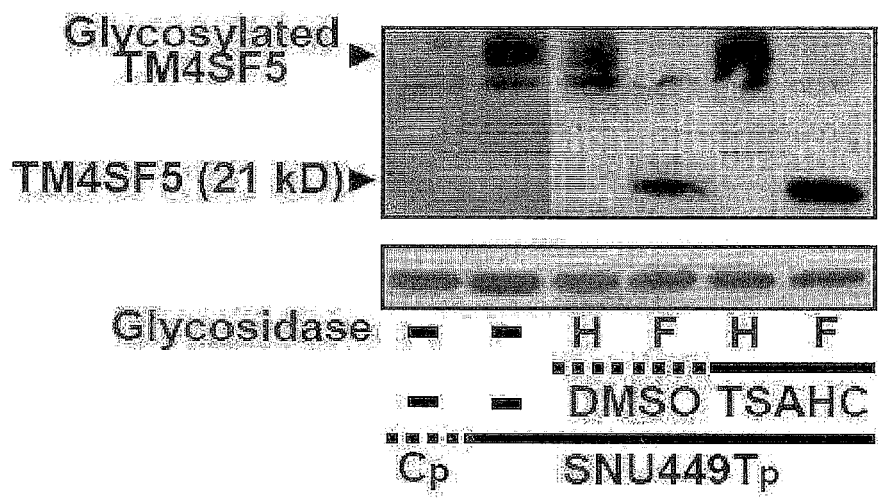
FIG. 50 shows the results of Western blotting of lysates from SNU449 Cp and SNU449Tp cells, which were treated with PNGase F and Endo H.

This effect of the present compounds is observed by the increase in sensitivity of an N-linked glycosylated region of TM4SF5 to FNGase F upon TSAHC treatment (FIG. 50). Hence, the chalcone compounds of the present invention, including TSAHC, deem to attach TM4SF5 itself to modify the N-linked glycosylation structure and affect the association of TM4SF5 with other proteins (in the tetraspanin-web), thereby inhibiting the carcinogenic function of TM4SF5.

Figure 48:
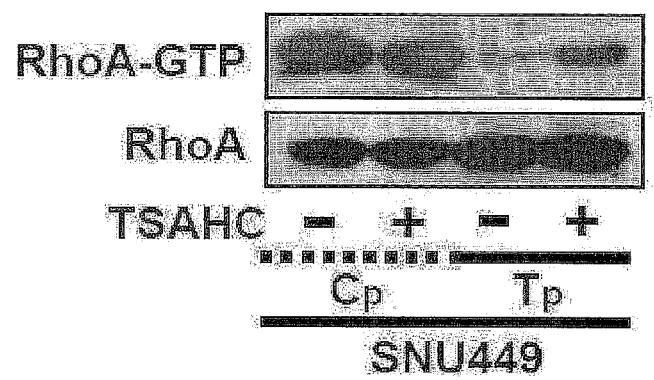
FIG. 48 shows the results of an in vitro RhoA activity assay.
Figure 49:
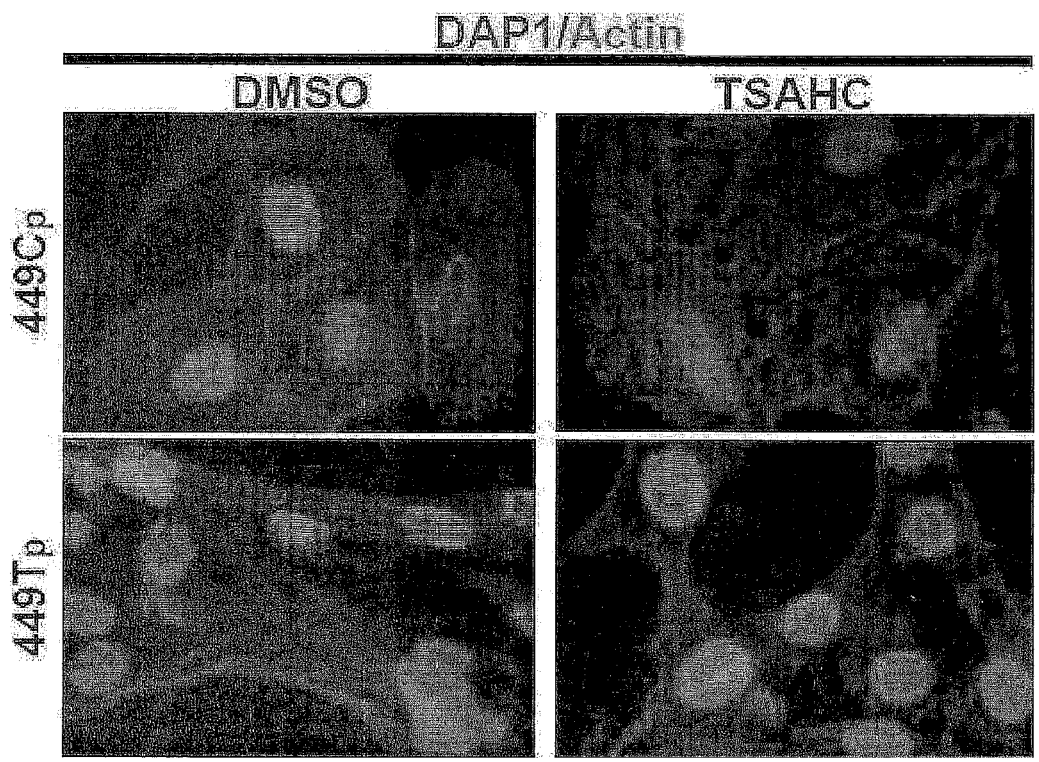
FIG. 49 shows the results of immunostaining for DNA and the actin cytoskeleton.

Furthermore, in TM4SF5-expressing cells, the chalcone compounds of the present invention counteract the inhibitory effect of TM4SF5 on RhoA activity (FIG. 48), and return the elongated cell morphology to the polygonal shape (FIG. 49). These results indicate that the chalcone compounds of the present invention inhibit TM4SF5-mediated events, and thus indicate that the chalcone compounds of the present invention, which act as antagonists to TM4SF5, have potential as therapeutic drugs for TM4SF5-mediated tumorigenesis.

The TM4SF5-mediated cell migration and invasion are also effectively inhibited by the chalcone compounds of the present invention, for example TSAHC. When TM4SF5-expressing cells are treated with TSAHC, cell migration (FIG. 65), invasion into collagen gels (FIG. 66) and invasion into Matrigel (FIG. 67) are effectively inhibited. These results indicate that the chalcone compounds of the present invention inhibit the enzymatic activity of MMPs which is involved in cell migration (FIG. 68), and that TSAHC is able to effectively inhibit TM4SF5-mediated tumor cell metastasis as well as tumor induction.

In a further aspect, the present invention relates to an anticancer composition comprising at least one of the chalcone compounds, preferably the compounds described in Table 1, as an effective ingredient. Example 8 shows that anticancer activity is expressed even upon the treatment with one (TSAHC) among the compounds of Table 1.

The chalcone compounds according to the present invention may be used in the form of a chalcone derivative, which is in the form of a pharmaceutically acceptable salt.

The salt useful in the present invention is an acid addition salt formed with a pharmaceutically acceptable free acid. That is, the chalcone derivative may be in the form of a pharmaceutically acceptable acid addition salt, which is formed using a common method in the art. The free acid may be an inorganic acid or an organic acid. Examples of such an inorganic acid include hydrochloric acid, bromic acid, sulfuric acid and phosphoric acid. Examples of such an organic acid include citric acid, acetic acid, lactic acid, maleic acid, fumaric acid, gluconic acid, methanesulfonic acid, succinic acid, tartaric acid, 4-toluenesulfonic acid, embonic acid, glutamic acid and aspartic acid. A preferable inorganic acid is hydrochloric acid, and a preferable organic acid is methanesulfonic acid.

In addition to pharmaceutically acceptable salts thereof, the chalcone compounds according to the present invention may include all salts, hydrates and solvates thereof, which can be prepared using common methods.

For clinical application, the chalcone compounds or salts thereof according to the present invention may be administered alone, but are typically mixed with excipients, binders, lubricants, disintegrators, coating agents, emulsifiers, suspending agents, solvents, stabilizers, absorption stimulators and/or ointment bases, to be administered in the form of pharmaceutical mixtures, which are suitably formulated for specific uses and desired purposes. The mixtures may be used for injection or oral, rectal or topical application.

In more detail, as described above, the pharmaceutical anticancer compositions comprising the chalcone compounds or salts thereof may be administered orally, for examples, in the form of tablets, coated tablets, dragées, hard or soft gelatin capsules, solutions, emulsions or suspensions. Also, the compositions may be administered rectally, for example, in the form of suppositories; locally or transdermally, for example, in the form of ointments, creams, gels or solutions; or parenterally, for example, in the form of injection solutions.

For the preparation of tablets, coated tablets, dragées, or hard or soft gelatin capsules, the chalcone compounds of the present invention may be mixed with pharmaceutically inert inorganic or organic excipients (pharmaceutically acceptable carriers). Examples of excipients for tablets, coated tablets, dragées and hard gelatin capsules include lactose, maize starch or derivatives thereof, talc, and stearic acid or salts thereof. Suitable carriers for soft gelatin capsules are, for example, vegetable oils, waxes, fats, semi-solid and liquid polyols, and the like. However, depending on the nature of the active ingredient, excipients are often not required in the case of soft gelatin capsules. Suitable excipients for the preparation of solutions and syrups are, for example, water, polyols, sucrose, invert sugar, glucose, and the like. Suitable excipients for injection solutions are, for example, water, alcohols, polyols, glycerol, vegetable oils, and the like. Suitable excipients for suppositories and local or transdermal application are, for example, natural or hardened oils, waxes, fats, semi-solid or liquid polyols, and the like.

The pharmaceutical compositions may also contain preservatives, solubilizers, stabilizers, wetting agents, emulsifiers, sweeteners, colorants, flavoring agents, salts for controlling osmotic pressure, buffers, coating agents or antioxidants. They may also contain other therapeutically useful drugs.

Consequently, the pharmaceutical formulation for oral administration may be in the form of granules, tablets, sugar-coated tablets, capsules, pills, suspensions or emulsions. A parental formulation may be administered, for example, intravenously, intramuscularly or subcutaneously. For such parenteral administration, the composition may be used in the form of a sterile aqueous solution which may contain other substances, for example, salts or glucose to make the solution isotonic with blood. Anticancer agents may be administered in the form of a suppository or using a pessary, or they may be applied topically in the form of a lotion, solution, cream, ointment or dusting powder.

The daily dosage for oral or parenteral administration will be in the range from 5 mg to 2000 mg of the chalcone compound of the present invention, which may be administered in a single dose or in several divided doses. However, it is to be understood that the actual dosage should be determined taking into account several related factors, including administration routes, the patient's age, gender and weight, and the severity of the illness. Thus, the above dosage does not limit the scope of the present invention in any way.

EXAMPLES

Hereinafter, the present invention will be described in further detail with reference to examples. It will be apparent to one skilled in the art that these examples are for illustrative purpose only and are not construed to limit the scope of the present invention.

In particular, the following examples employ only hepatocarcinoma cells, but it will be apparent to persons skilled in the art that various types of human-derived cancer tissues and carcinoma cell lines, including pancreatic, gastric, liver, colon, brain, breast, prostate, ovarian, thyroid, bladder, uterine, esophageal, bladder and lung cancer cells, are available.

Example 1

Culture of TM4SF5-Expressing Cancer Cells (1) Cell Line Establishment

In order to establish a cell line permanently and stably expressing TM4SF5 (GenBank No. NM-003963), human hepatocarcinoma SNU449 cells (KCLB No. 00449) were infected with retroviruses containing a control vector pLNCX (Clontech Laboratories Inc., Palo Alto, Calif.) and a retroviral vector pLNCX carrying TM4SF5.

A TM4SF5-expressing retrovirus was prepared as follows. TM4SF5 from a cDNA pool of hepatocarcinoma Huh7 cells (JCRB No. 0403) was amplified using PCR, and was inserted into the HindIII/ClaI sites of the retroviral vector pLNCX (pLNCX-TM4SF5). The pLNCX-TM4SF5 construct was transfected into PT67 packaging cells (ATCC CRL-12284). Cells stably expressing TM4SF5 were selected and cultured to produce a retrovirus expressing TM4SF5 (*Experimental Cell Research,* 312:2983, 2006). Hereinafter, SNU449 cells containing the control vector pLNCX were designated "SNU449 Cp (or Cp)", SNU449 cells expressing TM4SF5 were designated "SNU449Tp (or Tp)".

SNU449 cells were infected with the TM4SF5-expressing retrovirus. Formed colonies were pooled (SNU449 Cp and SNU449Tp), and single colonies were isolated (TM4SF5-expressing T3, T7, T11 and T16 clones).

To prepare a Huh7 cell line in which TM4SF5 expression is suppressed, Huh7 cells were transfected with an shRNA against TM4SF5 to selectively isolate only shTM4SF5-expressing cells with G418 (500 µg/ml). The selected clones were cultured in 10% FBS-containing RPMI-1640 medium supplemented with gentamycin alone (0.25 µg/ml) or gentamycin plus G418 (200 µg/ml) in an incubator at 37 r under 5% $CO_2$.

(2) Materials and Methods

① Preparation of Antibody Against TM4SF5

A C-terminal region of TM4SF5 (amino acids 229 to 594 digested with EcoRI) was inserted into a pGEX-5×2 vector (Pharmacia Biotech.), and its sequence was determined. PBS containing 0.3% SDS and a proteinase inhibitor was used to obtain an IPTG-induced recombinant protein from DH5a cells. The expressed protein was isolated and electrophoresed on an SDS gel. Antigen was extracted from the gel and mice were immunized therewith. After a total of three immunizations, sera were collected from the immunized mice and assessed for the immune reactivity to the recombinant protein and an animal cell extract.

② Protein Isolation and Western Blotting

Cell lysates, obtained under various experimental conditions, were prepared using RIPA buffer after cells under various conditions were washed with PBS. In special cases, employed cells were transfected with given expression vectors or infected with an adenovirus expressing an shRNA to TM4SF5 or a siRNA to $p27^{kip1}$. In addition, cells treated with 10 µM of cycloheximide for a given period of time were used. For such cell lysates, protein was quantified, and the same amounts of protein were used. Western blotting was performed using antibodies to phospho-$Y^{577}$FAK, phospho-$Y^{416}$Src, c-Src, RhoA, $p120^{ctn}$, β-catenin, $pS^{10}p27^{kip1}$, FAK, E-cadherin, ZO1, Rac1, p190RhoGAP, $p27^{kip1}$, GRAF, hKIS, desmoplakin, α-tubulin, α-catenin, and α-smooth muscle actin (α-SMA).

③ Immunofluorescent Staining

For immunofluorescent staining of intracellular proteins, cells were seeded on cover glasses coated with 10% FBS/RPMI-1640, and were cultured at 37° C. for one day until they showed their typical morphology and were stably attached onto the surface of the cover glasses. When cells were transfected with given specific genes or infected with various viruses, they were used after being cultured for a given period of time. Cells treated with 10 mM lysophosphatidic acid (LPA) were used 1 hour after being attached to cover glasses. Immunofluorescent staining was carried out by preparing a slide for fluorescent analysis through incubation with a primary antibody against a target protein, washing out unbound antibody molecules, incubation with a fluorescein-conjugated secondary antibody and washing out unbound antibody molecules, and actin filament staininh was carried out with rhodamine-conjugated phalloidin. Antibodies used included antibodies against E-cadherin, β-catenin, FLAG, 4'-6-diamidino-2-phenylindole (DAPI), 5-brorno-2'-deoxy-uridine (BrdU), $p27^{kip1}$, ZO1 (zonula occludens-1), and the like. Immunofluorescent stained cover glasses were placed on slides and observed under a fluorescence microscope or a confocal laser scanning microscope.

④ RT-PCR $p27^{kip1}$ mRNA levels were analyzed using RT-PCR. Total RNA was isolated from TM4SF5-null cells and from TM4SF5-expressing cells at various time points after being treated with actinomycin D. Then, mRNA was purified from the isolated total RNA. RT-PCR was carried out using the mRNA with primers specific to $p27^{Kip1}$. A pair of primers, sense: 5'-taa ccc ggg act tgg aga ag-3'(SEQ ID NO: 3) and antisense: 5'-gct tct tgg gcg tct gct c-3' (SEQ ID NO: 4), was used.

⑤ Preparation of Cytosolic and Nuclear Protein Fractions of $p27^{kip1}$ Through Fractionation Cytosolic and nuclear expression levels of $P27^{kip1}$ were examined in SNU449Tp cells and T16 cells, which express TM4SF5, using a fractionation method described by Liang (Nature Medicine, 8:1153-1160, 2002) and others.

⑥ Soft Agar Assay 0.7% agar in a culture medium containing 10% FBS was poured into 60-mm culture dishes and allowed to solidify. $10^6$ cells were mixed with 0.3% agar in a culture medium containing 10% FBS and layered on the bottom agar. The culture dishes were incubated in an incubator at 37° C. under 5% $CO_2$ for 25 days. The medium was replaced by a 10% FBS-containing medium supplemented with 200 μg/ml of G418 every two days. The cell colonies formed were observed and scored using a microscope equipped with a digital camera.

⑦ Statistical Analysis

Student's t-test was used to compare means to determine whether differences in the data were significant. If the p value was less than 0.05, the difference between groups was considered statistically significant.

Example 2

TM4SF5-Mediated $pY^{577}FAK$ Expression and Inhibition of RhoA Activity (1) Morphological Properties of TM4SF5-Expressing Cells Parental SNU449 cells (SNU449p or p), not expressing TM4SF5, SNU449 Cp cells, permanently expressing the control vector, and TM4SF5-expressing clones (SNU449Tp, T3, T7, and T16), established in Example 1, were morphologically observed under an optical microscope. Also, Western blotting was performed with an anti-TM4SF5 antibody and an anti-α-tubulin antibody.

To investigate various actin cytoskeletal structures of cells according to TM4SF5 expression, control cells (SNU449 Cp) and TM4SF5-expressing cells (SNU449Tp) were grown on glass coverslips and stained with phalloidin conjugated to rhodamine.

As a result, compared to parental SNU449p cells, T3, T7, T16 and Tp clones were morphologically elongated (FIG. 1). Fluorescent staining of the actin cytoskeleton in SNU449 cells showed that cells maintained a spread and polygonal shape having a highly fibrous actin network. In TM4SF5-expressing SNU449Tp cells, abnormal actin bundles were formed along the elongated-shaped cells (FIG. 2).

(2) Effects of $pY^{577}FAK$

In order to investigate signaling pathways involved in the aforementioned morphological change, TM4SF5-expressing cell lines (SNU449Tp, T3, T7 and T16), established in Example 1, were assessed for expression levels of FAK phosphorylated at Tyr577 ($pY^{577}FAK$) and c-Src phosphorylated at Tyr 416 ($pY^{416}cSrc$), Rac1 activity and RhoA activity. Whole cell lysates were prepared and subjected to Western blot analysis, which was performed with each antibody against proteins indicated in FIGS. 3 and 5. The activity rf RhoA and Rac1 was monitored by pull-down of RhoA and Rac1 from the cell lysates in vitro.

In addition, when TM4SF5 expression was inhibited using an shRNA to TM4SF5 (shTM4SF5), changes were examined. Parental SNU449p cells, SNU449 Cp control cells and various TM4SF5-expressing cells were transfected with an shRNA to green fluorescent protein (GFP), a scrambled shRNA having a random nucleotide sequence and an shRNA to TM4SF5. Cells were harvested and subjected to Western blotting and RhoA activity analysis.

As a result, TM4SF5-expressing cells exhibited increased expression of $pY^{577}FAK$ and $pY^{416}cSrc$ proteins and elevated Rac1 activity, but showed decreased RhoA activity (FIGS. 3 and 5). The increased levels of $pY^{577}FAK$ and inhibition of RhoA activity, mediated by TM4SF5, were reversed when TM4SF5 expression was suppressed (FIGS. 4 and 6).

Also, SNU449Tp cells were transfected with pEGFP and shTM4SF5. After 24 hrs, cells were placed on coverslips and further cultured for 24 hrs. Cells were fluorescent stained with rhodamine-conjugated phalloidin for actin filaments and DAPI for DNA. shTM4SF5-introduced cells were restored to a polygonal shape having a highly fibrous actin network, which was the same as SNU449 control cells, whereas neighboring cells not containing shTM4SF5 did not undergo the morphological change due to TM4SF5 expression (FIG. 7).

(3) Inhibition of RhoA Activity

The role of $pY^{577}FAK$ in the RhoA inactivation through RhoGAP proteins was examined. Cell lysates from Cp cells and Tp cells were immunoprecipitated with an antibody to FAK. Immunoprecipitated mixtures were analyzed using Western blotting with antibodies against p190RhoGAP, GRAF and FAK. Also, an (HA)3-tagged FAK wild type and a Y577F FAK mutant were transiently overexpressed in SNU449Tp cells. After two days, cell lysates were immunoprecipitated and subjected to Western blotting with antibodies indicated in FIG. 10.

As a result, TM4SF5-expressing cells showed stronger binding between FAK and p190RhoGAP or between FAK and GRAF than that of TM4SF5-null SNU449 Cp cells (FIG. 9). The TM4SF5-mediated binding of FAK to p190RhoGAP or FAK to GRAF decreased when the FAK mutant, in which the tyrosine residue at 577 was replaced with phenylalanine, was expressed (FIG. 10). These results indicate that pY$^{577}$FAK plays an important role in a series of signaling pathways to RhoA in TM4SF5-expressing cells.

Figure 11:
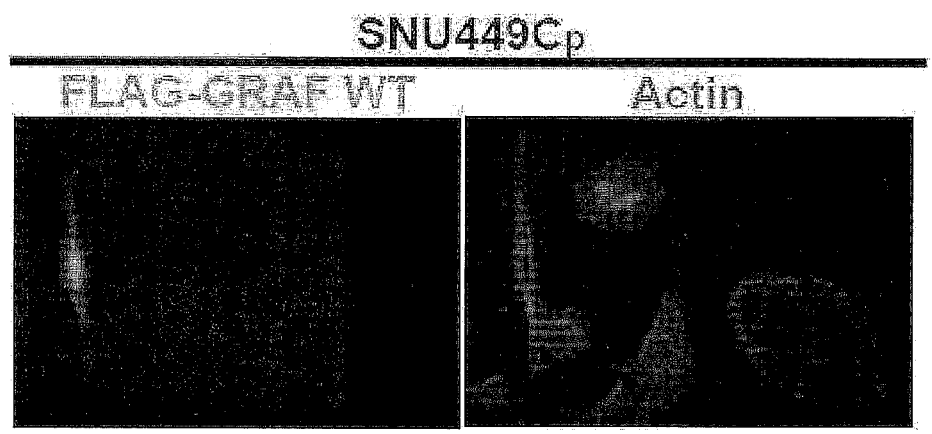
FIG. 11 shows the results of immunofluorescent staining of control cells, in which FLAG-tagged GRAF was overexpressed.

In addition, FLAG-tagged GRAF (GTPase regulator associated with FAK) was transiently overexpressed in control cells. After 24 hrs, cells were placed on coverslips as described above and cultured for one day. Then, cells were immunofluorescence-stained with anti-actin and anti-FLAG antibodies. The transient expression of GRAF or p190RhoGAP changed the morphology of control cells not expressing TM4SF5 (FIG. 11).

These results indicated that TM4SF5 expressed in SNU449 cells inhibited RhoA activity, leading to the elongation of cells, and that this was induced through a FAK-p190RhoGAP or FAK-GRAF interaction.

Example 3

Effects of TM4SF5-Mediated Cytosolic p27$^{kip1}$ Accumulation (1) Increase of p27$^{kip1}$ Expression According to TM4SF5 Expression In order to determine whether TM4SF5 inhibited RhoA activity through p27$^{kip1}$, SNU449 Cp cells and SNU449Tp cells were immunofluorescence-stained with an antibody to p27$^{kip1}$ and DAPI. The nucleus and cytosol of the cells were fractionized according to the method described in ⑤ of Example 1-(2), and were analyzed using Western blotting with anti-p27$^{kip1}$ and anti-α-tubulin antibodies.

As a result, it would be seen that the p27$^{kip1}$ protein was localized in the cytosol in remarkably high concentrations in TM4SF5-expressing cells (FIG. 12). In contrast, the protein was mostly localized in the nucleus in low levels in TM4SF5-null control cells (FIG. 13).

Figure 14:
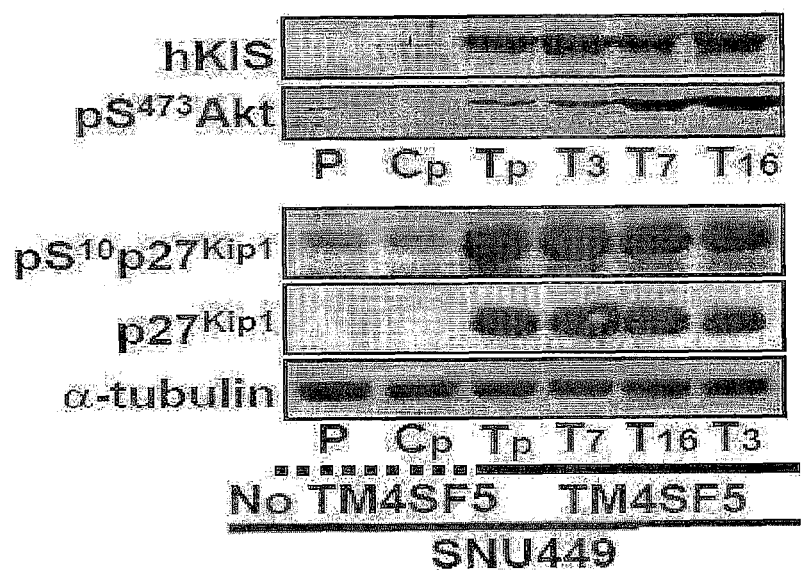
FIG. 14 shows the results of Western blotting for p27$^{kip1}$ expression levels and Ser10 phosphorylation using indicated antibodies.

In order to investigate the relationship between TM4SF5-mediated p27$^{kip1}$ expression levels and Ser10 phosphorylation, cell lysates were prepared from the various cell lines established in Example 1, and were analyzed using Western blotting with the antibodies indicated in FIG. 14. The cytosolic localization of p27$^{kip1}$ was found to be induced through Ser10 phosphorylation by human kinase-interacting with stathmin (hKIS) and activated PKB/Akt (FIG. 14).

Figure 16:
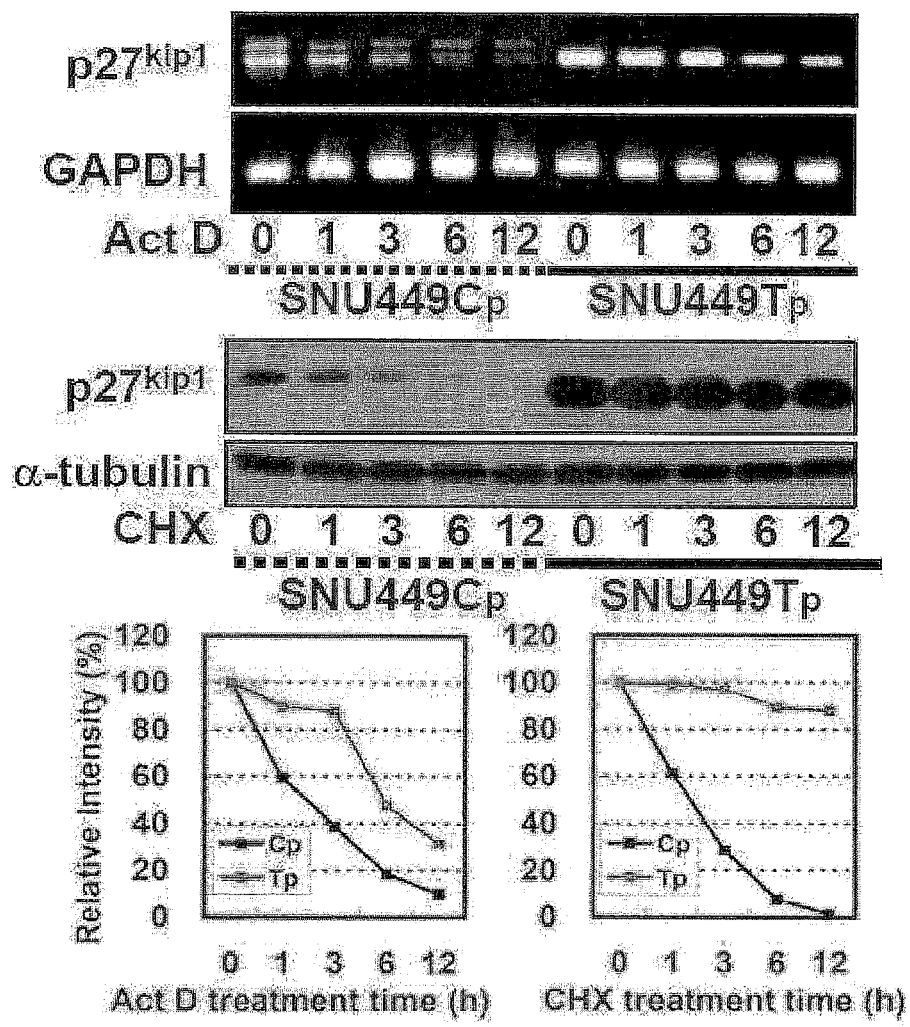
FIG. 16 shows the results of RT-PCR and Western blotting for examining the transcription of the p27$^{kip1}$ or GAPDH gene into mRNA.

Total RNA was extracted from cells treated with actinomycin D (10 mg/ml, Act D), and the expression of p27$^{kip1}$ and GAPDH was analyzed using RT-PCR. Also, cell lysates from cells treated with cycloheximide (10 mM, CHX) were analyzed using Western blotting with an antibody to p27$^{kip1}$. The band intensity was calculated relative to a control, and is presented as a graph (FIG. 16).

Figure 15:
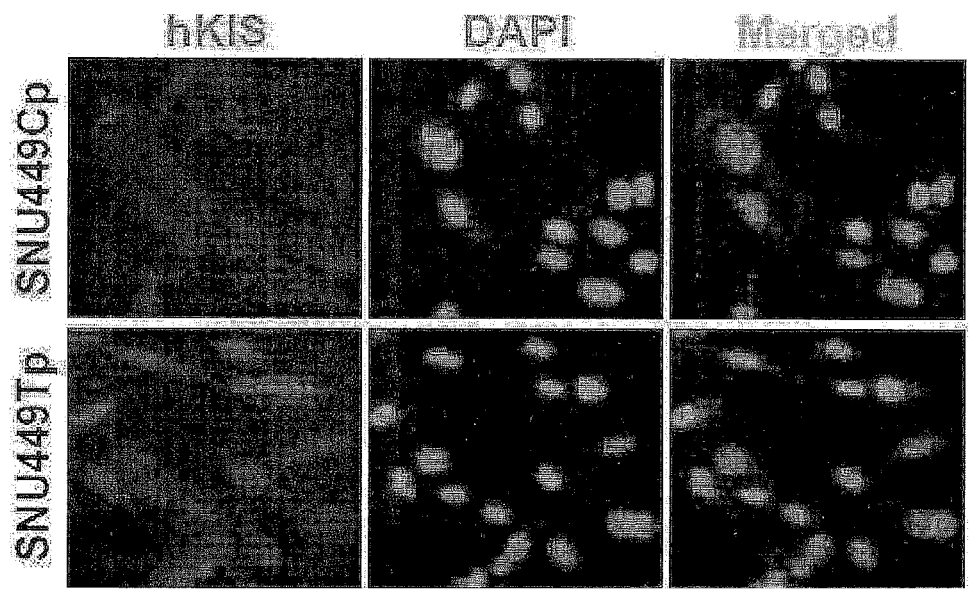
FIG. 15 shows the results of immunofluorescent staining of SNU449 Cp cells and SNU449Tp cells with respect to Ser10 phosphorylation of p27$^{kip1}$.
Figure 17:
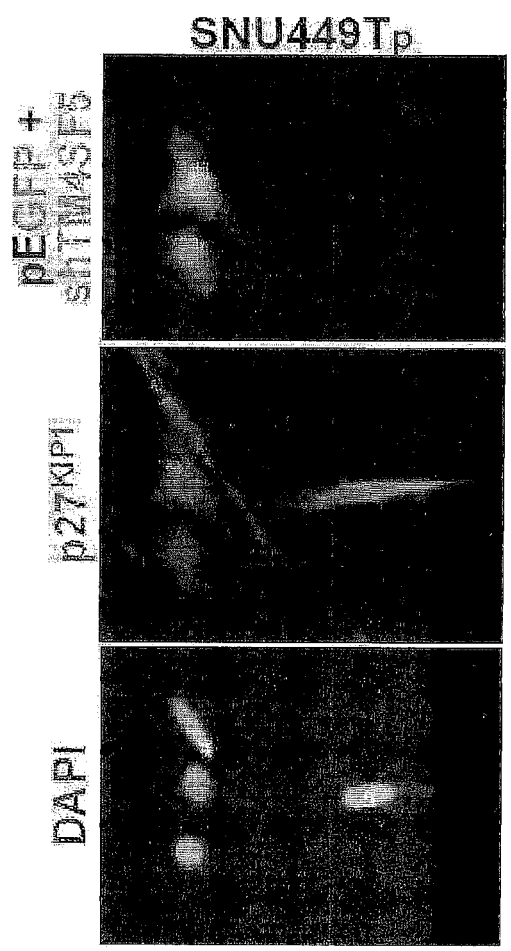
FIG. 17 shows the results of immunofluorescent staining of p27$^{kip1}$ and nuclear DNA (with DAPI) after SNU449Tp cells were transfected with pEGFP and shTM4SF5.

The marked increase of p27$^{kip1}$ expression in TM4SF5-expressing cells was found to be due to the high stabilization of p27$^{kip1}$ mRNA and protein (FIG. 15). This was further confirmed from the results that the suppression of TM4SF5 expression using an siRNA to TM4SF5, returned to the same morphology as that of TM4SF5-null SNU449 cells, reduced p27$^{kip1}$ protein levels in the cytosol, and did not induce the phosphorylation of p27$^{kip1}$ on Ser10 (FIG. 17).

In addition, the hypothesis that TM4SF5 contributes to the cytosolic stabilization of p27$^{kip1}$ was also found to be effective in various types of hepatocarcinoma cells expressing endogenous TM4SF5.

Hepatocarcinoma cell lines endogenously expressing TM4SF5 were transfected with an shRNA to GFP, a scrambled (Scr) shRNA and an shRNA to TM4SF5. After 48 hrs, whole cell lysates and lysates of SNU449 Cp and SNU449Tp cells were prepared and analyzed using Western blotting with the antibodies indicated in FIG. 18. As a result, the suppression of endogenously expressed TM4SF5 was observed to reduce the expression and Ser10 phosphorylation of p27$^{kip1}$ (FIG. 18).

Figure 21:
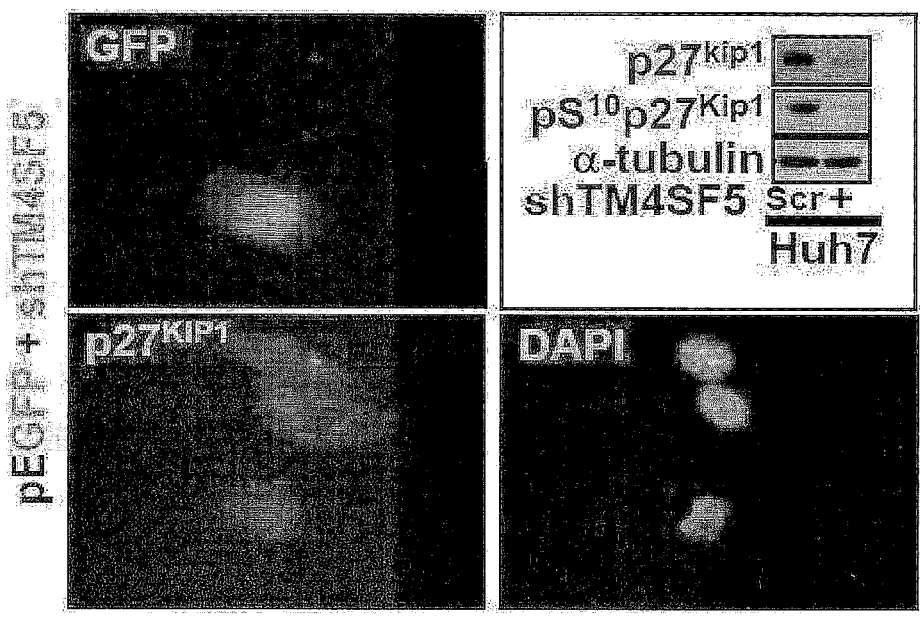
FIG. 21 shows the results of immunofluorescent staining of the cells of FIG. 20.

Cells were harvested and subjected to Western blotting and RhoA activity analysis. The HA-tagged FAK wild type and Y577F FAK mutant were overexpressed in SNU449Tp cells, and Western blotting was performed with indicated antibodies. As a result, the Y577F FAK mutant did not affect the expression levels or the Ser10 phosphorylation of p27$^{kip1}$ (FIG. 19). Also, Huh7 hepatocarcinoma cells were transfected with Scr or shTM4SF5 and pEGFP, and were immunofluorescence-stained for p27$^{kip1}$ and DAPI. The suppression of endogenously expressed TM4SF5 resulted in reduced cytosolic levels of p27$^{kip1}$ (FIG. 21).

These results demonstrate that TM4SF5 expression enhances the expression and cytosolic stabilization of p27$^{kip1}$, leading to the down-regulation of RhoA activity. In particular, the results shown in FIG. 19 indicate that there is no relationship between p27$^{kip1}$ expression and FAK. phosphorylation. Thus, the TM4SF5-mediated event of increased p27$^{kip1}$ expression leading to reduced RhoA activity and another TM4SF5-mediated event of the reduced RhoA activity through binding between FAK and RhoGAPs are induced via signaling pathways different from each other.

(2) Changes in Cell Morphology According to Cytosolic p27$^{kip1}$ Accumulation

Since TM4SF5-expressing cells had an elongated shape, as observed in Example 2, and highly expressed p27$^{kip1}$, as observed in Example 3-(1), the effect of changes in p27$^{kip1}$ expression levels on cell morphology was examined.

A FLAG-tagged p27$^{kip1}$ wild type was overexpressed in SNU449 Cp cells, established in Example 1. After 48 hrs, cells were immunofluorescence-stained with DAPI, rhodamine-conjugated phalloidin and FLAG. Then, cells were observed under a confocal scanning microscope. The overexpression of p27$^{kip1}$ in parental cells not expressing TM4SF5 changed the cell morphology into an elongated shape (FIG. 22).

SNU449Tp cells were infected with siRNAp27$^{kip1}$ adenovirus for 24 hrs, transfected with FLAG-tagged p27$^{kip1}$ S10A to culture for 24 hrs, and then subjected to immunofluorescent staining. Cell lysates were prepared and analyzed using Western blotting with the antibodies indicated in FIG. 24.

Figure 24:
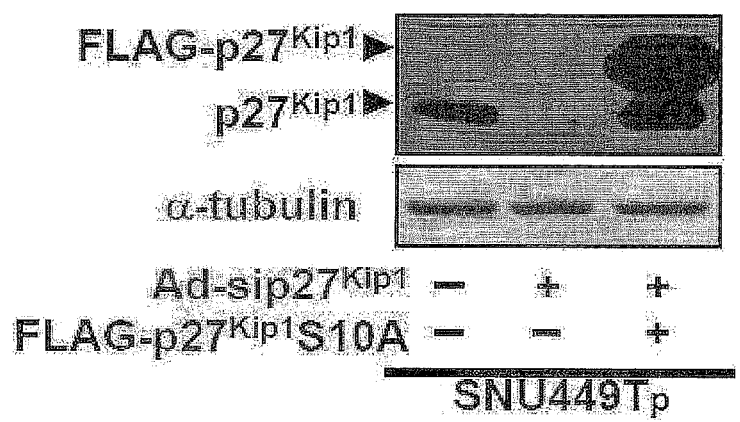
FIG. 24 shows the results of Western blotting with indicated antibodies.

As a result, in TM4SF5-expressing cells, the suppression of p27$^{kip1}$ expression along with the expression of the p27$^{kip1}$S10A mutant, which cannot be phosphorylated at the tenth residue due to the replacement of the Ser10 with alanine, interrupted the cytosolic translocation of p27$^{kip1}$ and changed the cell morphology into the same polygonal shape as that of SNU449 or SNU449 Cp cells (FIGS. 23 and 24).

Figure 25:
FIG. 25 shows the results of immunostaining of the cytoskeletal actin network of SNU449Tp cells, which were transfected with an active RhoA 63L mutant vector.

Also, for immunofluorescent staining of the actin cytoskeleton, SNU449Tp cells were transfected with pEGFP and an activated RhoA 63L mutant construct. As a result, the cell morphology was reversed to the polygonal shape by activated RhoA (FIG. 25).

In order to identify the relationship between the cytosolic p27$^{kip1}$-mediated morphological change and RhoA signaling, the change in cell morphology and the change in intracellular localization of p27$^{kip1}$ were examined when Rho GTPases were activated.

First, SNU449 Cp and SNU449Tp cells were grown on coverslips. Cells were then treated with 10 mM of lysophosphatidic acid (LPA), a Rho GTPase activator, for 1 hr, and immunostained for DAPI and p27$^{kip1}$. The LPA treatment resulted in a decrease in the cytosolic levels of p27$^{kip1}$ in SNU449Tp cells (FIG. 26).

In addition, SNU449Tp cells were transfected with pEGFP and an active mDia mutant, and SNU449 Cp cells with pEGFP and active Rac1 (Rac1 61L) or PAK1 (PAK1-caax). Then, cells were analyzed using immunofluorescent staining. Interestingly, the activation of the down-stream mediator of RhoA, mDia, returned the cell morphology to the same polygonal shape as that of SNU449 or SNU449 Cp cells, and resulted in a decrease in cytosolic p27$^{kip1}$ expression levels (FIG. 27).

Figure 26:
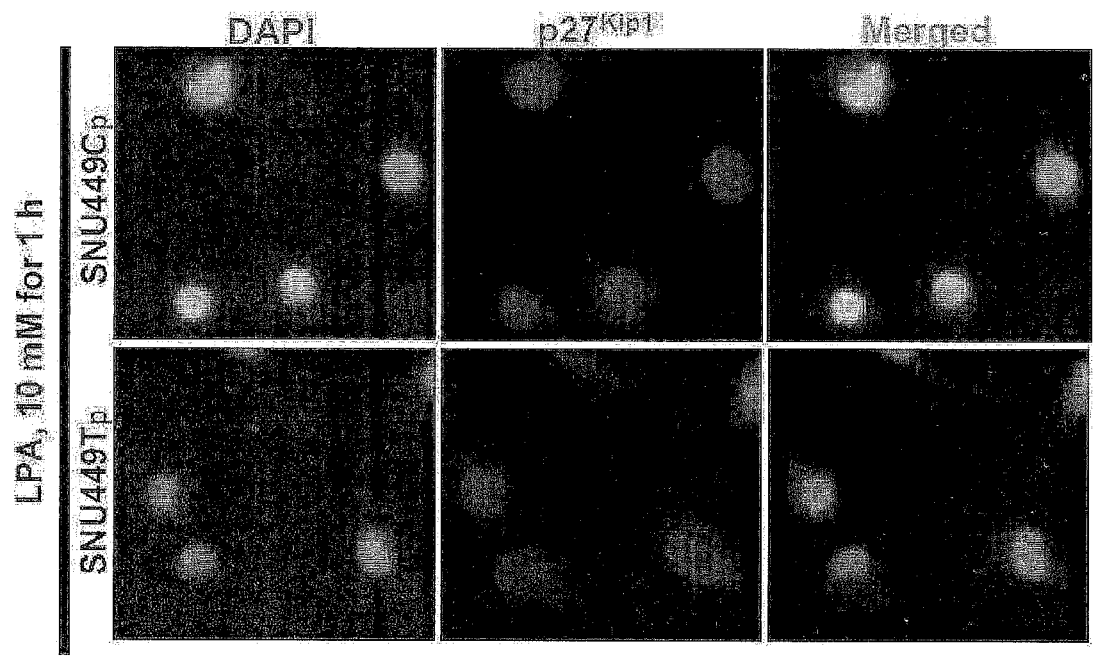
FIG. 26 shows the results of immunostaining for SNU449 Cp and SNU449Tp cells, which were treated with LPA.

This is considered to be because the p27$^{kip1}$ protein cannot be stabilized any further due to the activation of RhoA signaling, and thus localized in the nucleus (FIG. 26 and upper panel of FIG. 27). In contrast, even though cells did not express TM4SF5, the expression of activated Rac1 and its down-stream mediator PAK1 changed the cell morphology into an elongated shape and caused the cytosolic accumulation of p27$^{kip1}$ (middle and lower panels, FIG. 27).

These results indicate that a regulatory connection is present between cytosolic p27$^{kip1}$ and Rho GTPases including RhoA and Rac1, and that the control of the activity of Rho GTPases by cytosolic p27$^{kip1}$ induces changes in the morphology of TM4SF5-expressing cells.

Example 4

TM4SF5-Mediated EMT

The effect of TM4SF5 on the control of cell-cell contact was examined. First, cell lysates from TM4SF5-expressing cells and TM4SF5-null control cells were analyzed for the expression of proteins involved in cell-cell adhesion formation using an immunoblotting assay.

Figure 28:
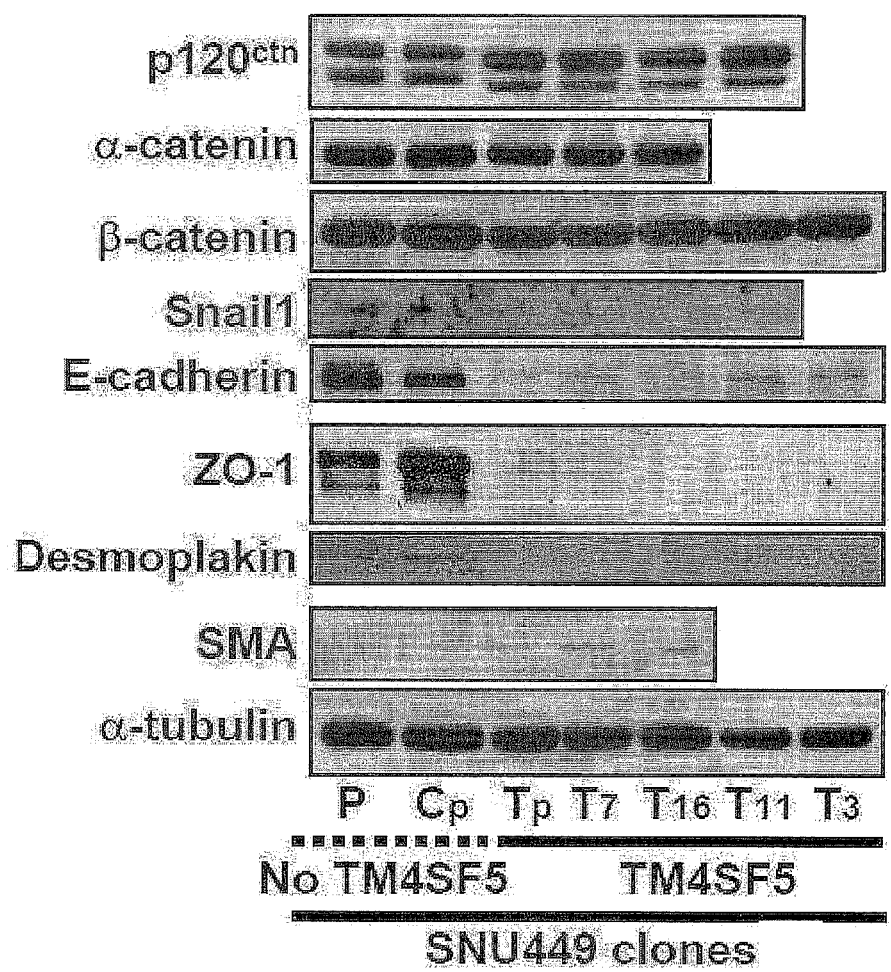
FIG. 28 shows the results of Western blotting for proteins involved in cell-cell contact.

As a result, the expression of cell contact proteins including E-cadherin, ZO1 and desmoplakin, was remarkably increased in TM4SF5-null cell lines, but was decreased in TM4SF5-expressing cells. In contrast, TM4SF5-expressing cells expressed high levels of α-SMA which is involved in epithelial-mesenchymal transition (EMT) (FIG. 28).

In addition, SNU449 Cp cells and SNU449Tp cells, grown at a high density, were placed on coverslips and were examined for the expression patterns of E-cadherin, (β-catenin and ZO1 using immunostaining. E-cadherin, β-catenin and ZO1 were well arranged at cell contact sites in SNU449 and SNU449 Cp cells not expressing TM4SF5, whereas these proteins were sporadically distributed in TM4SF5-expressing cells where intercellular contact was not well established (FIG. 29).

Figure 30:
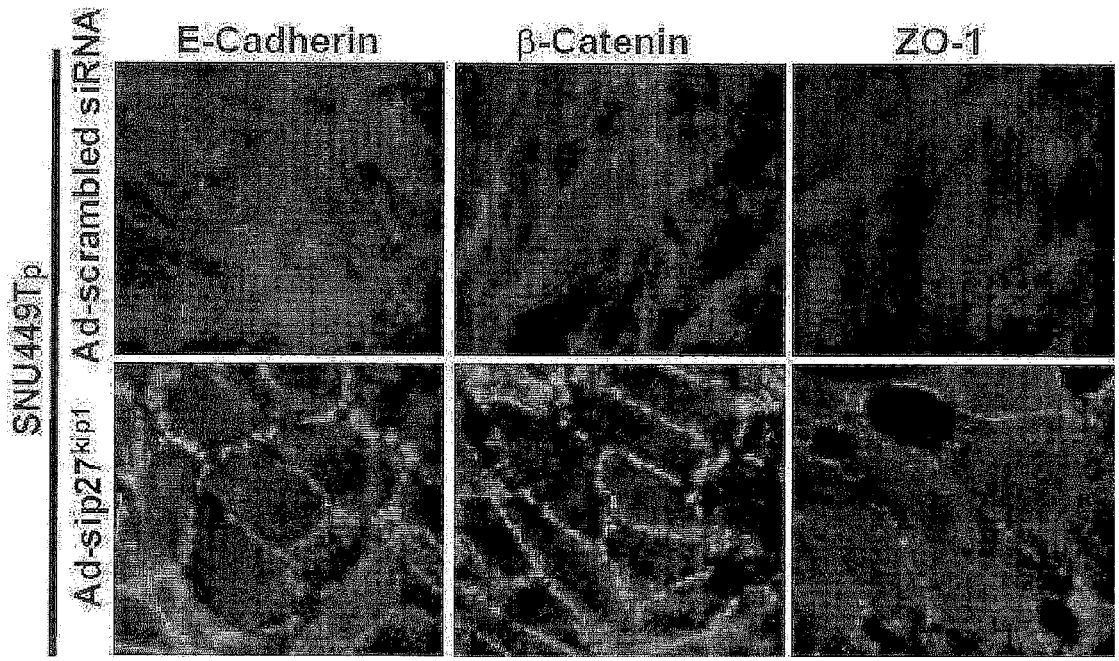
FIG. 30 shows the results of immunostaining for E-cadherin, β-catenin and ZO1 of SNU449Tp cells, in which p27$^{kip1}$ expression was inhibited.

SNU449Tp cells were infected with p27$^{kip1}$ shRNA adenovirus, as described in Example 1, and were immunostained for E-cadherin, β-catenin and ZO1. When p27$^{kip1}$ expression was suppressed, E-cadherin, β-catenin and ZO1 were rearranged in a regular form (FIG. 30), and α-SMA expression decreased.

Figure 31:
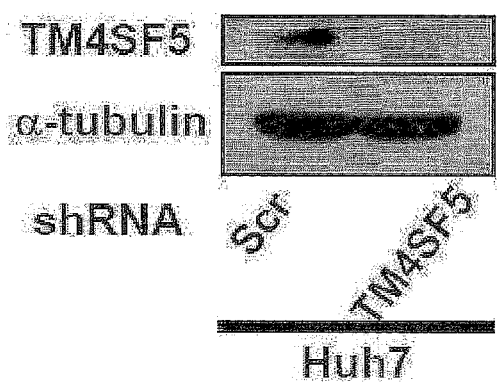
FIG. 31 shows the results of Western blotting of lysates from Huh7 cells, expressing shRNA and shTM4SF5.

In order to identify the role of endogenously expressed TM4SF5 on EMT regulation, Huh7 cells, expressing shRNA and shTM4SF5, were examined for the expression of TM4SF5 and α-tubulin (FIG. 31). Also, cells were treated with hepatocyte growth factor (HGF) (100 ng/ml) for 24 hrs and immunostained for ZO1.

Figure 32:
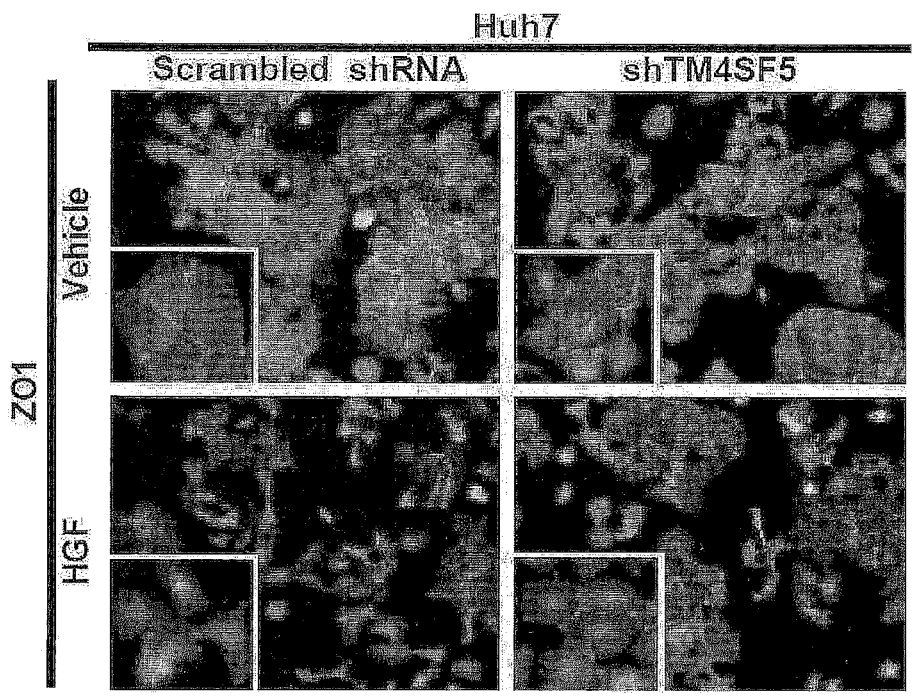
FIG. 32 shows the results of immunostaining for ZO1 localization when the cells of FIG. 31 were treated with HGF (100 ng/ml) for 24 hrs.

Huh7 cells form very good cell-cell contact because they form colonies when they grow, regardless of TM4SF5 expression. Thus, after EMT was induced using HGF, the effect of TM4SF5 on cell-cell adhesion formation was investigated. The disassembly of Huh7 cells (or contact disruption) by HGF was found to decrease in TM4SF5-suppressed Huh7 cells. These results indicate that TM4SF5 induces the loss of cell-cell contact (FIG. 32).

Example 5

The Loss of Contact Inhibition of Cell Growth by TM4SF5

Figure 34:
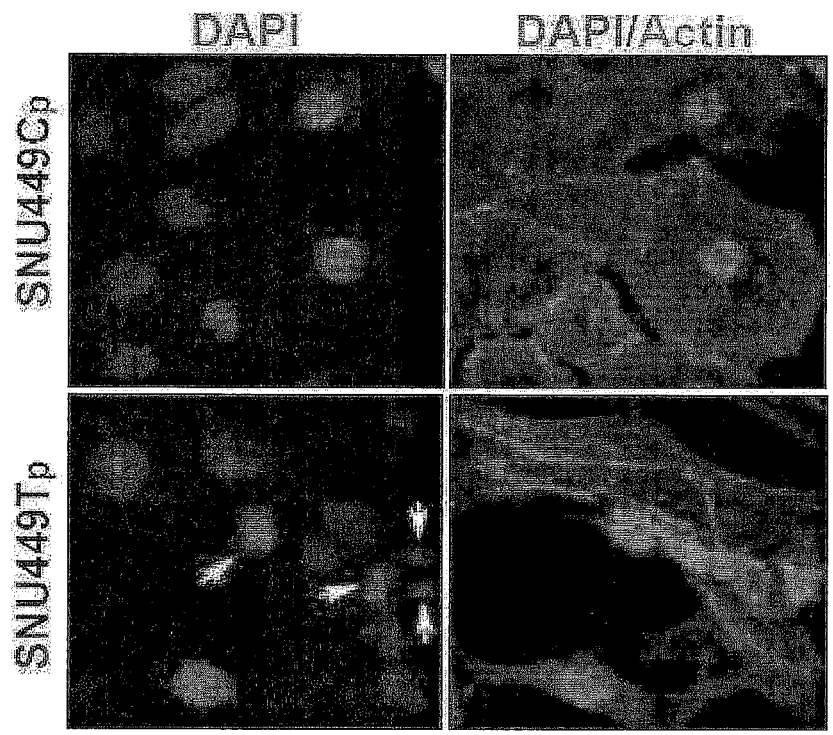
FIG. 34 shows the results of immunostaining of SNU449Tp cells, showing that cells are overlapping and dividing (arrows indicate the nuclei of cells undergoing cell division).

SNU449 Cp and SNU449Tp cells were grown on coverslips and stained to observe DNA, and the cytoskeletal actin network, using DAPI. The results are shown in FIGS. 33 and 34.

Arrows indicate the overlapping nuclei of cells undergoing cell division. This indicates that cells continued to divide despite the lack of additional space for growth. In addition, in order to measure the growth rates of the cells, 5×10$^4$ cells were plated onto 6-well plates and counted every 12 hrs. The results are expressed as a graph. TM4SF5-expressing SNU449Tp cells showed a continuous increase in growth rate, whereas SNU449 Cp control cells did not grow any further upon contact inhibition during proliferation, showing a saturation growth curve. This was observed even at a low cell density. That is, among cells at a low density, TM4SF5-expressing cells proliferated through cell division, during which two nuclei overlapped each other. In contrast, SNU449 cells and SNU449 Cp cells, not expressing TM4SF5, did not grow any further at a high cell density, at which adjacent cells are in substantial contact with each other (FIG. 34).

In addition, TM4SF5-expressing cell lines (T7, T16 and T3) were examined for the proportion of cells in the S phase of the cell cycle. TM4SF5-expressing cells showed a higher proportion of cell population in the S phase than SNU449 cells and SNU449 Cp cells not expressing TM4SF5 (FIG. 35). Also, SNU449 Cp cells and SNU449Tp cells were transfected with control shRNA and shTM4SF5, stained with propidium iodide for DNA, and analyzed for cell cycle phase distribution using flow cytometry. The suppression of TM4SF5 expression using shRNA was found to reduce the S-phase cell population (FIG. 36).

Figure 37:
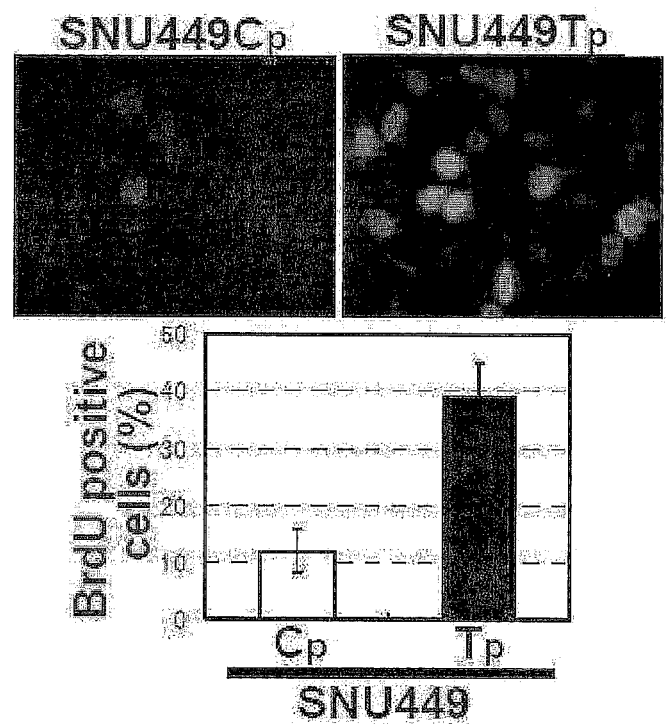
FIGS. 37 to 40 show the results of BrdU immunostaining for S-phase progression of SNU449 Cp and SNU449Tp cells (FIG. 37), LPA-treated SNU449Tp cells (FIG. 38), SNU449Tp cells infected with p27$^{kip1}$ shRNA adenovirus (FIG. 39), and SNU449T16m cells which were prepared by re-expressing E-cadherin in SNU449T16 cells.
Figure 38:
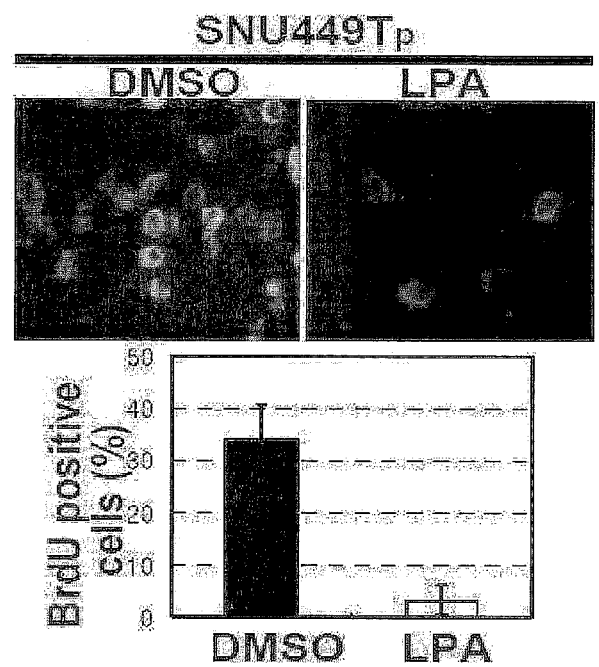
Figure 39:
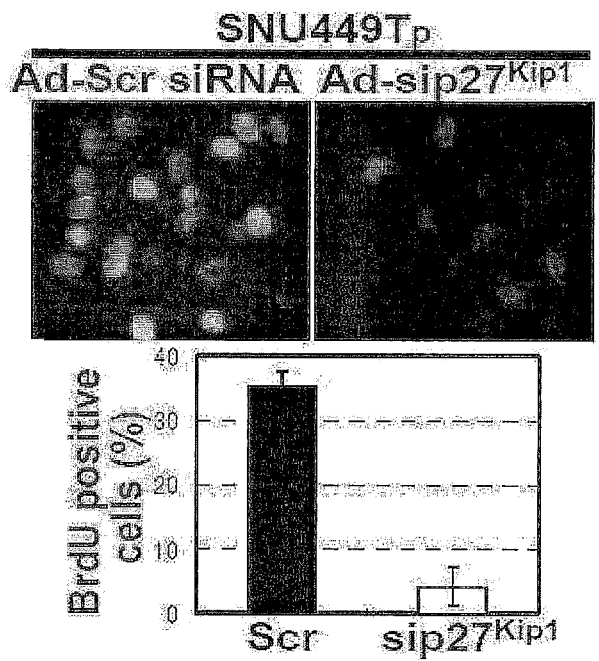
Figure 40:
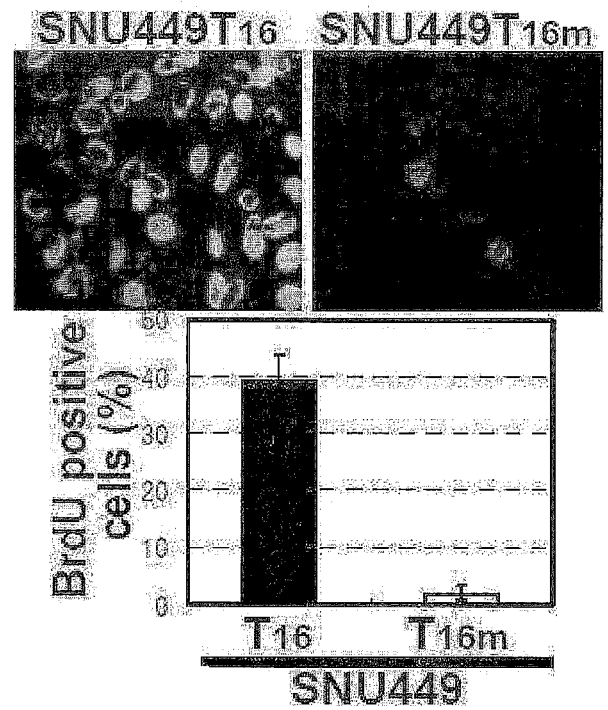

BrdU immunostaining also revealed that TM4SF5-expressing cells had a remarkably high cell population of the S phase, in which DNA synthesis occurs, compared to TM4SF5-null cells (FIG. 37). This S-phase progression, leading to high cell proportions in the S phase, was found to be specifically inhibited through LPA-induced RhoA activation (FIG. 38), the suppression of p27$^{kip1}$ expression (FIG. 39) and the re-expression of E-cadherin (FIG. 40).

Figure 41:
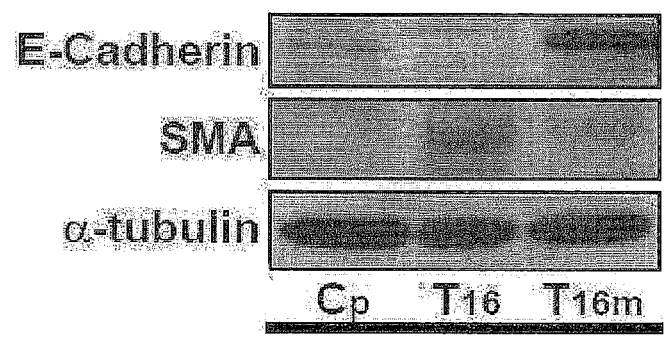
FIG. 41 shows the expression levels of indicated molecules in SNU449 Cp (Cp), SNU449T16 (T16) and SNU449T16m (T16m) cells.
Figure 42:
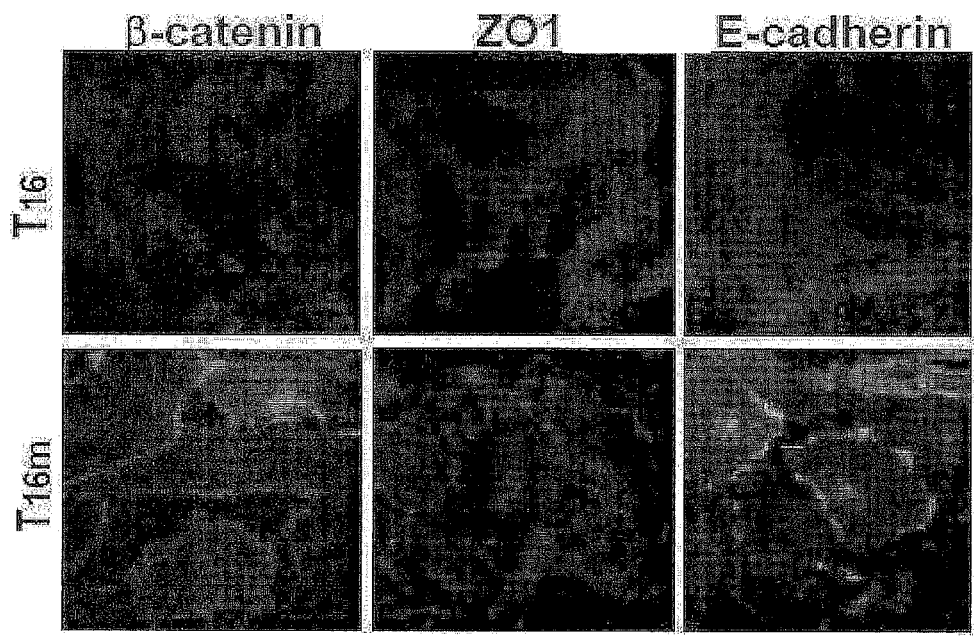
FIG. 42 shows the results of immunostaining of SNU449T16 (T16) and SNU449T16m (T16m) cells for β-catenin, ZO1 and E-cadherin.

In particular, SNU449T16m cells (the cell name "SNU449T16 m" was determined because they were derived from SNU449T16 cells), in which E-cadherin expression was up-regulated again, despite the expression of TM4SF5, exhibited the same intercellular contact pattern as that of TM4SF5-null cells (FIG. 42) and reduced the expression of α-SMA (FIG. 41).

From the results, the re-increase of E-cadherin expression in TM4SF5-expressing cells indicate that TM4SF5 induces the loss of contact inhibition of cell growth through EMT, further indicating that there is a close functional relationship between intercellular contact and contact-mediated growth inhibition.

Example 6

Properties of Tumor Tissues Formed by TM4SF5

The tumorigenic effect of TM4SF5 was assessed using two methods. First, TM4SF5-expressing cells or TM4SF5-null cells were placed under adhesion-independent growth conditions. Cells were cultured on soft agar for 27 days. A soft agar assay was performed using SNU449 cell lines according to the method described in Example 1-(6). On Day 27, cell colonies were observed under a phase-contrast microscope.

Figure 52:
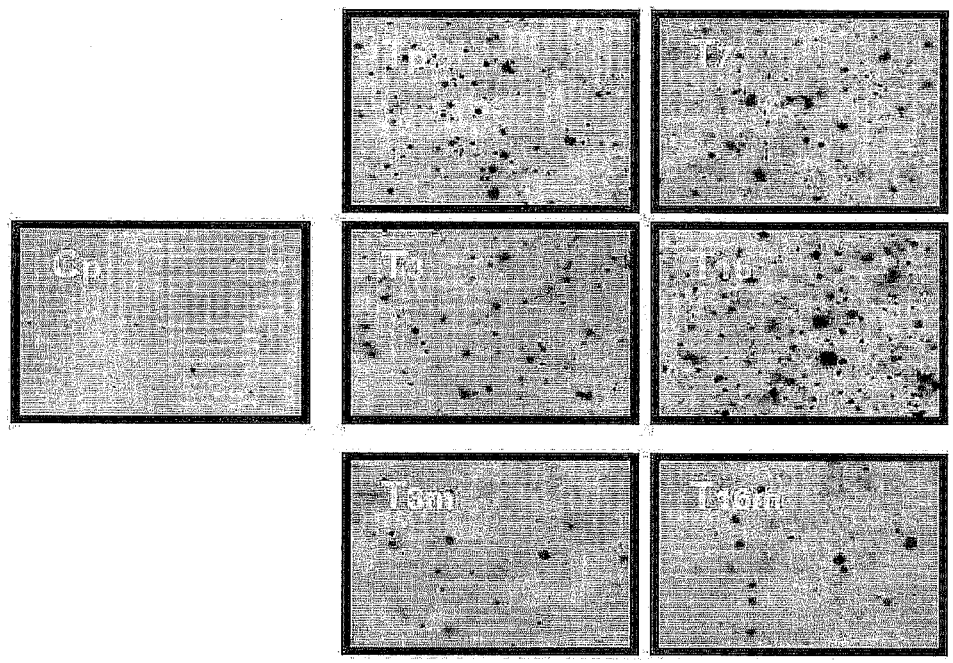
FIG. 52 shows the results of a soft agar assay using SNU449 cells.

As a result, TM4SF5-expressing cells formed more colonies than did TM4SF5-null cells. However, when E-cadherin was re-expressed in TM4SF5-expressing cells, the formation of cell colonies remarkably decreased in 449T3m and T16m cells. These results indicate that TM4SF5-induced EMT is related to cell adhesion-independent growth (FIG. 52).

Next, various SNU449 cell lines, expressing or not expressing TM4SF5, were injected into nude mice. 4-5 week-old female nude BALB/cAnNCrjBgi-nu mice (Orient. Co. Ltd), weighing about 20 g, were used. Animals were housed in sterilized cages, and given free access to sterilized water and feed. All procedures were carried out in the clean bench in which laminar flow was continuously maintained to provide a clean environment.

Nude mice were maintained under a light cycle of 12-hr light and 12-hr dark using indoor lamps, for biological cycle of day and night. Suspensions of SNU449 Cp, SNU449Tp, SNU449T16 and SNU449T16m cells were centrifuged, and the concentrated cells were counted using a hemocytometer to adjust them to a density of $1 \times 10^7$ cells/200 The prepared cells were subcutaneously injected into the flank of nude mice using a 1-ml syringe having a 26-gauge needle. Experimental animals were maintained according to the preclinical method for breeding of laboratory animals, Seoul National University, and were monitored for tumor formation by SNU449Tp cells.

Figure 53:
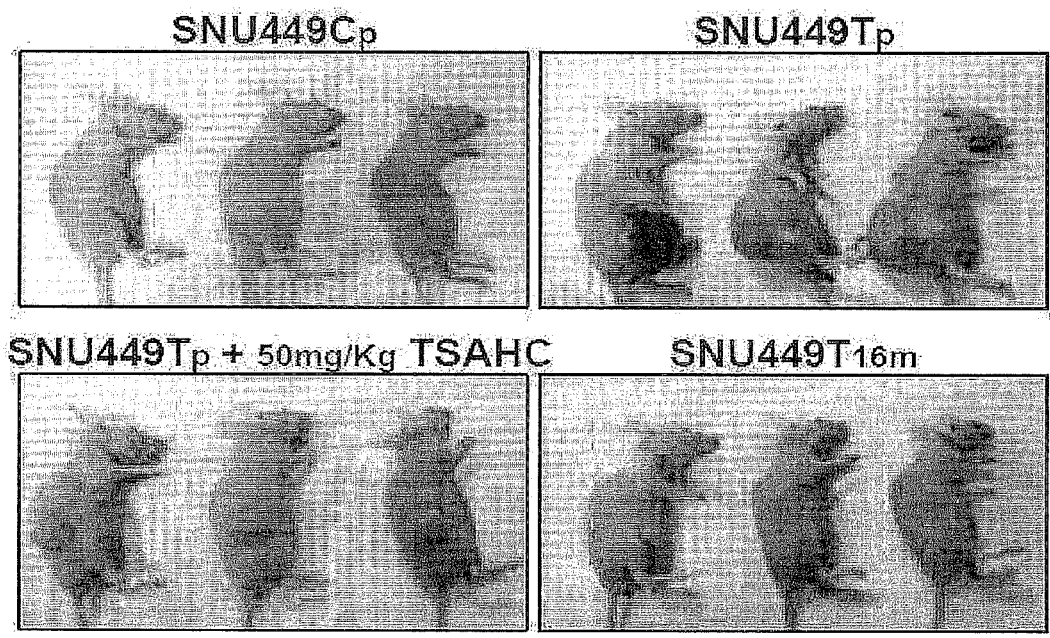
FIG. 53 shows the tumor formation induced by SNU449Tp and SNU449T16m cells compared to SNU449 Cp cells and the tumorigenesis reduced by TSAHC.

TM4SF5-expressing cell lines were highly tumorigenic, whereas parental cells (44.9p) and control cells (449 Cp), 449T3 nm cells and T16m cells did not form detectable tumors (FIG. 53).

Figure 54:
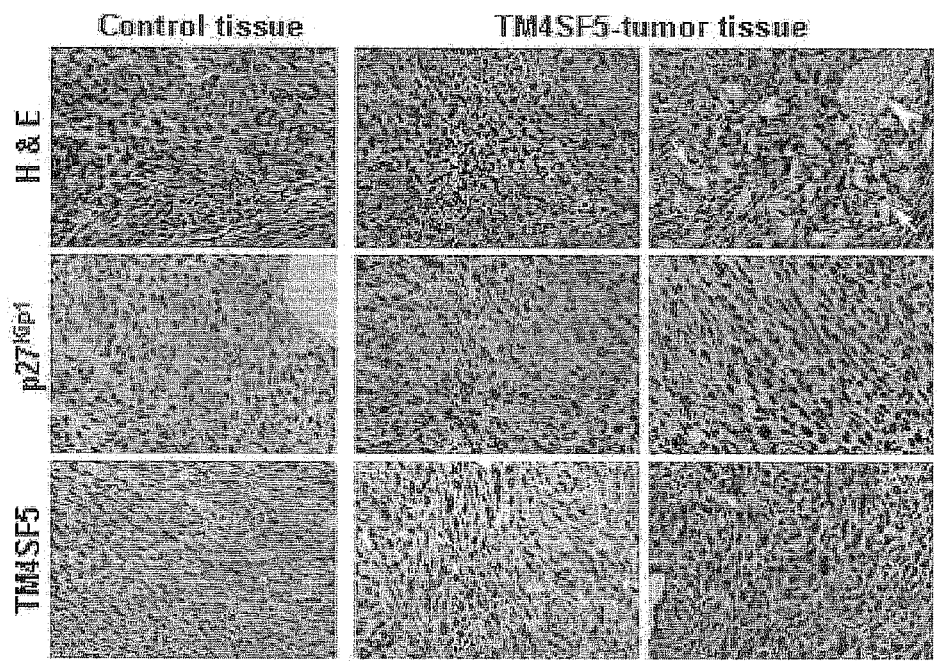
FIG. 54 shows the results of hematoxylin and eosin (H&E) staining and immunohistochemical staining of tumor tissues.
Figure 55:
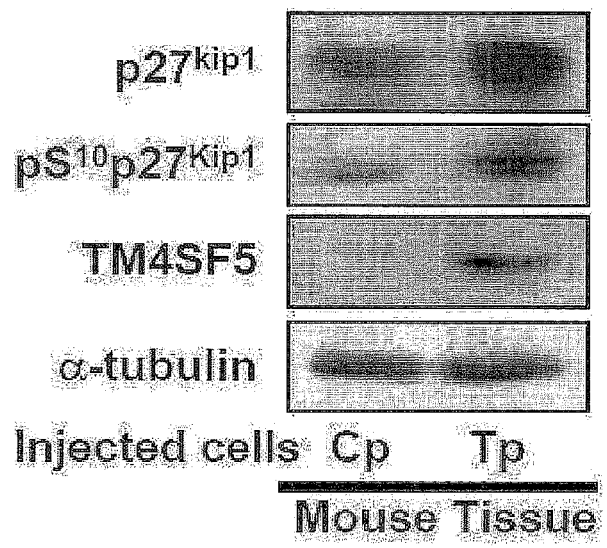
FIG. 55 shows the results of Western blotting of TM4SF5-induced tumor tissues for p27$^{kip1}$, pS10p27$^{kip1}$ and TM4SF5.

Tumor tissues from mice injected with SNU449 Cp and SNU449Tp cells were stained with hematoxylin and eosin for histological observation, and the expression of $p27^{kip1}$ and $pS10p27^{kip1}$ was analyzed using immunohistochemical staining. The immunohistochemical staining showed conspicuous cell death in the central region of tumor tissues induced by TM4SF5 and an increase in cytosolic levels and Ser10 phosphorylation of $p27^{kip1}$ (FIG. 54). Also, protein lysates from the above tissues were analyzed using Western blotting. TM4SF5-induced tumor tissues exhibited higher expression and phosphorylation of $p27^{kip1}$ than that of mouse tissues into which TM4SF5-null cells were injected (FIG. 55).

Example 7

Increase of Cell Motility by TM4SF5

(1) Evaluation of Cell Migration

Cell migration was examined using Boyden Transwell chamber 24 well plates (Costar, Cambridge, Mass.). SNU449 Cp and SNU449Tp cells were placed in a chamber on a polycarbonate filter (8 μm porosity) at a density of $5 \times 10^4$ cells/well, and cultured in serum-free RPMI (Roswell Park Memorial Institute) media in an incubator at 37° C. under 5% $CO_2$ for 24 hrs. Then, cells on the upper surface of the membrane of the insert chamber were completely removed by wiping with a cotton swab. Cells on the lower side of the membrane were fixed with 70% methanol for about 7 min.

SNU449 Cp and SNU449Tp cells were grown to confluency and wounded to a predetermined depth. Closure of the wounds was monitored over time under an optical microscope. As a result, it would be seen that TM4SF5-expressing cells showed more rapid wound healing than did TM4SF5-null cells (FIG. 58).

SNU449 Cp and SNU449Tp cells were placed in the insert wells of Transwell plates and cultured in serum-free medium. 10% serum-containing medium or serum-free medium was added to the lower chamber of the insert. To estimate the cell migration over time, cells were stained with 0.005% crystal violet for 1 min, washed with PBS three times, and observed under an optical microscope (see photographs of FIG. 59). Also, after the dye was dissolved, absorbance was measured at 260 nm, and is expressed as a bar graph (graph of FIG. 59). TM4SF5-expressing cells exhibited increased cell migration compared to TM4SF5-null cells (FIG. 59).

(2) Zymography Assay

The substrate degradation activity of secreted MMPs was investigated using gelatin zymography. Cell lines, indicated in FIG. 62, were cultured in 60-mm culture dishes. After 18 hrs, the medium was exchanged with serum-free medium, and cells were cultured for a further 24 hrs. Culture supernatants were collected to obtain secreted MMPs, and were then concentrated. Samples were electrophoresed on the running SDS-PAGE gel containing gelatin as a substrate for MMPs under reducing conditions. The gel was washed in 1% Triton X-100 to remove SDS, thus renaturing the enzymes. The gel was then incubated in enzyme reaction buffer (10 mM $CaCl_2$, 0.15 M NaCl, 50 mM Tris-HCl, pH 7.5) at 37° C. for 18 hrs. The gel was stained with 0.5% Coomassie Brilliant Blue R250 for 3 hrs, and destained until clear bands appeared in 10% acetic acid and 30% methanol.

As a result, the activity of MMP-2 and MMP-9, which degrade gelatin and fibronectin substrates, was found to increase in TM4SF5-expressing SNU449Tp, T3, T7 and T16 cells. These results indicate that the proteolytic activity of MMPs is increased by TM4SF5 (FIG. 62).

Figure 63:
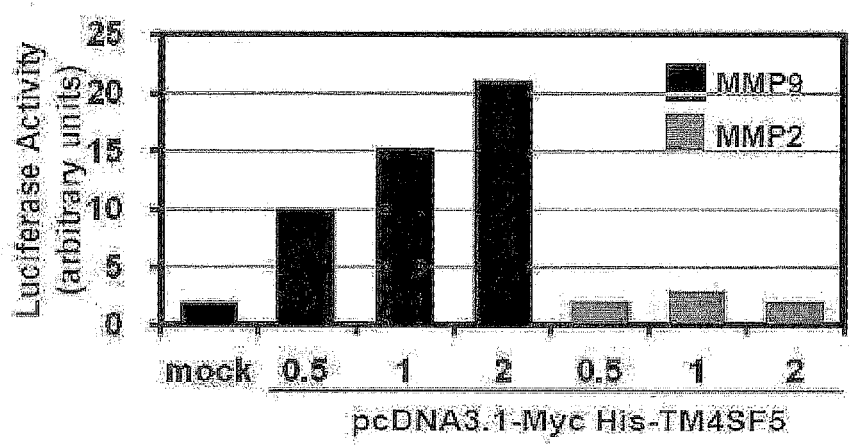
FIG. 63 shows the transcriptional activity of promoters of MMP-2 and MMP-9 genes in SNU449P cells, which were transfected with MMP-2 luciferase or MMP-9 luciferase along with pcDNA3.1-MycHis-TM4SF5.

In addition, SNU449P cells were co-transfected with MMP-2 luciferase or MMP-9 luciferase and various concentrations of pcDNA3.1-MycHis-TM4SF5. After 36 hrs, luciferase activity was measured to compare the transcriptional activity of MMP gene promoters. MMP-9 was found to have high gene expression level as well as high enzymatic activity (FIG. 63). These results indicate that TM4SF5 affects gene expression level of MMP genes.

(3) Evaluation of Cell Invasiveness Using 3D Collagen Gel Culture

Cell invasiveness was analyzed using Cytodex-3 microcarriers. SNU449 Cp and SNU449Tp cells were grown on microcarrier beads in an attached state, and cultured in a collagen gel matrix, including a serum-containing medium at 37° C. The optical microscopic observation showed the invasion of TM4SF5-expressing SNU449Tp cells into collagen gel (FIG. 60).

The invasiveness of SNU449Tp cells was also analyzed using Boyden Transwell chamber 24 well plates, as mentioned in Example 7-(1). Matrigel was added to the insert of the plates, and was allowed to solidify at 37° C. Cells were cultured as described above. After 24 hrs, cells on the upper surface of the membrane of the insert chamber were completely removed by wiping with a cotton swab. As a result, after 36 hrs, cells that had invaded the lower side of the membrane were stained. SNU449Tp cells were found to effectively invade Matrigel, which is an extracellular matrix complex (FIG. 62).

Example 8

Determination of Anticancer Substances (Antagonists) Inhibiting the Function of TM4SF5

Among compounds predicted to regulate the intracellular events specifically induced by TM4SF5, the chalcone compounds described in Table 1, above, were screened using the method of the present invention. Chalcone compounds indicated in FIG. 69 were also used as anticancer candidates.

Candidates exhibiting the aforementioned anticancer functions were determined to be the anticancer substances of the present invention. Representative compounds screened are listed in Table 1, above.

In order to further confirm the anticancer functions of the anticancer substances, among the compounds of Table 1,4'-(ρ-toluenesulfonylamino)-4-hydroxy chalcone (TSAHC) was used.

The treatment of TM4SF5-expressing cells with TSAHC reduced linear growth over time in a manner dependent on TSAHC concentrations (right graph, FIG. 43), inhibited S-phase progression (FIG. 44), and restored cell-cell contact (FIG. 45).

Figure 43:
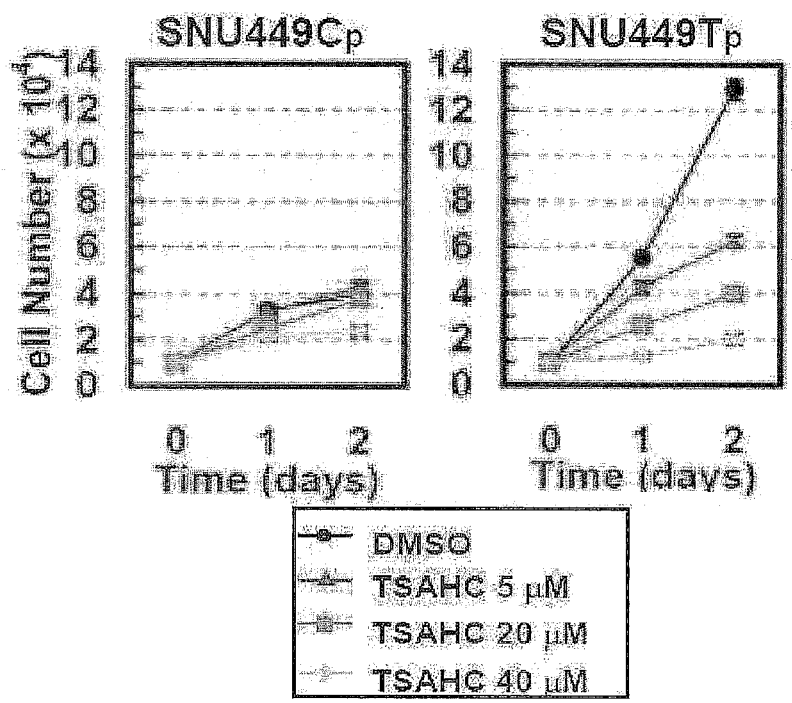
FIG. 43 shows the number of SNU449 Cp and SNU449Tp cells that survived when treated with DMSO or TSAHC (4'-(p-toluenesulfonylamino)-4-hydroxy chalcone) at given concentrations.
Figure 46:
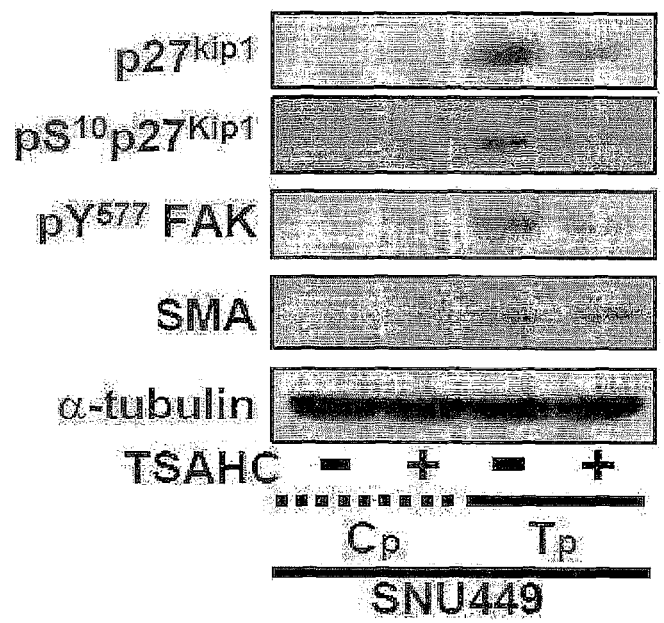
FIG. 46 shows the results of Western blotting for indicated proteins.

In contrast, TSAHC did not affect TM4SF5-null cells (left graph, FIG. 43). Also, TSAHC was found to effectively reduce TM4SF5-mediated high expression levels of $p27^{kip1}$, $pS^{10}p27^{kip1}$, $pY^{577}FAK$ and α-SMA (FIG. 46). The treatment of 449Tp cells with TSAHC resulted in a decrease in cytosolic $p27^{kip1}$ levels (FIG. 47), indicating that TSAHC acts as an antagonist against TM4SF5, thereby interrupting the stabilization of $p27^{kip1}$. Further, TSAHC restored the reduced RhoA activity in TM4SF5-expressing cells (FIG. 48), and returned the elongated cell shape to the same polygonal shape as that of TM4SF5-null control cells (FIG. 49).

In addition, the TSAHC treatment was found to increase the sensitivity of an N-linked glycosylated region of TM4SF5 to PNGase F (FIG. 50). These results indicate that TSAHC attack TM4SF5 itself to modify the N-linked glycosylation structure and to affect the binding of TM4SF5 with other proteins (in the tetraspanin-web), thereby inhibiting the tumorigenic function of TM4SF5.

Figure 51:
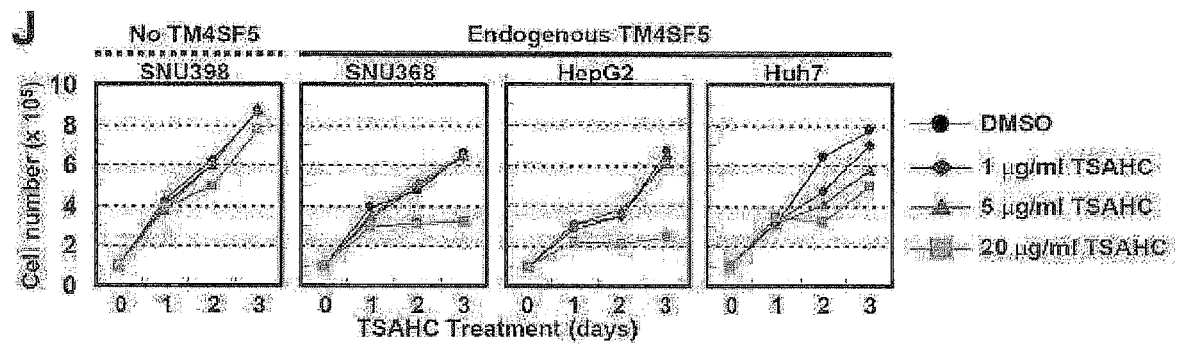
FIG. 51 shows the changes in growth/proliferation of TM4SF5-expressing cells and TM4SF5-null cells when treated with TSAHC.

The TSAHC treatment inhibited the growth or proliferation of cells endogenously expressing TM4SF5, but did not affect cells not expressing TM4SF5 (FIG. 51). These results indicate that chalcone compounds, acting as an antagonist against TM4SF5, have preventive and therapeutic effects on TM4SF5-mediated tumorigenesis.

The concentrations of chalcone compounds producing 50% inhibition ($IC_{50}$) against TM4SF5 are given in Table 2, below.

TABLE 2

| Compound | Inhibition conc. ($IC_{50}$, mM) |
|---|---|
| 1 | 4.6 |
| 2 | 7.5 |
| 3 | 10.1 |
| 4 | 13.7 |
| 5 | 14.9 |
| 6 | 26.8 |
| 7 | 30.2 |
| 8 | 33.4 |
| 9 | 58.2 |
| 10 | 44.4 |
| 11 | 70.5 |
| 12 | 87.7 |
| 13 | 67.8 |
| 14 | 83.1 |
| 15 | 49.1 |
| 16 | 66.3 |
| 17 | 53.4 |
| 18 | 50.3 |
| 19 | 40.2 |
| 20 | 53.4 |
| 21 | 72.3 |
| 22 | 50.4 |
| 23 | 65.4 |

TABLE 2-continued

| Compound | Inhibition conc. ($IC_{50}$, mM) |
|---|---|
| 24 | 25.3 |
| 25 | 12.6 |
| 26 | 17.5 |
| 27 | 16.2 |
| 28 | 8.9 |
| 29 | 28.6 |
| 30 | 11.9 |
| 31 | 10.5 |
| 32 | 8.4 |
| 33 | 19.2 |
| 34 | 33.7 |
| 35 | 26.8 |
| 36 | 24.8 |
| 37 | 15.3 |
| 38 | 17.3 |
| 39 | 9.3 |
| 40 | 32.5 |
| 41 | 15.3 |

Example 9

Evaluation of In Vitro Cytotoxicity of Chalcone Derivatives of the Present Invention Against Human Carcinoma Cell Lines The chalcone derivatives of the present invention were evaluated for in vitro cytotoxicity against human carcinoma cell lines using a sulforhodamine B (SRB) method, which was developed in 1989 by the National Cancer Institute (NCI), USA.

HCT15 (colon adenocarcinoma; ATCC CCL-225), PC-3 (prostate adenocarcinoma; ATCC CRL-1435), and A-549 (lung carcinoma; ATCC CCL-185) cell lines were used. All of these carcinoma cells were sub-cultured at the Korean Research Institute of Bioscience and Biotechnology (KRIBB), Korea.

The human carcinoma cell lines were cultured in 10% FCS-containing RPMI 1640 medium (Gibco Cat. No. 31800) in an incubator at 37° C. under 5% $CO_2$, and sub-cultured twice per week.

Cells were detached from the attached surface using 0.25% Trypsin (Sigma) and 3 mM CDTA (1,2-cyclohexane diamine tetraacetic acid, Sigma) in phosphate buffered saline (PBS, Sigma).

Compounds to be tested (the chalcone derivatives set forth in Table 1) were dissolved in a small amount of dimethylsulfoxide (DMSO, Sigma), and diluted in culture medium to a desired concentration. The final concentration of DMSO was less than 0.5%. The diluted compounds (final concentration: 30, 10, 3, 1 and 0.3 μg/ml) were sterilized through a 0.22-μm microfilter (Millipore). The cytotoxicity of the compounds to human carcinoma cell lines was assessed using a typical SRB method.

The cytotoxicity ($ED_{50}$, μg/ml) of the chalcone derivatives of the present invention against human carcinoma cell lines is summarized in Table 3, below.

TABLE 3

| Compound | HCT-15 | A-549 | PC-3 |
|---|---|---|---|
| 1 | 35 | 38 | 37 |
| 2 | 37 | 36 | 39 |
| 3 | 40 | 35 | 37 |
| 4 | 38 | 34 | 37 |
| 5 | 42 | 40 | 47 |

TABLE 3-continued

| Compound | HCT-15 | A-549 | PC-3 |
|---|---|---|---|
| 6 | 37 | 41 | 33 |
| 7 | 33 | 30 | 37 |
| 8 | 30 | 31 | 34 |
| 9 | 24 | 40 | 31 |
| 10 | 30 | 30 | 32 |
| 11 | 39 | 38 | 41 |
| 12 | 37 | 35 | 37 |
| 13 | 38 | 36 | 41 |
| 14 | 38 | 31 | 29 |
| 15 | 33 | 43 | 41 |
| 16 | 37 | 33 | 47 |
| 17 | 32 | 33 | 44 |
| 18 | 33 | 31 | 39 |
| 19 | 38 | 47 | 53 |
| 20 | 40 | 35 | 39 |
| 21 | 31 | 39 | 43 |
| 22 | 28 | 27 | 45 |
| 23 | 35 | 31 | 37 |
| 24 | 55 | 50 | 51 |
| 25 | 54 | 51 | 57 |
| 26 | 22 | 20 | 28 |
| 27 | 41 | 34 | 47 |
| 28 | 54 | 59 | 57 |
| 29 | 29 | 37 | 21 |
| 30 | 52 | 50 | 59 |
| 31 | 24 | 34 | 27 |
| 32 | 47 | 45 | 41 |
| 33 | 47 | 45 | 42 |
| 34 | 54 | 74 | 64 |
| 35 | 51 | 47 | 57 |
| 36 | 48 | 41 | 39 |
| 37 | 34 | 37 | 27 |
| 38 | 52 | 57 | 47 |
| 39 | 39 | 37 | 38 |
| 40 | 31 | 30 | 39 |
| 41 | 42 | 49 | 48 |
| 42 | 7 | 10 | 18 |
| 43 | 12 | 18 | 14 |
| 44 | 8 | 10 | 16 |
| 45 | 11 | 12 | 14 |
| 46 | 9 | 13 | 8 |
| 47 | 8 | 11 | 17 |
| 48 | 7 | 8 | 11 |
| 49 | 8 | 6 | 14 |
| 50 | 9 | 10 | 9 |
| 51 | 6 | 13 | 11 |
| 52 | 7 | 6 | 5 |
| 53 | 8 | 7 | 8 |
| 54 | 7 | 9 | 9 |
| 55 | 6 | 7 | 12 |
| 56 | 5 | 3 | 6 |
| 57 | 9 | 7 | 10 |
| 58 | 11 | 12 | 10 |
| 59 | 9 | 13 | 20 |
| 60 | 4 | 7 | 8 |
| 61 | 12 | 10 | 10 |
| 62 | 7 | 12 | 8 |
| 63 | 8 | 10 | 14 |
| 64 | 4 | 3 | 7 |
| 65 | 9 | 4 | 13 |
| 66 | 11 | 11 | 13 |
| 67 | 7 | 14 | 15 |
| 68 | 6 | 8 | 10 |
| 69 | 7 | 8 | 16 |
| 70 | 8 | 9 | 11 |
| 71 | 12 | 7 | 24 |
| 72 | 10 | 11 | 8 |
| 73 | 7 | 11 | 8 |
| 74 | 8 | 11 | 14 |
| 75 | 8 | 14 | 15 |
| 76 | 12 | 11 | 17 |
| 77 | 10 | 11 | 12 |
| 78 | 5 | 10 | 7 |
| 79 | 7 | 8 | 15 |
| 80 | 13 | 11 | 23 |
| 81 | 14 | 28 | 24 |
| 82 | 12 | 17 | 22 |
| 83 | 15 | 11 | 14 |
| 84 | 32 | 38 | 22 |
| 85 | 29 | 33 | 28 |
| 86 | 26 | 30 | 34 |
| 87 | 19 | 20 | 21 |
| 88 | 21 | 32 | 28 |
| 89 | 24 | 37 | 33 |
| 90 | 6 | 4 | 8 |
| 91 | 7 | 10 | 14 |
| 92 | 8 | 9 | 7 |
| 93 | 6 | 8 | 14 |
| 94 | 7 | 11 | 16 |
| 95 | 9 | 9 | 11 |
| 96 | 8 | 7 | 24 |
| 97 | 11 | 6 | 8 |

The results indicate that the chalcone compounds of the present invention have potential as anticancer agents due to their cytotoxicity to human carcinoma cell lines.

Example 10

Inhibitory Effect of TSAHC on Tumorigenesis (1) TSAHC Administration

The length and width of tumors formed in nude mice, prepared in Example 6, were measured one every two days using calipers. Tumor volume was calculated according to the following Equation: Volume $(mm^3)$=Length×Width2×½, Length: long diameter, Width: short diameter).

When tumors induced in nude mice (that is, tumors implanted in mice) reached a size of 200 $mm^3$, mice were divided into two groups. TSAHC (5 mg/kg and 50 mg/kg) was suspended in physiological saline and intraperitoneally injected once every two days for a period of three weeks using a 26-guage syringe.

(2) Immunohistochemistry and Western Blotting of Tumor Tissues

In the 6th week after injection of SNU449Tp cells or at the $3^{rd}$ week after TSAHC administration, nude mice were sacrificed by cervical dislocation. For immunohistochemical examination, tumor tissues were sectioned, fixed with formaldehyde, and paraffin-embedded. In order to examine protein expression levels using Western blotting, excised tumor tissues were immediately frozen in liquid nitrogen and dissolved in 0.1% SDS-containing RIPA buffer to obtain a protein mixture for analysis. 6-µm paraffin sections were subjecting to hematoxylin and eosin staining and immunohistochemical examination.

Figure 56:
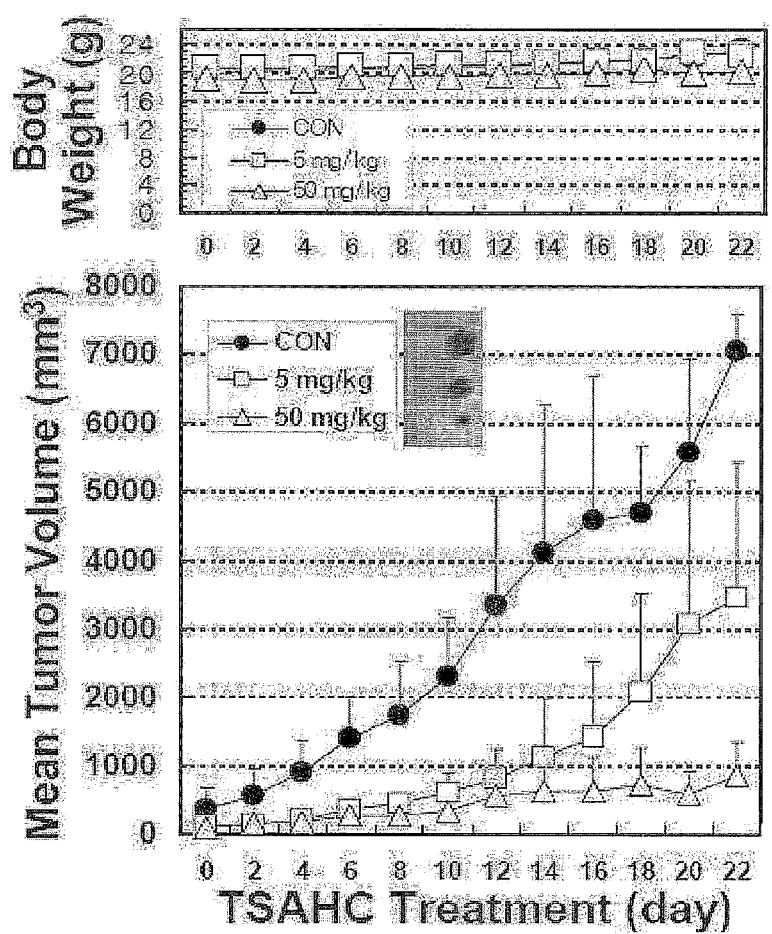
FIG. 56 shows the tumor volume and body weight of animals upon intraperitoneal injection with TSAHC.

As a result, tumors (n=6) formed in mice implanted with TM4SF5-expressing cells continued to enlarge. In contrast, when TSAHC was intraperitoneally injected at a dose of 5 mg/kg or 50 mg/kg, tumor size decreased by 45% and 88%, respectively (FIG. 56).

Example 11

Inhibitory Effect of TSAHC on Tumor Metastasis (1) Establishment of Animal Model for Tumor Metastasis An experimental animal model for tumor metastasis was prepared according to the same method as in the tumor-induced model (see Example 6). SNU449 Cp and SNU449Tp cell suspensions were centrifuged, and the concentrated cells were counted using a hemocytometer. $1 \times 10^7$ cells were intravenously injected into the tails of nude mice. After 3 weeks, mice were sacrificed, and lung tissues were excised, fixed with formaldehyde and stained with hematoxylin and eosin.

Figure 64:
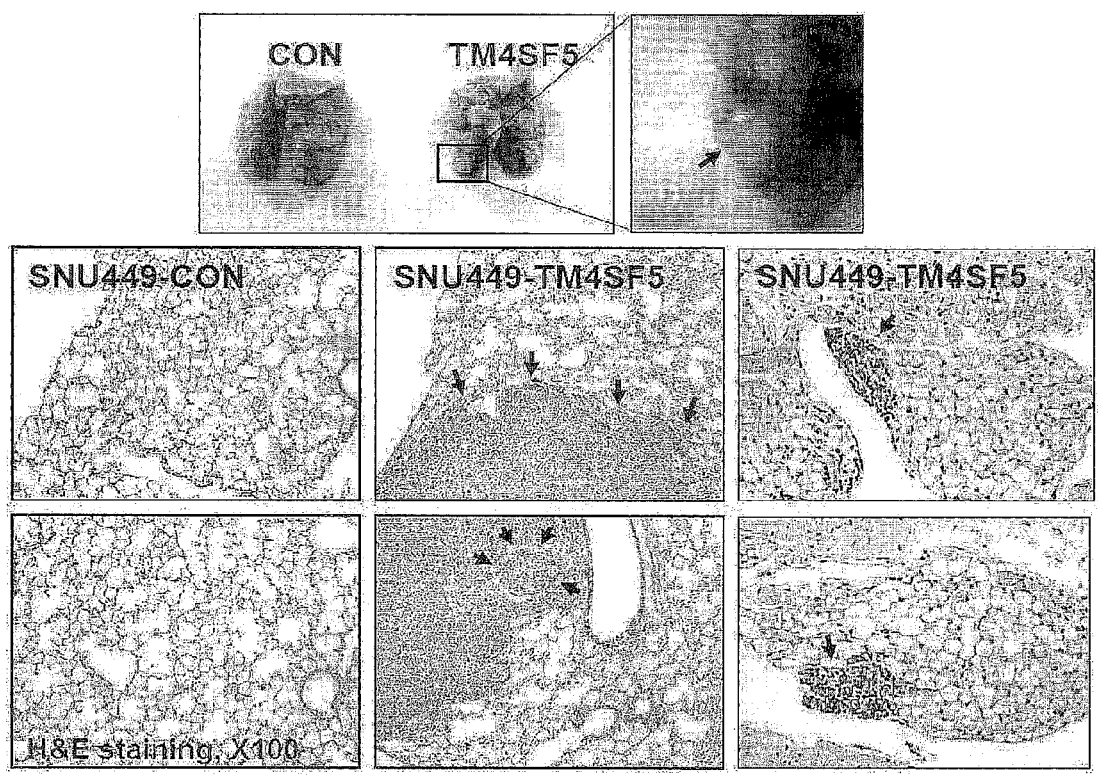
FIG. 64 shows the tumor mass formed in the lung tissue of a mouse, which was intravenously injected with TM4SF5-expressing cells via the tail, and the results of H&E staining, displaying tumor metastasis.

When mice were injected with TM4SF5-expressing cells, a tumor mass was formed in lung tissue (FIG. 64). In FIG. 64, the arrow indicates the formed tumor mass, in which cells were crowded.

(2) Inhibitory Effect of TSAHC on TM4SF5-Mediated Cell Migration and Invasion

Figure 65:
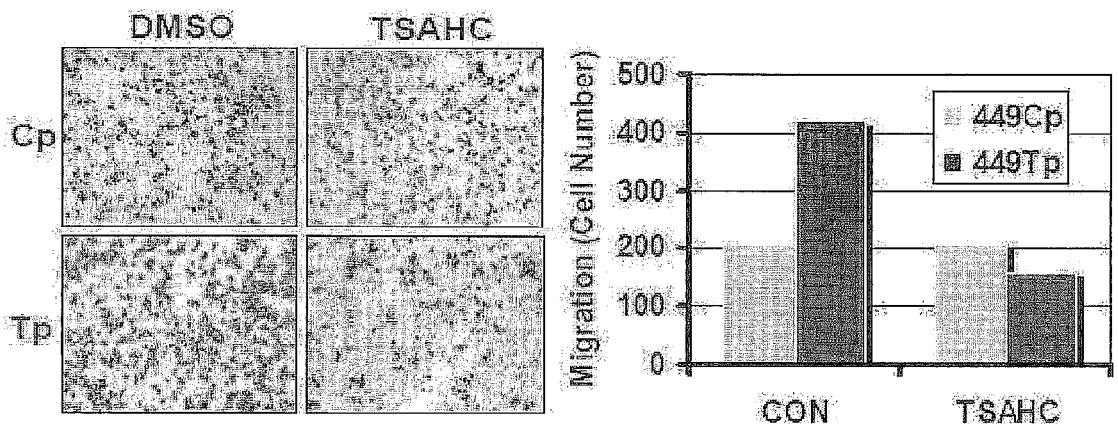
FIG. 65 shows the results of staining and the number of cells that migrated, when SNU449 Cp and SNU449Tp cells were treated or not treated with TSAHC.

SNU449 Cp cells and SNU449Tp cells were plated onto 6-well plates and cultured for 24 hrs. Cells were then treated with 20 μM of TSAHC to culture for 18 hrs. Cells were transferred into insert wells of the Transwell chamber. After 18 hrs, migrated cells were fixed, stained, and observed under an optical microscope. Cells were counted, and the results were expressed as a graph (FIG. 65). As a result, TSAHC was found to inhibit TM4SF5-mediated cell migration.

Figure 66:
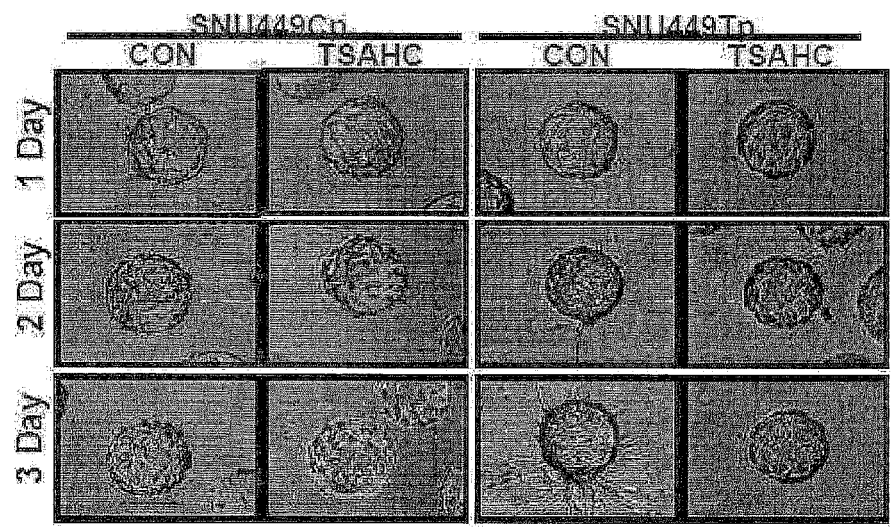
FIG. 66 shows the invasion of SNU449 Cp and SNU449Tp cells, which were treated with TSAHC or not, into collagen gels.

SNU449 Cp cells and SNU449Tp cells were allowed to attach to microcarrier beads, and cultured in the presence of 20 μM of TSAHC for 18 hrs. Bead-cells were cultured in a collagen gel matrix, including a serum-containing medium, and observed for invasion into the collagen gel at given time points. As a result, TSAHC was found to inhibit TM4SF5-mediated cell invasion into collagen gel (FIG. 66).

Figure 67:
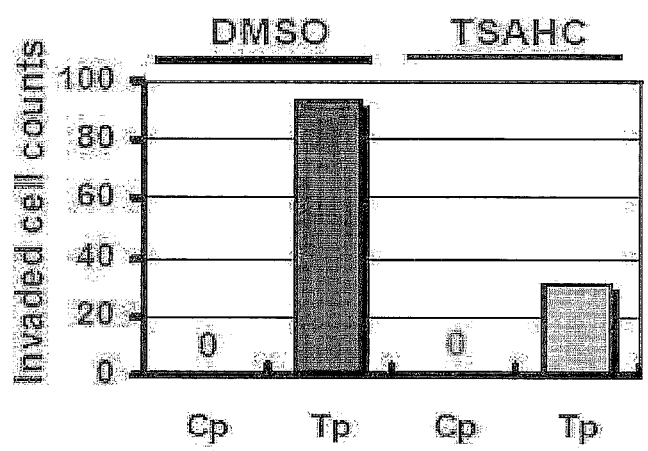
FIG. 67 shows the invasion of SNU449 Cp and SNU449Tp cells, which were treated with TSAHC or not, into Matrigel.

According to the same method described above, cells were seeded in the Transwell chamber, coated with a thick layer of Matrigel, and cultured for 24 hrs. Cells that invaded the Matrigel were counted, and the results are shown as a graph. As a result, TSAHC was also found to effectively inhibit invasion into Matrigel (FIG. 67).

Figure 68:
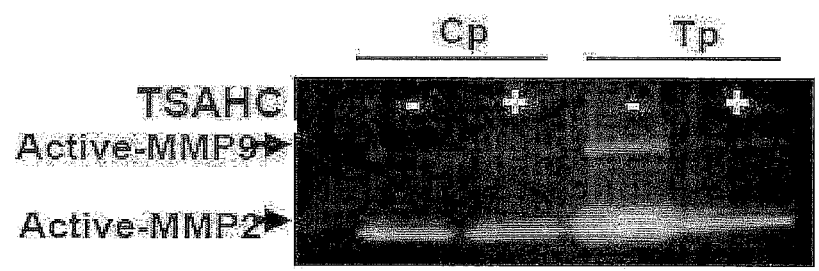
FIG. 68 shows the results of zymography for the activity of MMP-2 and MMP-9 in SNU449Cp and SNU449Tp cells, which were treated or not treated with TSAHC.

In addition, Cp cells and Tp cells were treated with 20 μM of TSAHC for 24 hrs. The medium was exchanged with serum-free medium, and cells were cultured for a further 18 hrs. Culture supernatants were collected, concentrated, and analyzed using zymography, as described above. As a result, TSAHC was found to inhibit the TM4SF5-mediated activity of MMPs (FIG. 68).

These results indicate that TSAHC effectively inhibits the metastasis process of tumor cells as well as tumorigenesis.

Example 12

Comparison of Effects of TSAHC and its Analogues

TSAHC and its structural analogues were compared for their effects on TM4SF5-mediated events. Dimethyl sulfoxide (DMSO) and chalcone analogues, used in this test, have the following chemical structure.

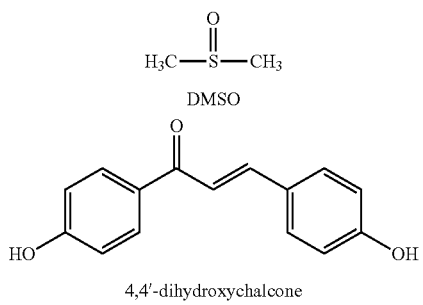

4,4'-dihydroxychalcone

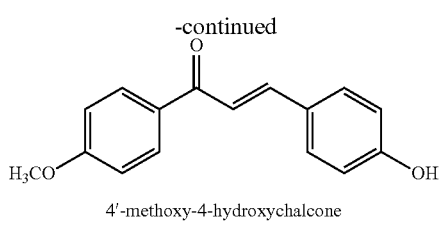

4'-methoxy-4-hydroxychalcone

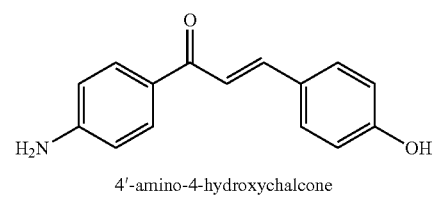

4'-amino-4-hydroxychalcone

SNU449 Cp cells and SNU449Tp cells were plated onto 6-well plates and treated with the above compounds at 20 μM for 24 hrs. Cells were monitored for changes in cell morphology using an optical microscope.

Figure 69:
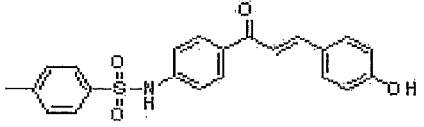
FIG. 69 shows ahanges in the morphology of SNU449 Cp and SNU449Tp cells, which were treated with the compounds indicated.
Figure 69:
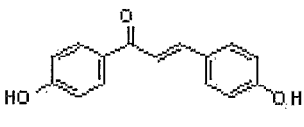
Figure 69:
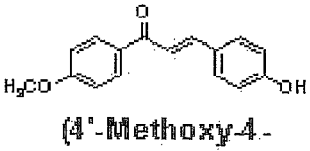
Figure 69:
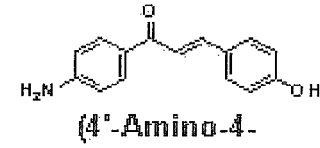

As shown in FIG. 69, under the same treatment conditions (20 μM, 24 hr treatment), TSAHC, unlike the above TSAHC analogues that had almost the same structure as TSAHC or were substituted with a different R group, was found to effectively stimulate the growth of TM4SF5-expressing cells, not in a multilayer but in a monolayer arrangement, and changed the cell morphology into the same shape as that of SNU449 control cells not expressing TM4SF5. These results indicate that the effect of TM4SF5 on the contact inhibition of cell growth may be regulated by a specific R group of the TSAHC compound.

The TSAHC analogues, as shown in the above chemical structures, have OH, $NH_2$ or $OCH_3$ as a substituent on the A-ring (left ring) of chalcone. Such TSAHC analogues did not display anticancer activity, inhibiting TM4SF5-mediated multilayer growth. In contrast, a sulfonamide chalcone compound such as TSAHC, into which a sulfonyl group was introduced, exhibited anticancer activity by inhibiting the TM4SF5 function. That is, the introduction of a sulfonyl group into a chalcone compound confers unique anticancer activity, which is distinct from known chalcone derivatives.

INDUSTRIAL APPLICABILITY

As described in detail above, the present invention provides a method for screening an anticancer substance based on the molecular mechanism of TM4SF5-mediated tumorigenesis. The method is useful in screening therapeutic and preventive substances acting as antagonists against tumor formation and metastasis. In addition, the anticancer composition of the present invention, comprising a chalcone compound screened using the method, exhibits anticancer activity with no weight loss, no abnormal appearance of the liver or spleen, and no toxic effects. Thus, the compound is useful as an anticancer drug.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

We claim:

1. A method for screening an anticancer compound for liver cancer, comprising:
   (a) culturing an artificially established hepatocarcinoma cell line expressing the polypeptide of SEQ ID NO: 2 from a vector, and treating the hepatocarcinoma cells with an anticancer candidate;
   (b) detecting at least one of the following in the hepatocarcinoma cells treated with the anticancer candidate: (i) phosphorylation of a tyrosine residue at positions 577 (Tyr577) of an amino acid sequence encoding focal adhesion kinase (FAK), (ii) binding of FAK to Rho-GTPase activating protein (RhoGAP) or FAK to GTPase regulator associated with FAK (GRAF), (iii) cytosolic $p27^{Kip1}$ expression level and stability, (iv) RhoA activity, and (v) Rac1 activity; and
   (c) determining whether the anticancer candidate can be an anticancer substance for liver cancer when the following events are exhibited, compared to when treatment with the anticancer candidate is not conducted: (i) decreased phosphorylation of FAK on Tyr577, (ii) inhibition of binding of FAK to RhoGAP or FAK to GRAF, (iii) reduced cytosolic $p27^{Kip1}$ expression level and stability, (iv) increased RhoA activity, or (v) decreased Rac1 activity.

2. The method for screening an anticancer compound according to claim 1, wherein the cytosolic $p27^{Kip1}$ is the phosphorylated $p27^{Kip1}$ on Ser 10.

3. The method for screening an anticancer compound according to claim 1,
   wherein the step (b) further includes detecting at least one selected from the group consisting of cell morphology, expression of a protein involved in cell adhesion formation, cell-cell contact pattern or contact growth, expression of α-smooth muscle actin (α-SMA) or vimentin, expression of E-cadherin, and epithelial-mesenchymal transition (EMT); and
   the step (c) further includes the following events: a change in cell morphology from a rod shape into a polygonal shape, reduced expression of proteins involved in cell adhesion formation, maintenance of cell-cell contact, contact inhibition of cell growth, reduced expression of α-SMA or vimentin, increased expression of E-cadherin, or reduced epithelial-mesenchymal transition (EMT).

4. The method for screening an anticancer compound according to claim 3, wherein the protein involved in cell-cell adhesion formation is selected from the group consisting of E-cadherin, zonula occludens-1 (ZO1), β-catenin and desmoplakin.

5. The method for screening an anticancer compound according to claim 3, wherein contact inhibition of cell growth is through the reduction of cell number, reduction of cell population in S-phase, or inhibition of multilayer growth.

6. The method for screening an anticancer compound according to claim 5, wherein the reduction of cell number or reduction of S-phase cell population is mediated through the inactivation of N-linked glycosylation of membrane proteins.

7. The method for screening an anticancer compound according to claim 1,
   wherein the step (b) further includes detecting at least one selected from the group consisting of cell migration or motility in the presence of an extracellular matrix or serum, the invasion into collagen gels which comprise the extracellular matrix, the invasion into Matrigel which is an extracellular matrix complex, and matrix metalloproteinase (MMP) activity; and
   the step (c) further includes the following events: decreased cell migration or motility in the presence of an extracellular matrix or serum, decreased invasion into collagen gels, decreased invasion into Matrigel, or reduction of MMP activity.

8. The method for screening an anticancer compound according to claim 7, wherein said MMP is MMP-2 or MMP-9.

9. The method for screening an anticancer compound according to claim 3,
   wherein the step (b) further includes detecting at least one selected from the group consisting of cell migration or motility in the presence of an extracellular matrix or serum, the invasion into collagen gels which comprise the extracellular matrix, the invasion into Matrigel which is an extracellular matrix complex, and matrix metalloproteinase (MMP) activity; and
   the step (c) further includes the following events: decreased cell migration or motility in the presence of an extracellular matrix or serum, decreased invasion into collagen gels, decreased invasion into Matrigel, or reduction of MMP activity.

10. The method for screening an anticancer compound according to claim 9, wherein said MMP is MMP-2 or MMP-9.

11. The method of claim 1, wherein the artificially established hepatocarcinoma cell line expressing the polypeptide of SEQ ID NO: 2 from a vector is an SNU449 cell line or an SNU398 cell line transfected with a retroviral vector comprising the nucleic acid sequence of SEQ ID NO: 1.

* * * * *

SEQUENCE LISTING

<160> NUMBER OF SEQ ID NOS: 4

<210> SEQ ID NO 1
<211> LENGTH: 708
<212> TYPE: DNA
<213> ORGANISM: Homo sapiens

<400> SEQUENCE: 1

```
actcaccgcc tgtccttcct gacacctcac catgtgtacg ggaaaatgtg cccgctgtgt      60
ggggctctcc ctcattaccc tctgcctcgt ctgcattgtg ccaacgccc tcctgctggt     120
acctaatggg gagacctcct ggaccaacac caaccatctc agcttgcaag tctggctcat    180
gggcggcttc attggcgggg gcctaatggt actgtgtccg gggattgcag ccgttcgggc    240
agggggcaag ggctgctgtg gtgctgggtg ctgtggaaac cgctgcagga tgctgcgctc    300
ggtcttctcc tcggcgttcg gggtgcttgg tgccatctac tgcctctcgg tgtctggagc    360
tgggctccga aatggaccca gatgcttaat gaacggcgag tggggctacc acttcgaaga    420
caccgcggga gcttacttgc tcaaccgcac tctatgggat cggtgcgagg cgccccctcg    480
cgtggtcccc tggaatgtga cgctcttctc gctgctggtg ccgcctcct gcctggagat    540
agtactgtgt gggatccagc tggtgaacgc gaccattggt gtcttctgcg gcgattgcag    600
gaaaaacag gacacacctc actgaggctc cactgaccgc cgggttacac ctgctccttc    660
ctggacgctc actcccttgc tcgctagaat aaactgcttt gcgctctc                 708
```

<210> SEQ ID NO 2
<211> LENGTH: 197
<212> TYPE: PRT
<213> ORGANISM: Homo sapiens

<400> SEQUENCE: 2

```
Met Cys Thr Gly Lys Cys Ala Arg Cys Val Gly Leu Ser Leu Ile Thr
1               5                   10                  15

Leu Cys Leu Val Cys Ile Val Ala Asn Ala Leu Leu Leu Val Pro Asn
            20                  25                  30

Gly Glu Thr Ser Trp Thr Asn Thr Asn His Leu Ser Leu Gln Val Trp
        35                  40                  45

Leu Met Gly Gly Phe Ile Gly Gly Gly Leu Met Val Leu Cys Pro Gly
    50                  55                  60

Ile Ala Ala Val Arg Ala Gly Lys Gly Cys Cys Gly Ala Gly Cys
65                  70                  75                  80

Cys Gly Asn Arg Cys Arg Met Leu Arg Ser Val Phe Ser Ser Ala Phe
                85                  90                  95

Gly Val Leu Gly Ala Ile Tyr Cys Leu Ser Val Ser Gly Ala Gly Leu
            100                 105                 110

Arg Asn Gly Pro Arg Cys Leu Met Asn Gly Glu Trp Gly Tyr His Phe
        115                 120                 125

Glu Asp Thr Ala Gly Ala Tyr Leu Leu Asn Arg Thr Leu Trp Asp Arg
    130                 135                 140

Cys Glu Ala Pro Pro Arg Val Val Pro Trp Asn Val Thr Leu Phe Ser
145                 150                 155                 160

Leu Leu Val Ala Ala Ser Cys Leu Glu Ile Val Leu Cys Gly Ile Gln
                165                 170                 175

Leu Val Asn Ala Thr Ile Gly Val Phe Cys Gly Asp Cys Arg Lys Lys
            180                 185                 190

Gln Asp Thr Pro His
        195
```

```
                                                       195

<210> SEQ ID NO 3
<211> LENGTH: 20
<212> TYPE: DNA
<213> ORGANISM: Homo sapiens

<400> SEQUENCE: 3
taacccggga cttggagaag                                                  20

<210> SEQ ID NO 4
<211> LENGTH: 19
<212> TYPE: DNA
<213> ORGANISM: Homo sapiens

<400> SEQUENCE: 4
gcttcttggg cgtctgctc                                                   19
```